US007763657B2

(12) United States Patent
Kim et al.

(10) Patent No.: US 7,763,657 B2
(45) Date of Patent: Jul. 27, 2010

(54) COMPOUNDS, ISOMER THEREOF, OR PHARMACEUTICALLY ACCEPTABLE SALTS THEREOF AS VANILLOID RECEPTOR ANTAGONIST; AND PHARMACEUTICAL COMPOSITIONS CONTAINING THE SAME

(75) Inventors: Hee-Doo Kim, Seoul (KR); Young-Ger Suh, Seoul (KR); Hyeung-Geun Park, Seoul (KR); Uh Taek Oh, Seoul (KR); Seol Rin Park, Pusan-si (KR); Joo Hyun Kim, Daejeon (KR); Mi Jung Jang, Seongnam-si (KR); Young-Ho Park, Seoul (KR); Song Seok Shin, Yongin-si (KR); Sun-Young Kim, Seoul (KR); Jin Kwan Kim, Suwon-si (KR); Yeon Su Jeong, Yongin-si (KR); Ki-Wha Lee, Seoul (KR); Jin Kyu Choi, Suwon-si (KR); Kyung Min Lim, Suwon-si (KR); Hyun Ju Koh, Gunpo-si (KR); Joo Hyun Moh, Yongin-si (KR); Sung-Il Kim, Yangju-si (KR); Byoung Young Woo, Yongin-si (KR)

(73) Assignee: Amorepacific Corporation, Seoul (KR)

(*) Notice: Subject to any disclaimer, the term of this patent is extended or adjusted under 35 U.S.C. 154(b) by 223 days.

(21) Appl. No.: 11/909,136

(22) PCT Filed: Mar. 15, 2006

(86) PCT No.: PCT/KR2006/000929

§ 371 (c)(1),
(2), (4) Date: Nov. 15, 2007

(87) PCT Pub. No.: WO2006/101318

PCT Pub. Date: Sep. 28, 2006

(65) Prior Publication Data

US 2009/0105258 A1     Apr. 23, 2009

Related U.S. Application Data

(60) Provisional application No. 60/663,269, filed on Mar. 21, 2005.

(30) Foreign Application Priority Data

Mar. 19, 2005  (KR) ............... 10-2005-0022986

(51) Int. Cl.
```
A61K 31/17      (2006.01)
A61K 31/18      (2006.01)
A61K 31/351     (2006.01)
A61K 31/4453    (2006.01)
A61K 31/45      (2006.01)
A61K 31/445     (2006.01)
A61K 31/495     (2006.01)
A61K 31/5375    (2006.01)
C07D 241/04     (2006.01)
C07D 265/30     (2006.01)
C07D 211/06     (2006.01)
C07D 211/46     (2006.01)
C07D 315/00     (2006.01)
C07C 311/08     (2006.01)
C07C 275/24     (2006.01)
```

(52) U.S. Cl. .................. 514/595; 514/605; 514/255.03; 514/331; 514/327; 514/237.8; 514/460; 544/159; 544/393; 546/216; 546/234; 549/419; 564/56; 564/99

(58) Field of Classification Search ................. 514/595, 514/605, 255.03, 331, 327, 237.8, 460; 544/159, 544/393; 546/216, 234; 549/419; 564/56, 564/99

See application file for complete search history.

(56) References Cited

U.S. PATENT DOCUMENTS

| 7,566,739 B2 * | 7/2009 | Hanazawa et al. .......... 514/605 |
| 2003/0153596 A1 | 8/2003 | Suh et al. |
| 2004/0157865 A1 | 8/2004 | Cod et al. |

(Continued)

FOREIGN PATENT DOCUMENTS

WO      WO 02/16318 A1      2/2002

(Continued)

OTHER PUBLICATIONS

Gunthorpe et al. Current Pharmaceutical Design 2008, 14, 32-41.*
Schafer et al. Drug Discovery Today 2008, 13 (21/22), 913-916.*
Horig et al. Journal of Translational Medicine 2004, 2(44).*

(Continued)

*Primary Examiner*—Rebecca L Anderson
*Assistant Examiner*—Jason M Nolan
(74) *Attorney, Agent, or Firm*—Rothwell, Figg, Ernst & Manbeck, P.C.

(57) ABSTRACT

This present invention relates to novel compounds, isomer thereof or pharmaceutically acceptable salt thereof as vanilloid receptor (Vanilloid Receptor 1; VR1; TRRPV1) antagonist; and a pharmaceutical composition containing the same. The present invention provides a pharmaceutical composition for preventing or treating a disease such as pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, and heart disease.

18 Claims, No Drawings

FOREIGN PATENT DOCUMENTS

| | | |
|---|---|---|
| WO | WO 03/049702 A2 | 6/2003 |
| WO | WO 03/095420 A1 | 11/2003 |
| WO | WO 2005/003084 A1 | 1/2005 |

OTHER PUBLICATIONS

Mezey, E. et al., "Distribution of mRNA for vanilloid receptor subtype 1 (VR1), and VR1-like immunoreactivity, in the central nervous system of the rat and human", *PNAS*, vol. 97, No. 7, pp. 3655-3660, Mar. 28, 2000.

Cortright, D. et al., "The Tissue Distribution and Functional Characterization of Human VR1", *Biochemical and Biophysical Research Communications*, vol. 281, pp. 1183-1189, Feb. 6, 2001.

Nagy, I. et al., "The role of the vanilloid (capsaicin) receptor (TRPV1) in physiology and pathology", *European Journal of Pharmacology*, vol. 500, pp. 351-369, Aug. 17, 2004.

Petersen, K. et al., "Capsaicin evoked pain and allodynia in post-herpetic neuralgia", *PAIN*, vol. 88, pp. 125-133, Apr. 11, 2000.

Walker, K. et al., "The VR1 Antagonist Capsazepine Reverses Mechanical Hyperalgesia in Models of Inflammatory and Neuropathic Pain", *The Journal of Pharmacology and Experimental Therapeutics*, vol. 304, No. 1, pp. 56-62, Sep. 9, 2002.

Kim, S. et al., "Transient Receptor Potential Vanilloid Subtype 1 Mediates Cell Death of Mesencephalic Dopaminergic Neurons In Vivo and In Vitro", *The Journal of Neuroscience*, vol. 25(3), pp. 662-671, Jan. 19, 2005.

Kamei, J. et al., "Role of vanilloid VR1 receptor in thermal allodynia and hyperalgesia in diabetic mice", *European Journal of Pharmacology*, vol. 422, pp. 83-86, May 15, 2001.

Chan, C. et al., "Sensory fibres expressing capsaicin receptor TRPV1 in patients with rectal hypersensitivity and faecal urgency", *The Lancet*, vol. 361, pp. 385-391, Feb. 1, 2003.

Yiangou, Y. et al., "Vanilloid receptor 1 immunoreactivity in inflamed human bowel", *The Lancet*, vol. 357, pp. 1338-1339, Apr. 28, 2001.

Holzer, P., "TRPV1 and the gut: from a tasty receptor for a painful vanilloid to a key player in hyperalgesia", *European Journal of Pharmacology*, vol. 500, pp. 231-241, Aug. 24, 2004.

Hwang, S. et al., "Hot channels in airways: pharmacology of the vanilloid receptor", *Current Opinion in Pharmacology*, vol. 2, pp. 235-242, 2002.

Geppetti, P. et al., "The transient receptor potential vanilloid 1: Role in airway inflammation and disease", *European Journal of Pharmacology*, vol. 533, pp. 207-214, Feb. 7, 2006.

Birder, L. et al., "Altered urinary bladder function in mice lacking the vanilloid receptor TRPV1", *Nature Neuroscience*, vol. 5, No. 9, pp. 856-860, Sep. 2002.

Birder, L. et al., "Vanilloid receptor expression suggests a sensory role for urinary bladder epithelial cells", *PNAS*, vol. 98, No. 23, pp. 13396-13401, Nov. 6, 2001.

Southall, M. et al., "Activation of Epidermal Vanilloid Receptor-1 Induces Release of Proinflammatory Mediators in Human Keratinocytes", *The Journal of Pharmacology and Experimental Therapeutics*, vol. 304, No. 1, 217-222, Sep. 13, 2002.

Tominaga, M. et al., "The Cloned Capsaicin Receptor Integrates Multiple Pain-Producing Stimuli", *Neuron*, vol. 21, pp. 531-543, Sep. 1998.

Balaban, C. et al., "Type 1 vanilloid receptor expression by mammalian inner ear ganglion cells", *Hearing Research*, vol. 175, pp. 165-170, Oct. 21, 2002.

Scotland, R. et al., "Vanilloid Receptor TRPV1, Sensory C-Fibers, and Vascular Autoregulation: A Novel Mechanism Involved in Myogenic Constriction", *Circulation Research*, vol. 95, pp. 1027-1034, Nov. 12, 2004.

\* cited by examiner

COMPOUNDS, ISOMER THEREOF, OR PHARMACEUTICALLY ACCEPTABLE SALTS THEREOF AS VANILLOID RECEPTOR ANTAGONIST; AND PHARMACEUTICAL COMPOSITIONS CONTAINING THE SAME

CROSS REFERENCE TO RELATED APPLICATIONS

This application is a 35 USC §371 National Phase Entry Application from PCT/KR2006/000929, filed Mar. 15, 2006, and designating the United States. This application claims priority under 35 U.S.C. §119 based on Korean Patent Application No. 10-2005-0022986 filed Mar. 19, 2005 and claims the benefit of U.S. Provisional Application Ser. No. 60/663,269 filed Mar. 21, 2005, which are incorporated herein in their entireties.

TECHNICAL FIELD

The present invention relates to novel compounds, isomer thereof or pharmaceutically acceptable salts thereof as vanilloid receptor (Vanilloid Receptor 1; VR1; TRPV1) antagonist; and a pharmaceutical composition containing the same.

BACKGROUND ART

As diseases associated with the activity of vanilloid receptor (Nagy et al., 2004, Eur. J. Pharmacol. 500, 351-369) pain such as acute pain, chronic pain, neuropathic pain, postoperative pain, rheumatic arthrodynia, osteoarthritis pain, postherpetic neuralgia, neuralgia, headache, and migraine (Petersen et al., 2000, Pain, 88, pp 125-133; Walker et al., 2003, J. Pharmacol. Exp. Ther., 304, pp 56-62); nerve-related diseases such as neuropathies, HIV-related neuropathy, nerve injury, neurodegeneration, and stroke (Park et al., 1999, Arch. Pharm. Res. 22, pp 432-434; Kim et al., 2005, J. Neurosci. 25(3), pp 662-671); diabetic neuropathy (Kamei et al., 2001, Eur. J. Pharmacol. 422, pp 83-86); fecal urgency; irritable bowel syndrome (Chan et al., 2003, Lancet, 361, pp 385-391); inflammatory bowel disease (Yiangou et al., 2001, Lancet, 357, pp 1338-1339); disease of digestive organ such as stomach-duodenal ulcer and Crohn's disease (Holzer P, 2004, Eur. J. Pharm. 500, pp 231-241; Geppetti et al., 2004, Br. J. Pharmacol., 141, pp 1313-1320); disease of respiratory organ such as asthma, chronic obstructive pulmonary disease (Hwang et al., 2002, Curr Opin Pharm pp 235-242; Spina et al., 2002, Curr Opin Pharm pp 264-272); urinary incontinence (Birder et al., 2002, Nat. Neuroscience, 5, pp 856-860); urinary bladder hypersensitiveness (Birder et al., 2001, Proc. Natl. Acad. Sci. 98, pp 13396-13401); neurotic/allergic/inflammatory skin disease such as psoriasis, pruritus and prurigo (Southall et al., 2003, J. Pharmacol. Exp. Ther., 304, pp 217-222); irritation of skin, eye or mucous membrane (Tominaga et al., 1998, Neuron 21 pp 531-543); hyperacusis; tinnitus; vestibular hypersensitiveness (Balaban et al., 2003, Hear Res. 175, pp 165-70); cardiac disease such as inotropic ischemia etc. (Scotland et al., 2004, Circ. Res. 95, pp 1027-1034; Pan et al., 2004, Circulation, 110, pp 1826-1831) can be enumerated.

The vanilloid receptor (VR1) is the receptor for capsaicin (8-methyl-N-vanillyl-6-nonenamide), a pungent ingredient in hot peppers. The molecular cloning thereof was also reported in 1997 (Caterina et al., 1997, Nature 389, pp 816-824). This receptor is a non-selective cation channel composed of 6 transmembrane domains and belongs to the TRP channel family. Recently, it was named TRPV1. On the other hand, it is known that the vanilloid receptor is activated by stimuli such as capsaicin, resiniferatoxin, heat, acids, anandamide, lipid metabolites or the like; thus it plays a crucial role as a molecular integrator of physico-chemically noxious stimuli in mammals (Tominaga et al., 1998, Neuron 21 pp 531-543; Hwang et al., 2000, PNAS, 97, pp 6155-6160). Activation of the vanilloid receptor by endogenous/exogenous stimuli leads to not only transmission of noxious stimuli, but also liberation of neuropeptides such as substance P, CGRP (Calcitonin Gene-Related Peptide) and the like, thereby causing neurogenic inflammation. The vanilloid receptor is highly expressed in primary afferent sensory neurons. It is also reportedly expressed in various organs and tissues such as the bladder, kidney, lungs, intestines and skin, and in the central nervous system (CNS) including the brain and non-neuronal tissues (Mezey et al., 2000, PNAS, 97, pp 3655-3660; Stander et al., 2004, Exp. Dermatol. 13, pp 129-139; Cortright et al., 2001, BBRC, 281, pp 1183-1189). In particular, TRPV1 receptor knock-out mice exhibit a normal response to harmful physical stimuli, but show a reduction in pain responses and sensory sensitivity to thermal stimuli by vanilloid, and exhibit little hyperalgesia to thermal stimuli even in an inflammatory state (Caterina et al., 2000, Science 288, pp 306-313; Davis et al., 2000, Nature 405, pp 183-187; Karai et al., 2004, J. Clin. Invest., 113, pp 1344-1352). Lately, an additional role of the vanilloid receptor is also anticipated by presentation of possibility that the vanilloid receptor may be present in the form of a heteromultimer with TRPV3, another TRP channel (Smith et al., 2002, Nature, 418, pp 186-190).

As mentioned above, the vanilloid receptor knock-out mice exhibited reduced responses to thermal or noxious stimuli, thus raising the possibility that vanilloid receptor antagonists may be utilized for prevention or treatment of various pain conditions. Recently, this possibility is supported by the report that the well-known vanilloid receptor antagonist, capsazepine also decreases hyperalgesia caused by physical stimuli in models of inflammatory and neuropathic pain (Walker et al., 2003, JPET, 304, pp 56-62; Garcia-Martinez et al., 2002, Proc. Natl. Acad. Sci. 99, 2374-2379). In addition, treatment of the primary culture of afferent nerve cells with the vanilloid receptor agonist, capsaicin etc., results in damage to nerve functions and furthermore death of nerve cells. The vanilloid receptor antagonist exerts defense actions against such damage to nerve functions and nerve cell death (Holzer P, 1991, Pharmacological Reviews, 43, pp 143-201; Mezey et al., 2000, PNAS, 97, 3655-3660). The vanilloid receptor is expressed in all regions of the gastrointestinal tract, for example, ganglia of tensor, tunica muscularis, mucosa and epithelial cells. In particular, the vanilloid receptor is highly expressed in inflammatory disorders of the colon and ileum.

In addition, activation of the vanilloid receptor stimulates sensory nerves, which in turn causes release of neuropeptides which are known to play a critical role in pathogenesis of bowel disorders. The role of the vanilloid receptor in development of gastrointestinal disorders is well elucidated and documented in recent scientific papers and journals, for example, Holzer P, 2004, Eur. J. Pharm. 500, pp 231-241; Geppetti et al., 2004, Br. J. Pharmacol., 141, pp 1313-1320. According to such references, it seems that the vanilloid receptor antagonists will be effective for prevention or treatment of gastrointestinal diseases such as gastro-esophageal reflux disease (GERD) and gastroduodenal ulcer (DU). It has been reported that the number of sensory nerves expressing the vanilloid receptor is increased in patients suffering from irritable bowel syndromes and such increased expression of the vanilloid receptor is known to be involved in the development of the disease (Chan et al., 2003, Lancet, 361, pp 385-391). Other investigations showed that expression of the vanilloid receptor is significantly increased in patients suffering from inflammatory bowel disorders. Taken together, it appears that the vanilloid receptor antagonist may also be therapeutically effective for such bowel disorders (Yiangou et al., 2001, Lancet, 357, pp 1338-1339). The vanilloid receptor-expressing afferent nerves are abundantly distributed in airway mucosa. Bronchial hypersensitivity is very similar to hyperalgesia, and protons and lipoxygenase products, known as endogenous ligands for the vanilloid receptor, are well known as crucial factors responsible for development of asthma and chronic obstructive pulmonary diseases (Hwang et al., 2002, Curr. Opin. Pharm. pp 235-242; Spina et al., 2002, Curr. Opin. Pharm. pp 264-272). Further, it has been reported that air-polluting substances, which are a kind of asthma-causing substances, i.e., particulate matter specifically acts on the vanilloid receptor and such action is inhibited by capsazepine, thus suggesting the possible applicability of vanilloid receptor antagonists to respiratory diseases (Veronesi et al., 2001, NeuroToxicology, 22, pp 795-810). Urinary bladder hypersensitiveness and urinary incontinence are caused by various central/peripheral nerve disorders or injury, and capsaicin-responsive sensory nerves play an important role in bladder function control and inflammation. In addition, immunoreactivity of the vanilloid receptor was reported in urinary bladder epithelium (urothelium) in rats and it was found that bladder overactivity induced by capsaicin was due to stimulation of vanilloid receptors present in nerve fibers, or various transmitters which are released by vanilloid receptors (Birder et al., 2001, Proc. Natl. Acad. Sci. 98, pp 13396-13401). Further, VR1 (TRPV1)-/- mice are anatomically normal, but exhibit non-excretory bladder contractions by low contractile force, as compared to normal mice, thus indicating that the vanilloid receptor affects functions of the bladder (Birder et al., 2002, Nat. Neuroscience, 5, pp 856-860). Some of vanilloid agonists are recently under development as therapeutics for treating bladder diseases. Vanilloid receptors are distributed in human epidermal keratinocytes as well as in primary afferent sensory nerves (Denda et al., 2001, Biochem. Biophys. Res. Commun., 285, pp 1250-1252; Inoue et al., 2002, Biochem. Biophys. Res. Commun., 291, pp 124-129), and are then involved in transmission of various noxious stimuli and pains such as skin irritation and pruritus, thereby having close correlation with etiology of dermatological diseases and disorders such as skin inflammation, due to neurogenic/non-neurogenic factors. This is supported by the report that the vanilloid receptor antagonist, capsazepine inhibits inflammatory factors in human skin cells (Southall et al., 2003, J. Pharmacol. Exp. Ther., 304, pp 217-222).

Based on the above-mentioned information, development of various vanilloid receptor antagonists is under way, and some patents and patent applications relating to vanilloid receptor antagonists under development were recently published, in which the above mentioned information is described well (Rami et al., 2004, Drug Discovery Today: Therapeutic Strategies, 1, pp 97-104).

As a result of extensive and intensive studies based on the theoretical background discussed above, the present inventors have synthesized novel compounds having antagonistic activity by selective action on a vanilloid receptor and thus completed the present invention. Surprisingly, it has been identified that compounds having a dibenzyl urea, dibenzylamide or dibenzylcinnamoyl structure and carrying a C2-C5 alkenyl or C2-C5 alkynyl as well as an amine-containing substituent on one of their phenyl ring are particularly active modulators of the vanilloid receptor.

Therefore, it is an object of the present invention to provide novel compounds useful as a potent antagonist for a vanilloid receptor, isomer thereof and pharmaceutically acceptable salts thereof; and a pharmaceutical composition comprising the same.

DISCLOSURE OF THE INVENTION

The present invention provides a novel compound of the following formula (I), an isomer thereof, or a pharmaceutically acceptable salt thereof; and a pharmaceutical composition containing the same.

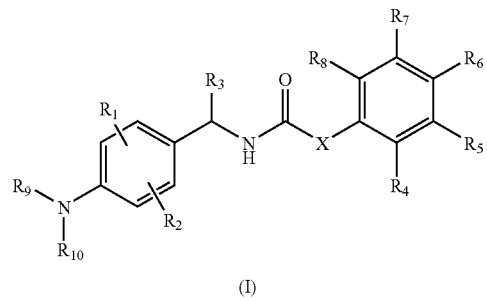

[Formula I]

(I)

wherein,

X is $NHCH_2$, $CR_{11}=CR_{12}$, NH, $CHR_{11}CHR_{12}$, or $C\equiv C$, wherein, $R_{11}$ and $R_{12}$ are independently hydrogen, halogen, C1-C5 alkyl, C1-C5 alkoxy, halo (C1-C5) alkyl, or phenyl;

$R_1$ is C2-C5 alkenyl, or C2-C5 alkynyl;

$R_2$ is hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl;

$R_3$ is hydrogen, C1-C5 alkyl, C1-C5 alkoxy, or halo (C1-C5) alkyl;

$R_4$, $R_5$, $R_6$, $R_7$, and $R_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkylcarbonyl, C1-C5 alkoxycarbonyl, hydroxy, C2-C5 alkenyloxy, C1-C5 alkoxy (C1-C5) alkoxy, C1-C5 alkoxy (C1-C5) alkoxy (C1-C5) alkyl, C1-C3 alkylpiperazinyl, piperazinyl (C1-C5) alkoxy, piperidinyl (C1-C5) alkoxy, C1-C5 alkoxy (C1-C5) alkylamino, C1-C7 alkylamino, morpholinyl, morpholinyl (C1-C5) alkyloxy, tetrahydropyranyloxy, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, C1-C5 alkoxycarbonyl, or piperidinyloxy, unsubstituted or substituted with C1-C5 alkoxycarbonyl; and $R_9$ and $R_{10}$ are independently hydrogen, $-SO_2R_{13}$, $-SOR_{13}$, C1-C5 alkyl, C1-C5 alkoxy, halo (C1-C5) alkyl, C2-C5 alkenyl, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl, and $R_{13}$ is hydrogen, amino, C1-C5 alkyl, C2-C5 alkenyl, C1-C5 alkoxy, halo (C1-C5) alkyl, trifluoromethyl, phenyl, or phenyl (C1-C3) alkyl.

One preferred aspect of the present invention is a compound of the formula (I), an isomer thereof, or a pharmaceutically acceptable salt thereof;
wherein,
X is $NHCH_2$, $CR_{11}$=$CR_{12}$, or C≡C, wherein, $R_{11}$ and $R_{12}$ are independently hydrogen, halogen, C1-C5 alkyl, or phenyl;

$R_1$ is C2-C5 alkenyl or C2-C5 alkynyl;

$R_2$ is hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl;

$R_3$ is hydrogen, C1-C5 alkyl, C1-C5 alkoxy, or halo (C1-C5) alkyl;

$R_4$, $R_5$, $R_6$, $R_7$, and $R_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkylcarbonyl, C1-C5 alkoxycarbonyl, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl; and $R_9$ and $R_{10}$ are independently hydrogen, $-SO_2R_{13}$, $-SOR_{13}$, C1-C5 alkyl, C1-C5 alkoxy, halo (C1-C5) alkyl, C2-C5 alkenyl, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl, and $R_{13}$ is hydrogen, amino, C1-C5 alkyl, C2-C5 alkenyl, C1-C5 alkoxy, halo (C1-C5) alkyl, trifluoromethyl, phenyl, or phenyl (C1-C3) alkyl.

Another aspect of the present invention is a compound according to the above formula (I), an isomer, or a pharmaceutically acceptable salt thereof;
wherein,
X is $NHCH_2$, $CR_{11}$=$CR_{12}$, or C≡C, wherein, $R_{11}$ and $R_{12}$ are independently hydrogen, halogen, C1-C5 alkyl, or phenyl;

$R_1$ is ethenyl, ethynyl, propenyl, or propynyl;

$R_2$ is hydrogen, fluoro, chloro, bromo, iodo, nitro, cyano, methyl, ethyl, propyl, isopropyl, butyl, isobutyl, methoxy, ethoxy, trifluoromethyl, carboxy, methoxycarbonyl, or phenyl;

$R_3$ is hydrogen, methyl, or ethyl;

$R_4$, $R_5$, $R_6$, $R_7$, and $R_8$ are independently, carboxy, methyl, ethyl, propyl, isopropyl, t-butyl, nitro, ethenyl, ethynyl, methylthio, trifluoromethyl, methoxycarbonyl, or halogen; and $R_9$ and $R_{10}$ are independently hydrogen, $-SO_2R_{13}$, $-SOR_{13}$, C1-C5 alkyl, C1-C5 alkoxy, halo (C1-C5) alkyl, C2-C5 alkenyl, phenyl, phenyl (C1-C3) alkyl, or C1-C3 alkoxyphenyl, wherein, $R_{13}$ is hydrogen, amino, C1-C5 alkyl, C2-C5 alkenyl, trifluoromethyl, phenyl, or benzyl.

One preferred embodiment of the present invention relates to the above described compounds of formula (I) having one or more of the following features:
compounds wherein $R_9$ is $-SO_2R_{13}$ and $R_{10}$ is hydrogen, wherein $R_9$ is more preferably methanesulfonyl, ethanesulfonyl, trifluoromethanesulfonyl, or ethenesulfonyl, and most preferably methanesulfonyl;
compounds wherein $R_6$ is C1-C5 alkyl, halo (C1-C5) alkyl, C1-C5 alkylthio, or halogen; wherein those compounds are more preferred in which $R_6$ is halo (C1-C3) alkyl, isopropyl or t-butyl and wherein compounds in which $R_6$ is isopropyl or t-butyl are most preferred;
compounds wherein $R_3$ is hydrogen or C1-C5 alkyl; wherein compounds are most preferred in which $R_3$ is hydrogen or methyl;
compounds wherein $R_4$, $R_5$, $R_7$, and $R_8$ are preferably independently hydrogen, C1-C5 alkyl, halo (C1-C5) alkyl, C1-C5 alkylthio, or hydrogen; wherein those compounds are most preferred in which $R_5$, $R_7$, and $R_8$ are hydrogen;
compounds wherein $R_1$ is ethenyl, ethynyl, propenyl, or propynyl, and most preferably ethenyl or ethynyl; or
compounds wherein $R_2$ is hydrogen, fluoro, chloro, bromo, iodo, nitro, cyano, methyl, ethyl, propyl, isopropyl, butyl, isobutyl, methoxy, ethoxy, trifluoromethyl, carboxyl, methoxycarbonyl, or phenyl; and most preferably $R_2$ is hydrogen, fluoro, chloro, bromo, iodo, or methyl.

Another preferred embodiment of the inventions are compounds of the above formula (I), in which
X is $NHCH_2$, $CH_2$=$CH_2$, or C≡C;
$R_1$ is ethenyl or ethynyl;
$R_2$ is hydrogen, fluoro, chloro, bromo, iodo, nitro, cyano, methyl, ethyl, propyl, isopropyl, butyl, isobutyl, methoxy, ethoxy, trifluoromethyl, carboxy, methoxycarbonyl, or phenyl;
$R_3$ is hydrogen, methyl, or ethyl;
$R_4$, $R_5$, $R_7$, $R_8$, and $R_{10}$ are hydrogen;
$R_6$ is chloro, isopropyl or t-butyl and particularly preferably isopropyl or tert butyl; and
$R_9$ is methanesulfonyl, ethanesulfonyl, trifluoromethanesulfonyl, or ethenesulfonyl.

A particular preferred embodiment of the present invention are compounds of formula (Ia)

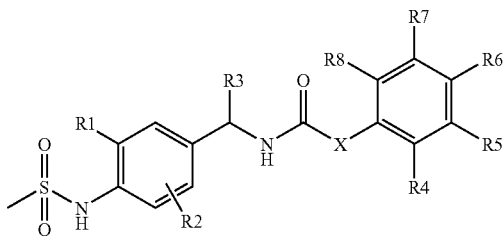

(Ia)

wherein,
X is $NHCH_2$ or $CH_2$=$CH_2$;
$R_1$ is ethenyl or ethynyl;
$R_2$ is hydrogen, fluoro, chloro, bromo, iodo, nitro, cyano, methyl, ethyl, propyl, isopropyl, butyl, isobutyl, methoxy, ethoxy, trifluoromethyl, carboxy, methoxycarbonyl, or phenyl;
$R_3$ is hydrogen, methyl, or ethyl;
$R_4$, $R_5$, $R_7$, and $R_8$ are hydrogen; and
$R_6$ is isopropyl or t-butyl.

Another preferred embodiment of the present invention relates to a compound of formula I, above, an isomer thereof, or a pharmaceutically acceptable salt thereof
wherein,
X is $NHCH_2$, $CR_{11}=CR_{12}$, NH, $CHR_{11}CHR_{12}$ or $C\equiv C$, wherein, $R_{11}$ and $R_{12}$ are independently hydrogen, fluoro, or methyl;
$R_1$ is ethenyl, ethynyl, propenyl, or propynyl;
$R_2$ is hydrogen, fluoro, chloro, bromo, iodo, nitro, cyano, methyl, ethyl, propyl, isopropyl, butyl, isobutyl, methoxy, ethoxy, ethynyl, ethenyl, carboxy, or methoxycarbonyl;
$R_3$ is hydrogen, methyl, or ethyl;
$R_4$, $R_5$, $R_7$, and $R_8$ are independently hydrogen, fluoro, carboxy, methyl, ethyl, propyl, isopropyl, t-butyl, nitro, ethenyl, ethynyl, trifluoromethyl, methoxycarbonyl, halogen, methoxyethoxy, methoxyethoxymethyl, methylpiperazinyl, methoxyethylamino, hydroxy, methoxy, allyloxy, isohexylamino, isobutylamino, isopropylamino, morpholinyl, morpholinylethoxy, or tetrahydropyranyloxy;
$R_6$ is C3-C5 alkyl or halo (C1-C3) alkyl and particularly preferably isopropyl or t-butyl; and
$R_9$ and $R_{10}$ are independently hydrogen or methanesulfonyl.

Another preferred embodiment of the present invention are compounds of the above formula I, wherein,
X is $NHCH_2$, $CR_{11}=CR_{12}$, $CHR_{11}CHR_{12}$ or $C\equiv C$, wherein, $R_{11}$ is hydrogen or methyl and $R_{12}$ is hydrogen;
$R_1$ is ethenyl or ethynyl;
$R_2$ is hydrogen, fluoro, methyl, or chloro;
$R_3$ is hydrogen or methyl;
$R_4$, is hydrogen, fluoro, methoxymethoxy, methoxyethoxy, methoxypropoxy, methoxy, methoxyethylamino, allyloxy, or tetrahydropyranyloxy;
R5, R7 and R8 are hydrogen or fluoro;
$R_6$ is C3-C5 alkyl or halo (C1-C3) alkyl, and particularly preferably isopropyl or t-butyl; and
$R_9$ is hydrogen and $R_{10}$ represents methanesulfonyl.

Another preferred embodiment of the present invention are compounds of the above formula I, wherein,
X is $CR_{11}=CR_{12}$, wherein $R_{11}$ is hydrogen or methyl and $R_{12}$ is hydrogen;
$R_1$ is ethenyl or ethynyl;
$R_2$ is hydrogen, fluoro, methyl, or chloro;
$R_3$ is hydrogen or methyl;
$R_4$ is hydrogen, fluoro, methoxymethoxy, methoxyethoxy, methoxypropoxy, methoxy, methoxyethylamino, allyloxy, or tetrahydropyranyloxy;
R5, R7 and R8 are hydrogen or fluoro;
$R_6$ is C3-C5 alkyl or halo (C1-C3) alkyl and particularly preferably isopropyl or t-butyl; and
$R_9$ is hydrogen and $R_{10}$ represents methanesulfonyl.

Another preferred embodiment of the present invention are compounds of the above formula I, wherein,
X is $C\equiv C$;
$R_1$ is ethenyl or ethynyl;
$R_2$ is hydrogen, fluoro, methyl, or chloro;
$R_3$ is hydrogen or methyl;
$R_4$ is hydrogen, fluoro, methoxymethoxy, methoxyethoxy, methoxypropoxy, methoxy, methoxyethylamino, allyloxy, or tetrahydropyranyloxy;
R5, R7 and R8 are hydrogen or fluoro;
$R_6$ is C3-C5 alkyl or halo (C1-C3) alkyl and particularly preferably isopropyl or t-butyl; and
$R_9$ is hydrogen and $R_{10}$ represents methanesulfonyl.

Another preferred embodiment of the present invention are compounds of the above formula I, wherein
X is $NHCH_2$,
$R_1$ is ethenyl or ethynyl;
$R_2$ is hydrogen, fluoro, methyl, or chloro;
$R_3$ is hydrogen or methyl;
$R_4$ is hydrogen, fluoro, methoxymethoxy, methoxyethoxy, methoxypropoxy, methoxy, methoxyethylamino, allyloxy, or tetrahydropyranyloxy and particularly preferably hydrogen or fluoro;
R5, R7 and R8 are hydrogen or fluoro;
$R_6$ is C3-C5 alkyl or halo (C1-C3) alkyl and particularly preferably isopropyl or t-butyl; and
$R_9$ is hydrogen and $R_{10}$ represents methanesulfonyl.

Another preferred embodiment of the present invention are compounds of the above formula I, wherein,
X is $CHR_{11}CHR_{12}$, wherein, $R_{11}$ is hydrogen or methyl and $R_{12}$ is hydrogen;
$R_1$ is ethenyl or ethynyl;
$R_2$ is hydrogen, fluoro, methyl, or chloro;
$R_3$ is hydrogen or methyl;
$R_4$ is hydrogen, fluoro, methoxymethoxy, methoxyethoxy, methoxypropoxy, methoxy, methoxyethylamino, allyloxy, or tetrahydropyranyloxy and particularly preferably hydrogen, fluoro or tetrahydropyranyloxy;
R5, R7 and R8 are hydrogen or fluoro;
$R_6$ is C3-C5 alkyl or halo (C1-C3) alkyl and particularly preferably isopropyl or t-butyl; and
$R_9$ is hydrogen and $R_{10}$ represents methanesulfonyl.

Another preferred embodiment of the present invention are compounds of the above formula I, wherein,
X is NH,
$R_1$ is ethenyl or ethynyl;
$R_2$ is hydrogen, fluoro, methyl, or chloro;
$R_3$ is methyl;
$R_4$ is hydrogen, fluoro, methoxymethoxy, methoxyethoxy, methoxypropoxy, methoxy, methoxyethylamino, allyloxy, or tetrahydropyranyloxy and particularly preferably hydrogen or fluoro;
R5, R7 and R8 are hydrogen or fluoro;
$R_6$ is C3-C5 alkyl or halo (C1-C3) alkyl and particularly preferably isopropyl or t-butyl; and
$R_9$ is hydrogen and $R_{10}$ represents methanesulfonyl.

One embodiment of the present invention relates to compounds of formula I as defined further above, wherein X is CHR11—CHR12. These compounds have the general formula (Ib).

(Ib)

wherein,
$R_{11}$ and $R_{12}$ are independently hydrogen, halogen, C1-C5 alkyl, C1-C5 alkoxy, halo (C1-C5) alkyl, or phenyl;
$R_1$ is C2-C5 alkenyl or C2-C5 alkynyl;
$R_2$ is hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl;

$R_3$ is hydrogen, C1-C5 alkyl, C1-C5 alkoxy, or halo (C1-C5) alkyl;

$R_4$, $R_5$, $R_6$, $R_7$, and $R_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkylcarbonyl, C1-C5 alkoxycarbonyl, hydroxy, C2-C5 alkenyloxy, C1-C5 alkoxy (C1-C5) alkoxy, C1-C5 alkoxy (C1-C5) alkoxy (C1-C5) alkyl, C1-C3 alkylpiperazinyl, piperazinyl (C1-C5) alkoxy, piperidinyl (C1-C5) alkoxy, C1-C5 alkoxy (C1-C5) alkylamino, C1-C7 alkylamino, morpholinyl, morpholinyl (C1-C5) alkyloxy, tetrahydropyranyloxy, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, C1-C5 alkoxycarbonyl, or piperidinyloxy unsubstituted or substituted with C1-C5 alkoxycarbonyl; and wherein $R_6$ is preferably C3-C5 alkyl or halo (C1-C3) alkyl, and particularly preferably isopropyl or t-butyl; and $R_9$ and $R_{10}$ are independently hydrogen, —$SO_2R_{13}$, —$SOR_{13}$, C1-C5 alkyl, C1-C5 alkoxy, halo (C1-C5) alkyl, C2-C5 alkenyl, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl, and $R_{13}$ is hydrogen, amino, C1-C5 alkyl, C2-C5 alkenyl, C1-C5 alkoxy, halo (C1-C5) alkyl, trifluoromethyl, phenyl, or phenyl (C1-C3) alkyl.

Preferably, in the above figure (Ib), $R_{11}$ and $R_{12}$ are methyl or hydrogen;
$R_1$ is ethenyl or ethynyl;
$R_2$ is hydrogen, fluoro, chloro, bromo, iodo, nitro, cyano, methyl, ethyl, propyl, isopropyl, butyl, isobutyl, methoxy, ethoxy, trifluoromethyl, carboxy, or methoxycarbonyl;
$R_3$ is hydrogen, methyl, or ethyl;
$R_4$, $R_5$, $R_7$, and $R_8$ are independently hydrogen, fluoro, carboxy, methyl, ethyl, propyl, isopropyl, t-butyl, nitro, ethenyl, ethynyl, trifluoromethyl, methoxycarbonyl, halogen, methoxyethoxy, methoxyethoxymethyl, methylpiperazinyl, methoxyethylamino, hydroxy, methoxy, allyloxy, isohexylamino, isobutylamino, isopropylamino, morpholinyl, morpholinylethoxy, or tetrahydropyranyloxy; and
$R_6$ is isopropyl, t-butyl, or halo (C1-C3) alkyl and particularly preferably isopropyl or t-butyl.

Even more preferably, in the above figure (Ib),
$R_{11}$ is hydrogen or methyl, and $R_{12}$ is hydrogen;
$R_1$ is ethenyl or ethynyl;
$R_2$ is hydrogen, fluoro, chloro, or methyl;
$R_4$ is hydrogen, fluoro, methoxymethoxy, methoxyethoxy, methoxypropoxy, methoxy, methoxyethylamino, allyloxy, or tetrahydropyranyloxy;
$R_5$, $R_7$ and $R_8$ are hydrogen or fluoro;
$R_6$ is tert-butyl;
$R_9$ is hydrogen; and
$R_{10}$ represents methanesulfonyl.

According to one important aspect of the present invention, in compounds of the above formula (I) and (Ib), $R_9$ is hydrogen, $R_{10}$ is methanesulfonyl and $R_1$ is bound to the phenyl ring in ortho-position to the methanesulfonylamino group. Those preferred compounds have the general formula (Ic).

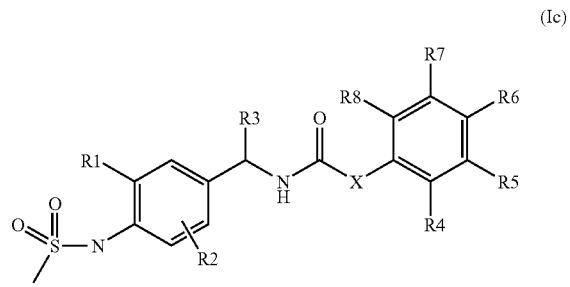

wherein $R_1$, $R_2$, $R_3$, $R_4$, $R_5$, $R_6$, $R_7$, $R_8$ and X have the meaning according to the various embodiments defined above, and wherein the description of the various preferred embodiments and features of the compounds of formula I and (Ib) do also apply to the compounds of formula (Ic).

According to one aspect of the present invention, in compounds of the above formula (I) and (Ib), $R_9$ is hydrogen, $R_{10}$ is methanesulfonyl and $R_1$ and $R_2$ are both bound to the phenyl ring in ortho-position to the methanesulfonylamino group. Those preferred compounds have the general formula (Id).

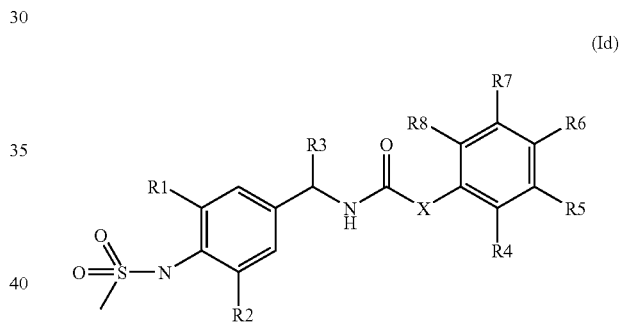

wherein $R_1$, $R_2$, $R_3$, $R_4$, $R_5$, $R_6$, $R_7$, $R_8$ and X have the meaning according to the various embodiments defined above, and wherein the description of the various preferred embodiments and features of the compounds of formula I and (Ib) do also apply to the compounds of formula (Id).

In the compounds of formula (Ic) or (Id) most preferably;
X is $CHR_{11}CHR_{12}$ or X is selected from $NHCH_2$, $CR_{11}=CR_{12}$ and $C\equiv C$;
$R_1$ is ethenyl or ethynyl;
$R_2$ is hydrogen, fluoro, chloro, or methyl;
$R_3$ is hydrogen or methyl;
$R_4$ is hydrogen, fluoro, methoxymethoxy, methoxyethoxy, methoxypropoxy, methoxy, methoxyethylamino, allyloxy, or tetrahydropyranyloxy;
$R_5$, $R_7$ and $R_8$ are hydrogen or fluoro; and
$R_6$ is halo (C1-C3) alkyl, isopropyl or, preferably, tert-butyl.

Preferred examples of compounds according to the invention are selected from the group consisting of;
N-{4-[3-(4-t-butylbenzyl)ureidomethyl]-2-vinylphenyl}methanesulfonamide,
N-{4-[3-(4-t-butylbenzyl)ureidomethyl]-2-fluoro-6-vinylphenyl}methanesulfonamide, N-{4-[3-(4-t-butylbenzyl)ureidomethyl]-2-ethynyl-6-fluorophenyl}methanesulfonamide,
N-{4-[3-(4-t-butylbenzyl)ureidomethyl]-5-chloro-2-vinylphenyl}methanesulfonamide,
N-{4-[3-(4-t-butylbenzyl)ureidomethyl]-5-chloro-2-ethynylphenyl}methane sulfonamide,
N-(4-{1-(R)-[3-(4-t-butylbenzyl)ureido]ethyl}-2-vinylphenyl)methanesulfonamide,
(R)—N-(4-{1-[3-(4-t-butyl-benzyl)-ureido]-ethyl}-2-fluoro-6-vinyl-phenyl)-methanesulfonamide,
N-{4-[3-(4-t-butyl-benzyl)-ureidomethyl]-2-methyl-6-vinyl-phenyl}-methanesulfonamide,
N-{4-[3-(4-t-butyl-benzyl)-ureidomethyl]-2-chloro-6-vinyl-phenyl}-methanesulfonamide,
3-(4-t-butylphenyl)propynoic acid 3-fluoro-4-methanesulfonylamino-5-vinylbenzylamide,
3-(4-t-butylphenyl)propynoic acid [1-(3-fluoro-4-methanesulfonylamino-5-vinylphenyl)ethyl]amide,
3-(4-t-butylphenyl)-N-[1-(R)-(4-methanesulfonylamino-3-vinyl phenyl)ethyl]acrylamide,
3-(4-t-butylphenyl)-N-(3-fluoro-4-methanesulfonylamino-5-vinylbenzyl)acryl amide,
3-(4-t-butylphenyl)-N-(3-fluoro-5-ethynyl-4-methanesulfonyl amino-benzyl)acrylamide,
3-(4-t-butylphenyl)-N-(4-methanesulfonylamino-3-vinyl-benzyl)acrylamide,
3-(4-trifluoromethylphenyl)-N-(4-methanesulfonylamino-3-vinylbenzyl)acryl amide,
3-(4-t-butylphenyl)-N-(3-chloro-4-methanesulfonylamino-5-vinylbenzyl)acrylamide,
3-(4-t-butyl-2-morpholin-4-yl-phenyl)-N-(3-fluoro-4-methanesulfonylamino-5-vinylbenzyl)acrylamide,
3-(4-t-butyl-2-methoxyethoxy-phenyl)-N-(3-fluoro-4-methanesulfonylamino-5-vinylbenzyl)acrylamide,
3-[4-t-butyl-2-(2-methoxyethylamino)phenyl]-N-(3-fluoro-4-methanesulfonylamino-5-vinylbenzyl)acrylamide,
3-(4-t-butyl-2-methoxyphenyl)-N-(3-fluoro-4-methanesulfonylamino-5-vinyl-benzyl)acrylamide,
3-(2-allyloxy-4-t-butylphenyl)-N-(3-fluoro-4-methanesulfonylamino-5-vinylbenzyl)acrylamide,
3-[4-t-butyl-2-(3-methylbutylamino)phenyl]-N-(3-fluoro-4-methanesulfonylamino-5-vinylbenzyl)acrylamide,
3-(4-t-butyl-2-isopropylaminophenyl)-N-(3-fluoro-4-methanesulfonylamino-5-vinylbenzyl)acrylamide,
3-(4-t-butylphenyl)-N-[1-(3-fluoro-4-methanesulfonylamino-5-vinylphenyl) ethyl]propionamide,
3-(4-t-butylphenyl)-N-[1-(3-fluoro-4-methanesulfonylamino-5-vinylphenyl)ethyl]acrylamide,
3-(4-t-butylphenyl)-N-(3-fluoro-4-methanesulfonylamino-5-vinylbenzyl)-2-methylacrylamide,
3-(4-t-butylphenyl)-2-fluoro-N-(3-fluoro-4-methanesulfonylamino-5-vinylbenzyl)acrylamide,
3-[4-t-butyl-2-(tetrahydropyran-4-yloxy)phenyl]-N-(3-fluoro-4-methanesulfonylamino-5-vinylbenzyl)acrylamide,
3-[4-t-butyl-2-(tetrahydropyran-4-yloxy)phenyl]-N-(3-fluoro-4-methanesulfonylamino-5-vinylbenzyl)propionamide,
3-(4-t-butylphenyl)-N-[1-(4-methanesulfonylamino-3-vinylphenyl)ethyl]-2-methylacrylamide,
3-(4-t-butylphenyl)-N-(3-fluoro-4-methanesulfonylamino-5-vinylbenzyl)-2-methylpropionamide,
3-[4-(tert-butyl)phenyl]-[N-4-(methanesulfonylamino)-3-vinylbenzyl]propionamide,
3-[4-(tert-butyl)phenyl]-[N-3-fluoro-4-(methanesulfonylamino)-5-vinylbenzyl]propionamide,
3-(4-t-butyl-phenyl)-N-(3-ethynyl-5-fluoro-4-methanesulfonylamino-benzyl)-propionamide,
N-(4-{1-[3-(4-t-butylphenyl)ureido]ethyl}-2-vinylphenyl)methanesulfonamide,
N-(4-{1-[3-(4-t-butylphenyl)ureido]ethyl}-2-ethynylphenyl)methanesulfonamide,
N-{4-[3-(4-t-butylphenyl)ureidomethyl]-2-fluoro-6-vinylphenyl}methanesulfonamide, and
Ethenesulfonic acid (4-{1-[3-(4-t-butylphenyl)ureido]ethyl}-2-vinylphenyl)amide.

Particularly preferred compounds according to the present invention are
(R)—N-(4-{1-[3-(4-t-butyl-benzyl)-ureido]-ethyl}-2-fluoro-6-vinyl-phenyl)-methanesulfonamide,
3-(4-t-butylphenyl)-N-[1-(R)-(4-methanesulfonylamino-3-vinyl phenyl)ethyl]acrylamide,
3-(4-t-butylphenyl)-N-(3-fluoro-4-methanesulfonylamino-5-vinylbenzyl)acryl amide,
3-(4-t-butylphenyl)-N-(3-fluoro-5-ethynyl-4-methanesulfonyl amino-benzyl)acrylamide,
(R)-3-(4-t-butylphenyl)-N-[1-(3-fluoro-4-methanesulfonylamino-5-vinylphenyl)ethyl]propionamide,
3-(4-t-butylphenyl)-N-(3-fluoro-4-methanesulfonylamino-5-vinylbenzyl)-2-methylacrylamide,
3-[4-t-butyl-2-(tetrahydropyran-4-yloxy)phenyl]-N-(3-fluoro-4-methanesulfonylamino-5-vinylbenzyl)propionamide,
(R)-3-(4-t-butylphenyl)-N-[1-(4-methanesulfonylamino-3-vinylphenyl)ethyl]-2-methylacrylamide,
N-{4-[3-(4-t-butylbenzyl)ureidomethyl]-2-fluoro-6-vinylphenyl}methanesulfonamide,
N-{4-[3-(4-t-butylbenzyl)ureidomethyl]-2-ethynyl-6-fluorophenyl}methanesulfonamide,
3-(4-tert-Butylphenyl)propynoic acid 3-fluoro-4-methanesulfonylamino-5-vinylbenzylamide,
3-(4-t-butylphenyl)-N-(4-methanesulfonylamino-3-vinylbenzyl)acrylamide,
3-[4-tert-Butyl-2-(2-methoxy-ethoxy)-phenyl]-N-(3-fluoro-4-methanesulfonylamino-5-vinyl-benzyl)-acrylamide,
3-[4-tert-Butyl-2-(2-methoxyethylamino)phenyl]-N-(3-fluoro-4-methanesulfonylamino-5-vinylbenzyl)acrylamide,
3-(4-tert-Butyl-2-methoxyphenyl)-N-(3-fluoro-4-methanesulfonylamino-5-vinyl-benzyl)acrylamide,
3-(2-Allyloxy-4-tert-butylphenyl)-N-(3-fluoro-4-methanesulfonylamino-5-vinylbenzyl)acrylamide,
(R)-3-(4-tert-Butylphenyl)-N-[1-(3-fluoro-4-methanesulfonylamino-5-vinylphenyl)ethyl]acrylamide,
3-(4-tert-Butylphenyl)-N-(3-fluoro-4-methanesulfonylamino-5-vinylbenzyl)-2-methylpropionamide,
3-[4-(tert-butyl)phenyl]-[N-4-(methanesulfonylamino)]-3-vinylbenzyl]propionamide,
N-(4-{1-(R)-[3-(4-t-butylbenzyl)ureido]ethyl}-2-vinylphenyl)methanesulfonamide,
3-[4-(tert-butyl)phenyl]-N-[3-fluoro-4-(methanesulfonylamino)-5-vinylbenzyl]propionamide, and
(R)—N-(4-{1-[3-(4-tert-Butylphenyl)ureido]ethyl}-2-vinylphenyl)methanesulfonamide.

The structures of the Example compounds of the present invention are shown in Table 1.

TABLE 1

| Example No. | Structure |
| --- | --- |
| 1 | 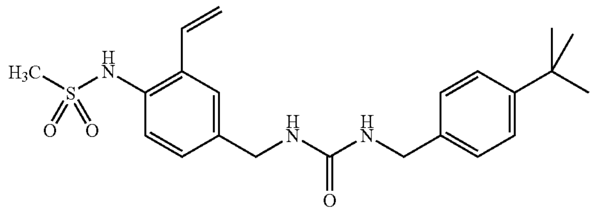 |
| 2 | 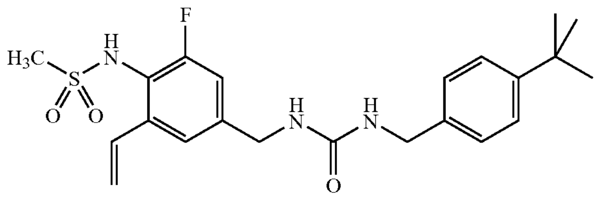 |
| 3 | 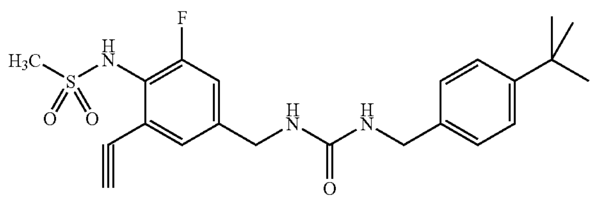 |
| 4 | 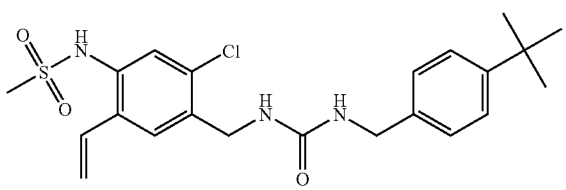 |
| 5 | 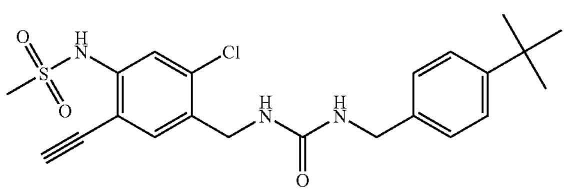 |
| 6 | 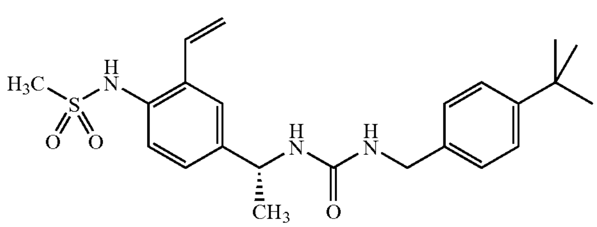 |
| 7 | 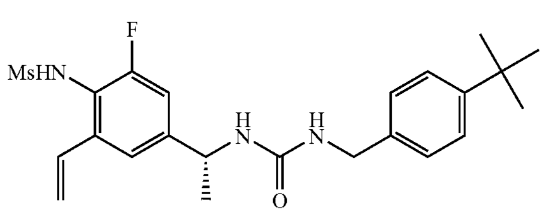 |

TABLE 1-continued

| Example No. | Structure |
|---|---|
| 8 | (structure) |
| 9 | (structure) |
| 10 | (structure) |
| 11 | (structure) |
| 12 | (structure) |
| 13 | (structure) |
| 14 | (structure) |

TABLE 1-continued

| Example No. | Structure |
|---|---|
| 15 | *(structure: N-methylsulfonamide, 2-fluoro, 6-vinyl benzyl cinnamide with 4-tert-butylphenyl)* |
| 16 | *(structure: N-methylsulfonamide, 2-fluoro, 6-ethynyl benzyl cinnamide with 4-tert-butylphenyl)* |
| 17 | *(structure: N-methylsulfonamide, 3-vinyl benzyl cinnamide with 4-tert-butylphenyl)* |
| 18 | *(structure: N-methylsulfonamide, 3-vinyl benzyl cinnamide with 4-CF₃-phenyl)* |
| 19 | *(structure: N-methylsulfonamide, 3-vinyl benzyl cinnamide with 4-SMe-phenyl)* |
| 20 | *(structure: N-methylsulfonamide, 2-methyl, 6-vinyl benzyl cinnamide with 4-tert-butylphenyl)* |
| 21 | *(structure: N-methylsulfonamide, 2-chloro, 6-vinyl benzyl cinnamide with 4-tert-butylphenyl)* |

TABLE 1-continued

| Example No. | Structure |
| --- | --- |
| 22 | 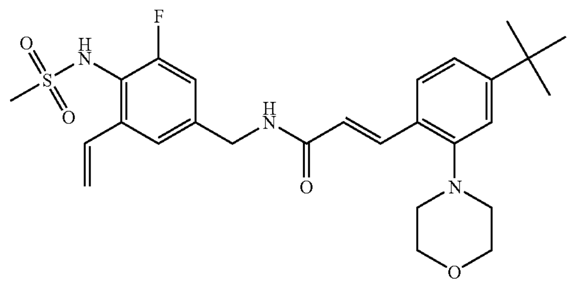 |
| 23 | 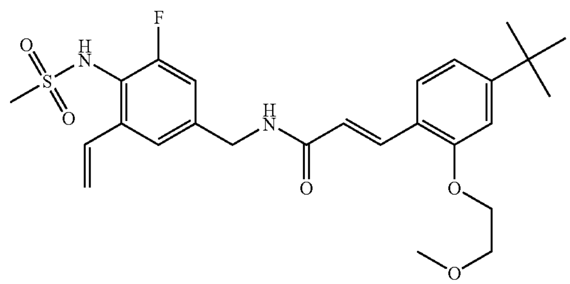 |
| 24 | 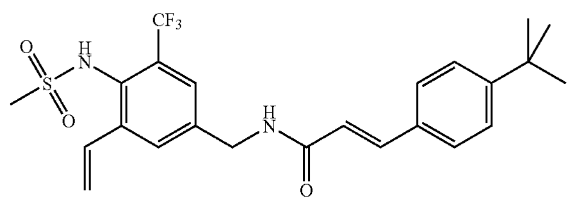 |
| 25 | 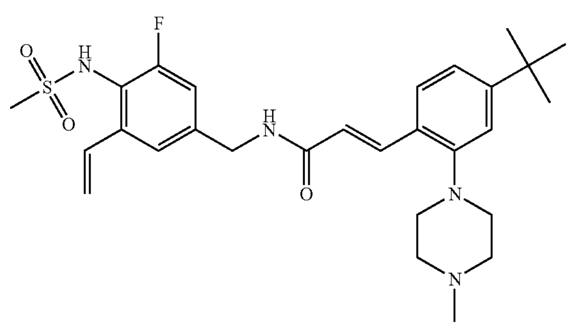 |
| 26 | 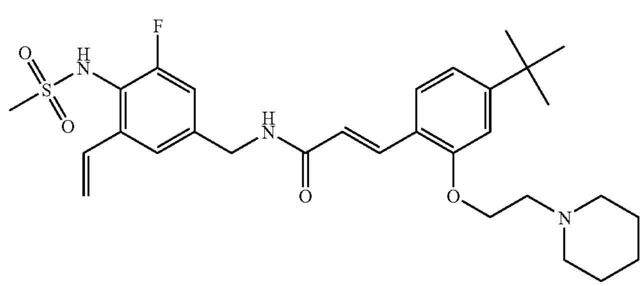 |

TABLE 1-continued
| Example No. | Structure |
|---|---|
| 27 | 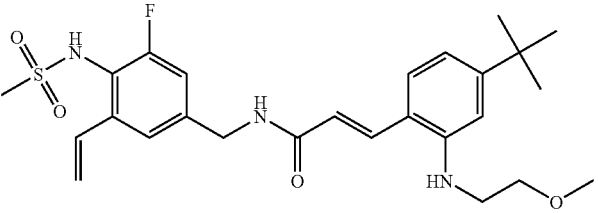 |
| 28 | 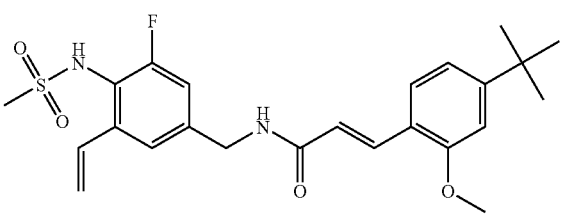 |
| 29 | 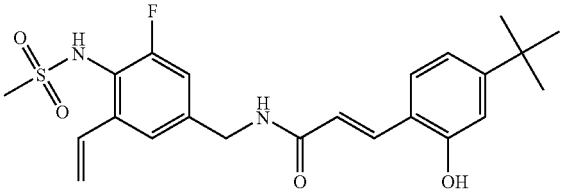 |
| 30 | 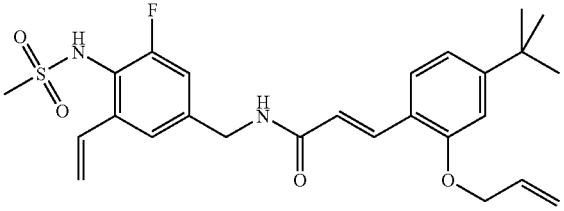 |
| 31 | 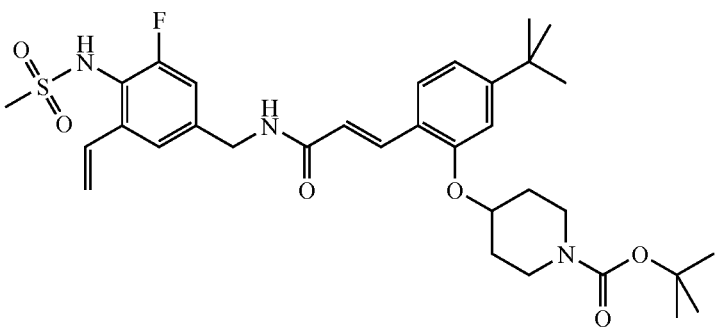 |
| 32 | 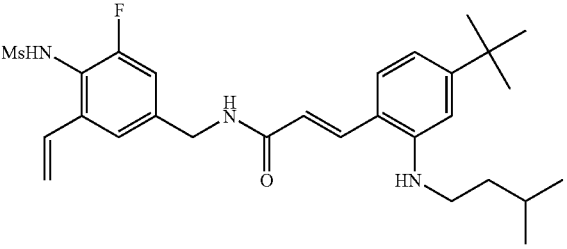 |

TABLE 1-continued

| Example No. | Structure |
|---|---|
| 33 | (MsHN, F, vinyl-substituted benzyl)-NH-C(=O)-CH=CH-(4-tert-butyl-2-(isobutylamino)phenyl) |
| 34 | (MsHN, F, vinyl-substituted benzyl)-NH-C(=O)-CH=CH-(4-tert-butyl-2-(isopropylamino)phenyl) |
| 35 | (MsHN, F, vinyl-substituted phenyl)-CH(CH₃)-NH-C(=O)-CH₂CH₂-(4-tert-butylphenyl) |
| 36 | (MsHN, F, vinyl-substituted phenyl)-CH(CH₃)-NH-C(=O)-CH=CH-(4-tert-butylphenyl) |
| 37 | (MsHN, F, vinyl-substituted benzyl)-NH-C(=O)-C(CH₃)=CH-(4-tert-butylphenyl) |
| 38 | (MsHN, F, vinyl-substituted benzyl)-NH-C(=O)-C(F)=CH-(4-tert-butylphenyl) |
| 39 | (MsHN, F, vinyl-substituted benzyl)-NH-C(=O)-CH=CH-(4-tert-butyl-2-(2-morpholinoethoxy)phenyl) |

TABLE 1-continued

| Example No. | Structure |
| --- | --- |
| 40 | 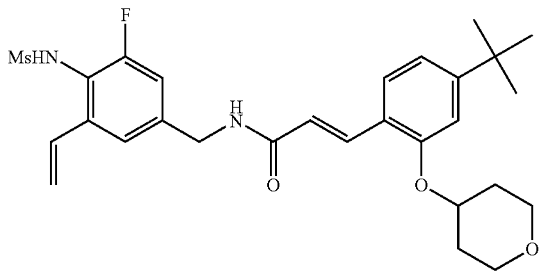 |
| 41 | 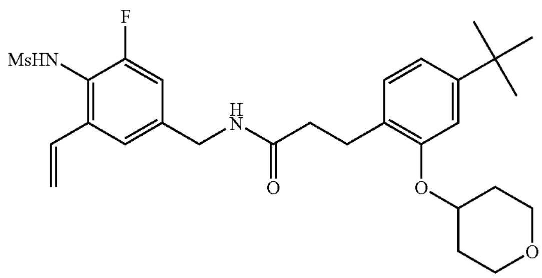 |
| 42 | 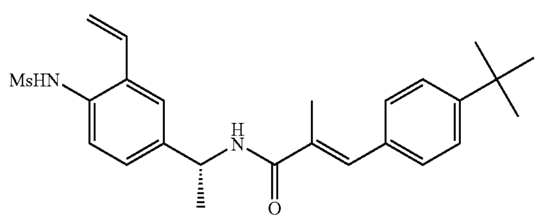 |
| 43 | 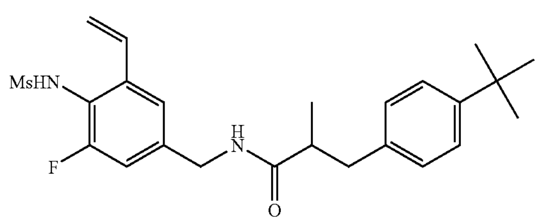 |
| 44 | 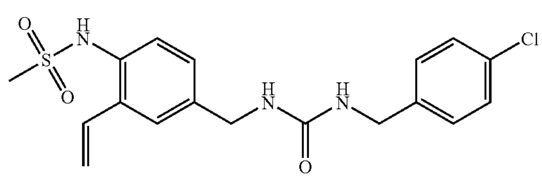 |
| 45 | 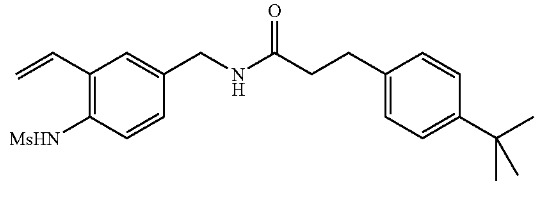 |

TABLE 1-continued

| Example No. | Structure |
|---|---|
| 46 | (structure) |
| 47 | (structure) |
| 48 | (structure) |
| 49 | (structure) |
| 50 | (structure) |
| 51 | (structure) |
| 52 | (structure) |

TABLE 1-continued

| Example No. | Structure |
|---|---|
| 53 | (structure: 4-(methylsulfonamido)-3-vinylphenyl group attached to (S)-CH(CH₃)-NH-C(O)-NH-(4-tert-butylphenyl)) |
| 54 | (structure: 4-(methylsulfonamido)-3-(TMS-ethynyl)phenyl group attached to (S)-CH(CH₃)-NH-C(O)-NH-(4-tert-butylphenyl)) |
| 55 | (structure: 4-(methylsulfonamido)-3-ethynylphenyl group attached to (S)-CH(CH₃)-NH-C(O)-NH-(4-tert-butylphenyl)) |
| 56 | (structure: 4-(methylsulfonamido)-3-vinylphenyl group attached to CH₂-NH-C(O)-NH-(4-tert-butylphenyl)) |
| 57 | (structure: 4-(MsHN)-3-fluoro-5-vinylphenyl group attached to CH₂-NH-C(O)-NH-(4-tert-butylphenyl)) |

TABLE 1-continued

| Example No. | Structure |
|---|---|
| 58 | 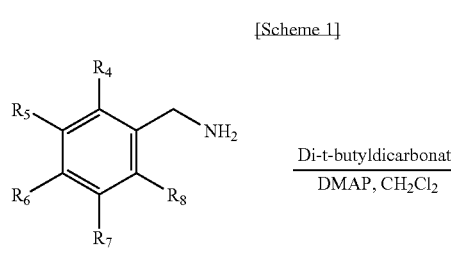 |
| 59 | 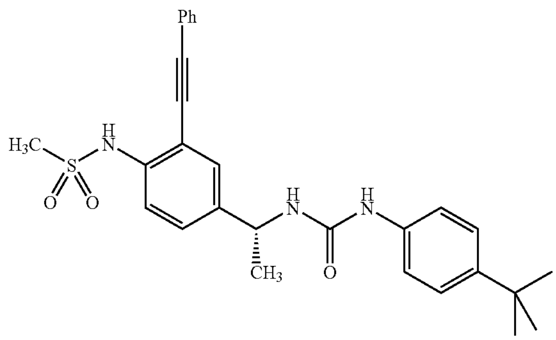 |
| 60 | 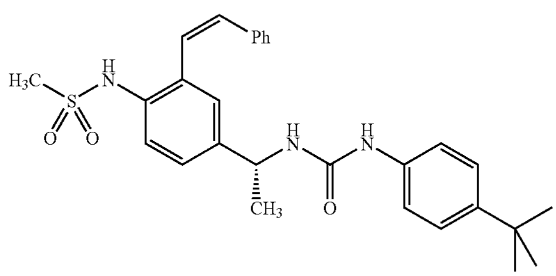 |

The compounds of formula (I) according to the present invention can chemically be synthesized by the following reaction schemes. However, these are given only for illustration of the invention and not intended to limit them.

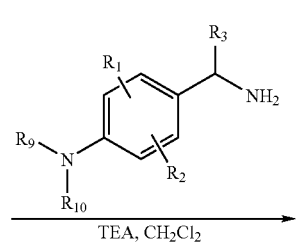

[Scheme 1]

-continued

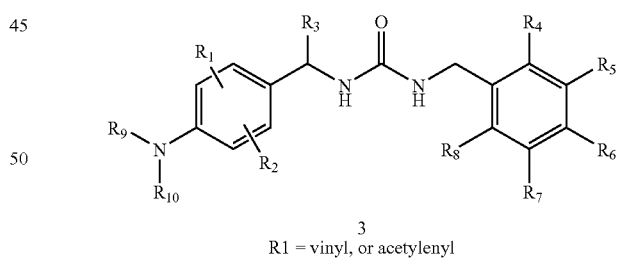

3
R1 = vinyl, or acetylenyl

The above Scheme 1 shows a proposed process for synthesizing dibenzyl urea with vinyl or acetylene. At first, substituted benzylamine is reacted with di-t-butyldicarbonate to yield benzyl carbamate in situ and to this reaction mixture is immediately added substituted benzylamine with vinyl or acetylenyl group (2) and triethylamine to yield dibenzylurea with vinyl or acetylene group (3).

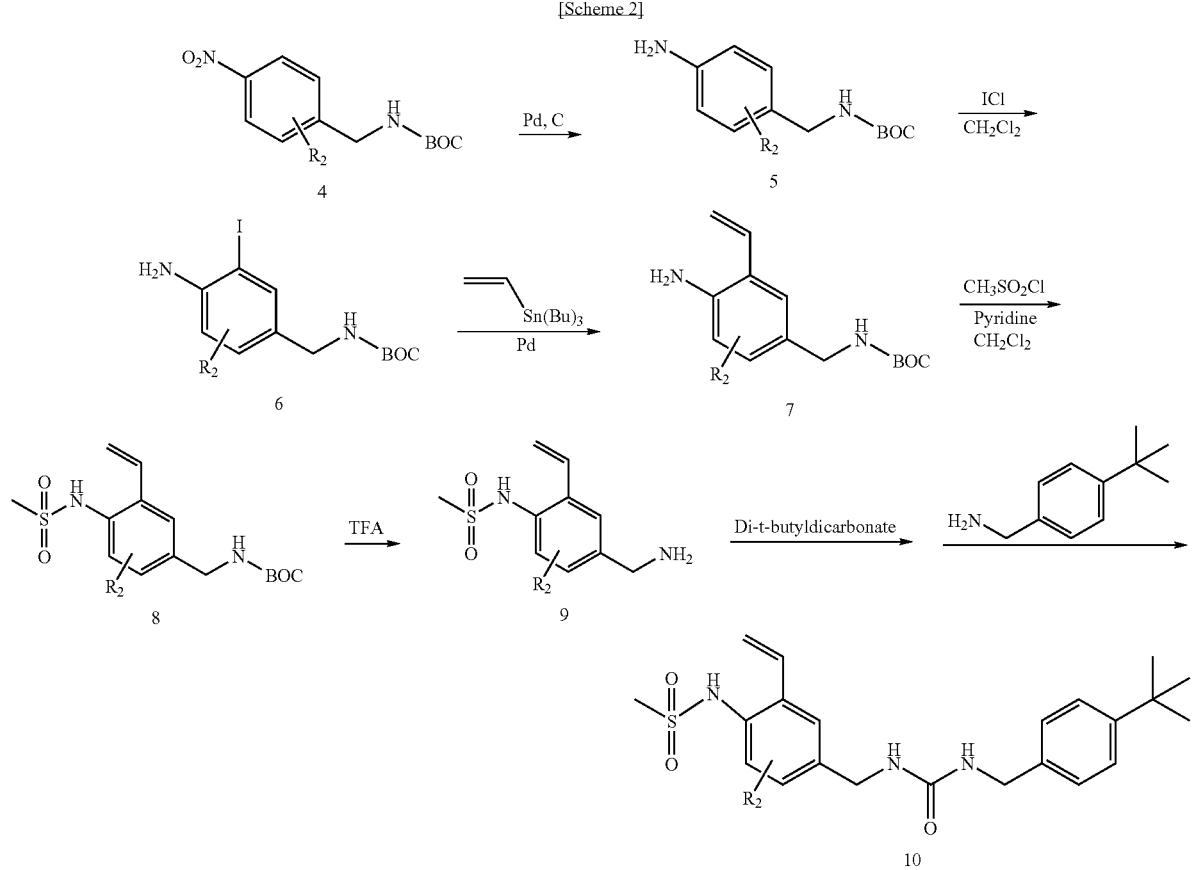

The above Scheme 2 shows various processes for synthesizing urea derivatives. At first, Boc derivatives of 4-nitrobenzylamine (4) is reduced to yield the aniline compound (5). The iodo group is introduced to the neighboring location of amino group of the compound (5) to yield the compound (6). Iodination of compound (5) can be achieved also at ortho position of amino by using iodine and silver sulfate at 0° C. (Synth. Commun. 1992, 22, 3215-3219). Vinyl stannane compound is coupled to the compound (6) to yield compound with vinyl group (7). The methanesulfonyl group is introduced to amino group of compound (7) to yield the compound (8). The protecting group (Boc) is removed using TFA (Trifluoroacetic acid) to yield the benzylamine compound (9). The dibenzyl urea derivatives (10) is synthesized according to the similar procedure as described in scheme 1.

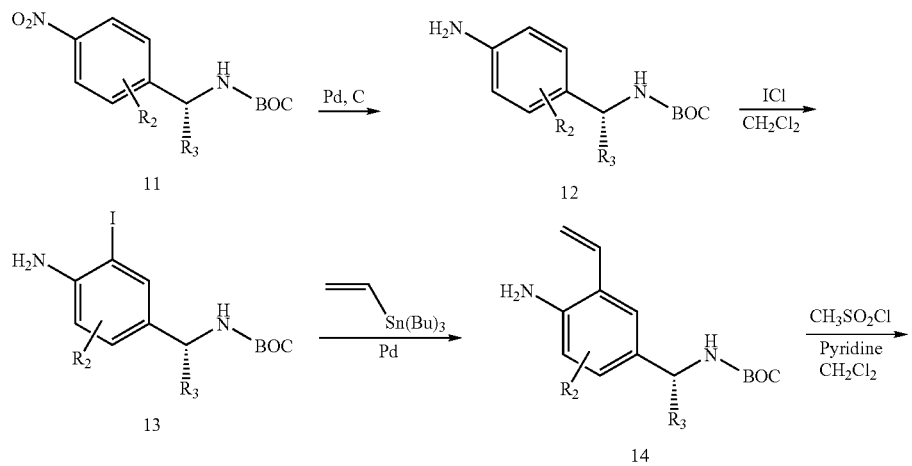

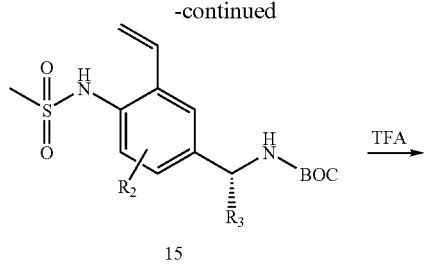

15

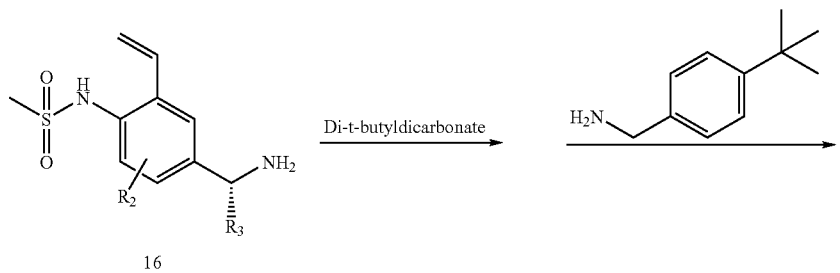

16

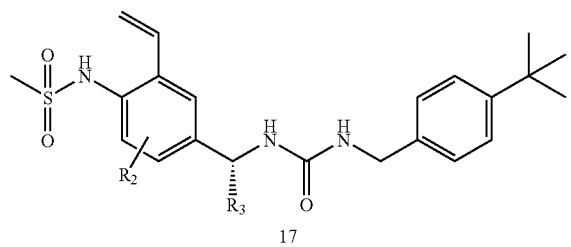

17

In various reactions for the synthesis of urea derivatives, the above Scheme 3 shows a proposed process for synthesizing urea derivatives with optical activity. The urea compound (17) having an optical activity is synthesized according to the above scheme 3 in which the reactant with methyl or ethyl group at $R_3$ position is used as a starting material.

[Scheme 4]

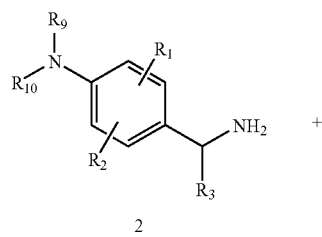

2

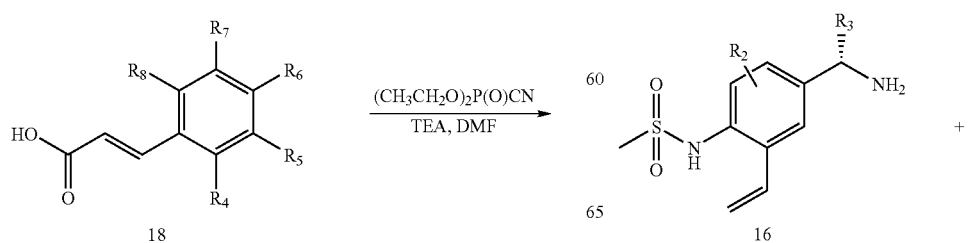

18

-continued

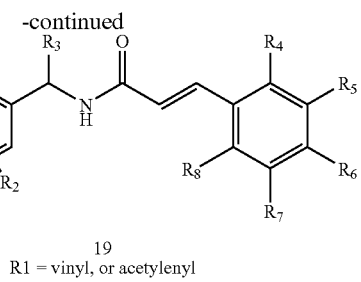

19
R1 = vinyl, or acetylenyl

The above Scheme 4 shows a proposed process for synthesizing the acrylamide compounds (19). Unsaturated arylacrylic acid (18) and diethylcyanophosphate are dissolved in DMF and stirred. To the reaction solution is added benzylamine compound (2) and the resulting solution was stirred overnight to yield the acrylamide compound (19).

[Scheme 5]

16

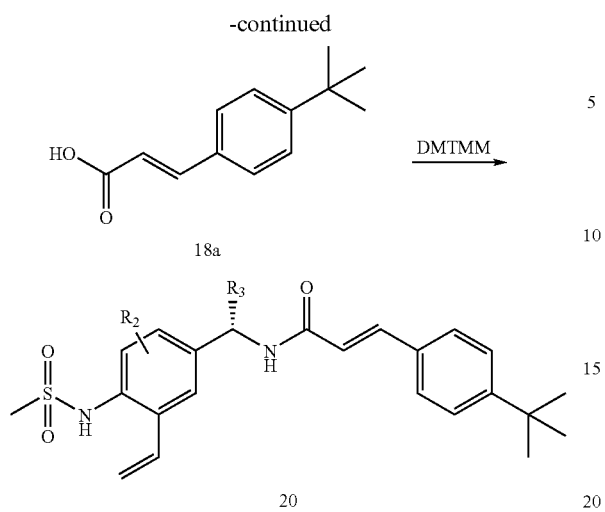

The above Scheme 5 shows another process for synthesizing the acrylamide compound. The compound (20) is synthesized using DMTMM {4-(4,6-dimethoxy-1,3,5-triazin-2-yl)-4-methylmorpholinium chloride} (Tetrahedron Lett., 1999, 40, 5327) instead of diethylcyanophosphate.

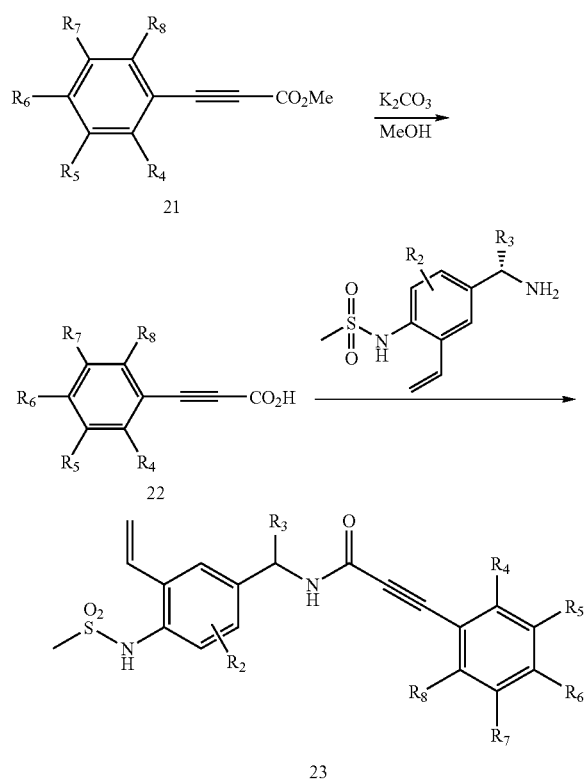

The above Scheme 6 shows a proposed process for synthesizing the propiolic amide compound (23). The acid compound (22) possessing a triple bond is reacted with the benzylamine compound (2) to yield the purposed compound (23).

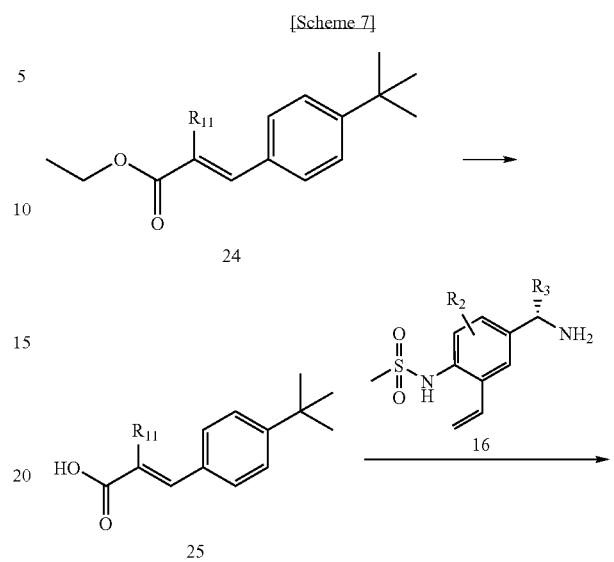

The above Scheme 7 shows a proposed process for synthesizing the acrylamide derivatives (26). The fatty acid ester compound (24) having various substituents at alkene position of unsaturated fatty acid is hydrolyzed to yield the fatty acid (25). The compound (26) is synthesized using the unsaturated fatty acid (25) with substituent according to the same procedure as described in scheme 4.

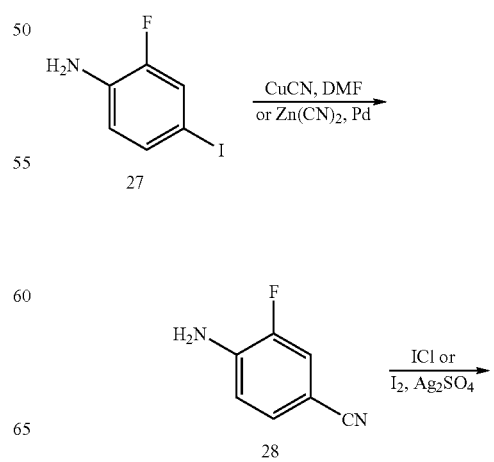

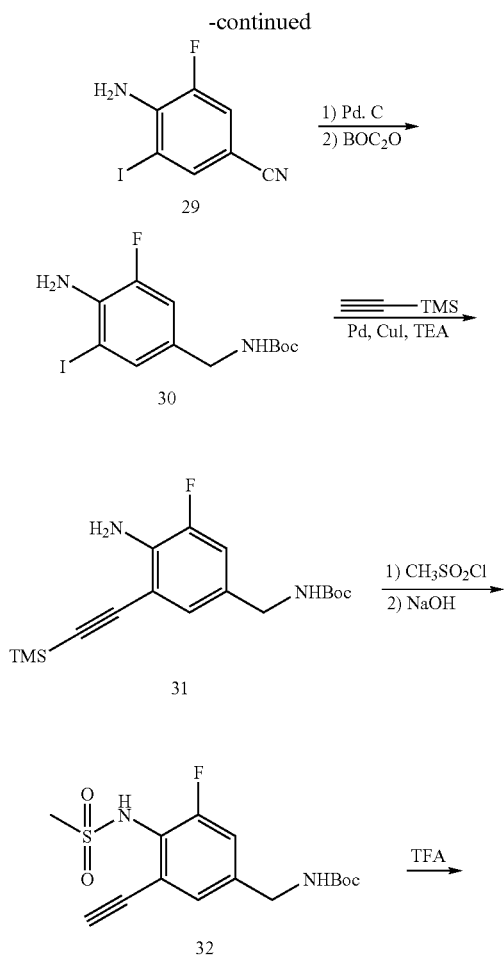

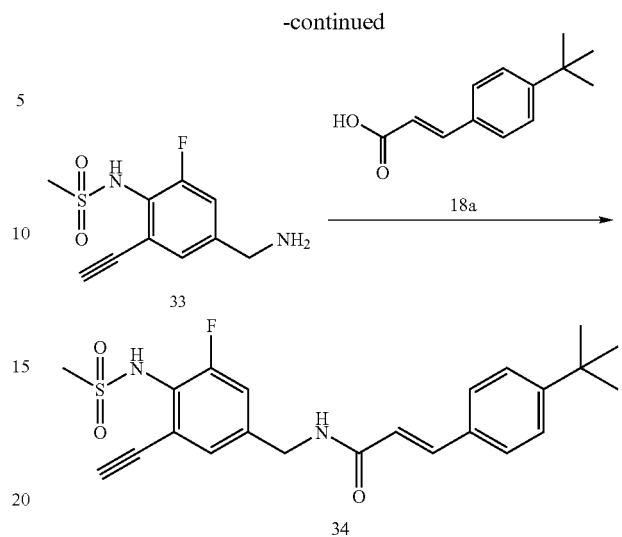

The above Scheme 8 shows a proposed process for synthesizing the acrylamide compound (34) with acetylene substituent group. At first, iodo group is introduced at the neighboring location of amine group of aniline compound (28) to yield the compound (29). The iodo-compound is reduced and thereto the benzylamine is Boc-protected to yield compound (30). The compound (30) can be also synthesized by carrying out reduction and iodination in order. After the iodo group of compound (30) is substituted with acetylene substituent, the amine group neighboring to benzene is treated with methanesulfonyl to yield the compound (32). The Boc-protecting group of the compound (32) is removed to prepare benzylamine compound (33). Benzylamine compound (33) having the acetylene substituent is reacted with unsaturated fatty acid to yield the acrylamide compound (34).

[Scheme 9]

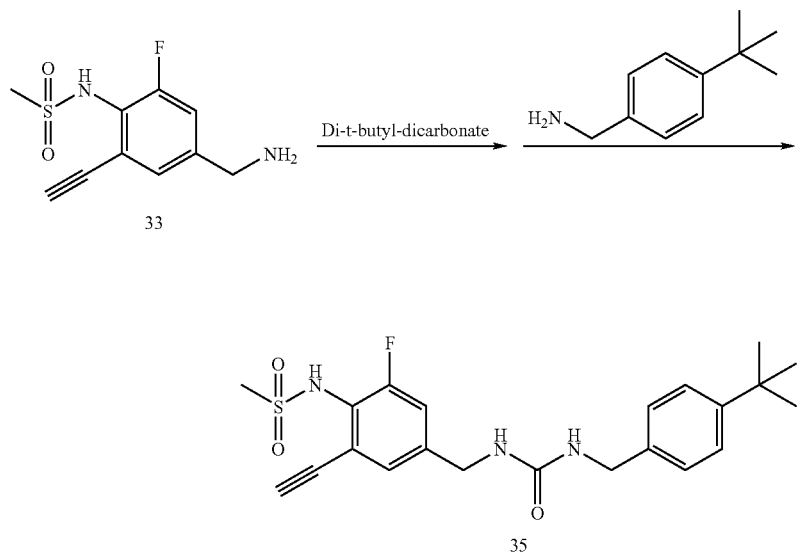

The above Scheme 9 shows a proposed process for synthesizing urea compound (35) with acetylene substituent group.

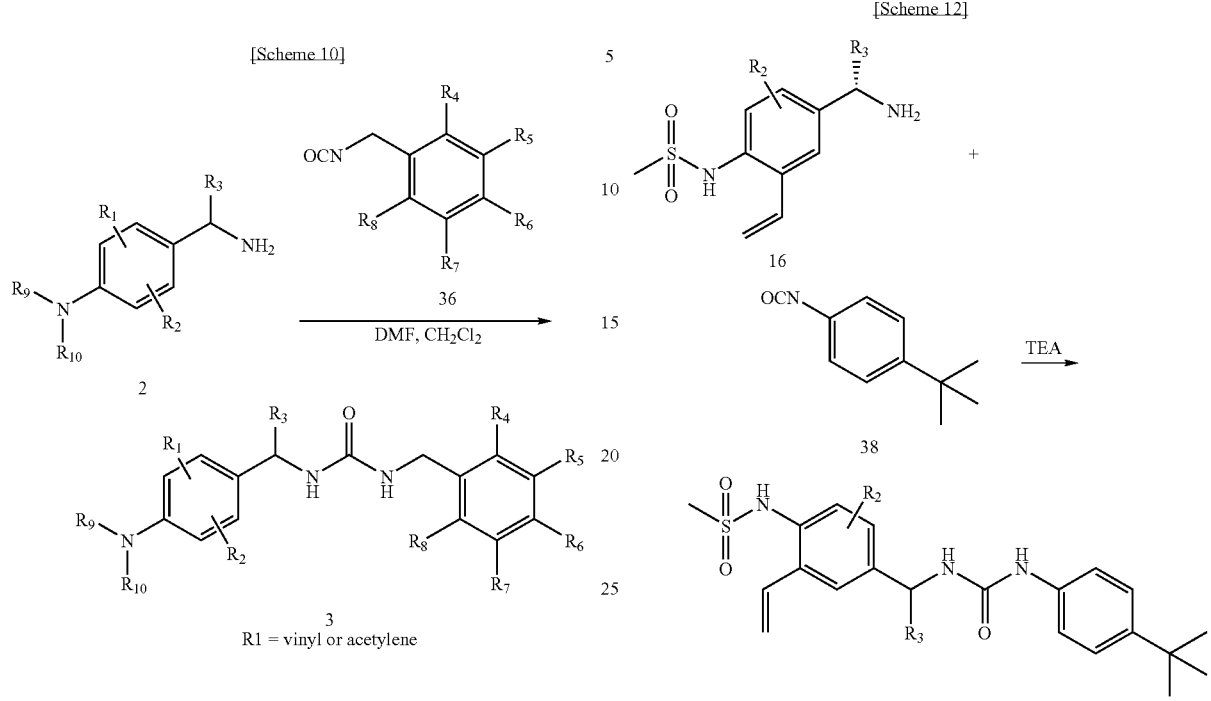

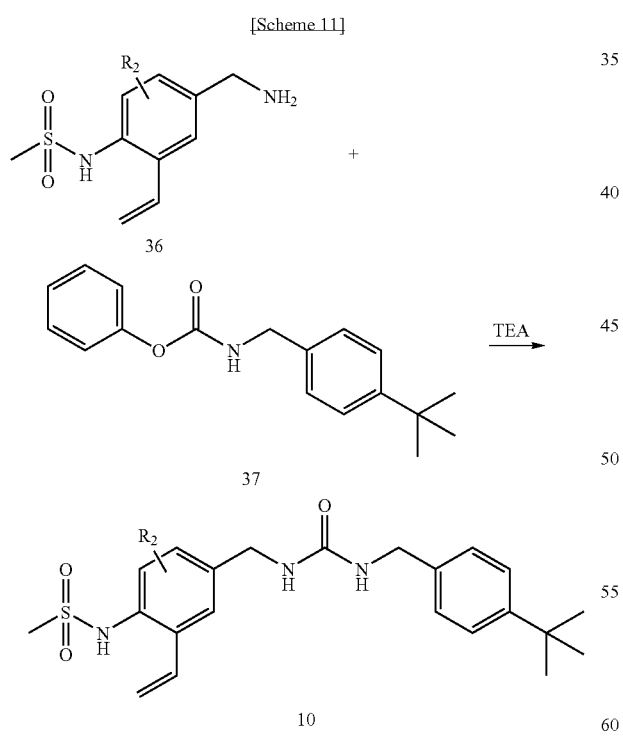

The above Scheme 10 shows a new process using benzyl isocyanate compound to synthesize urea compound.

The above Scheme 11 shows another reaction for synthesizing various urea derivatives. Benzylamine compound with various substituents is reacted with (4-tert-butyl-benzyl)-carbamic acid phenyl ester to yield the urea compound with vinyl group (10).

The Scheme 12 shows a proposed process for synthesizing urea compound with the vinyl substituent (39).

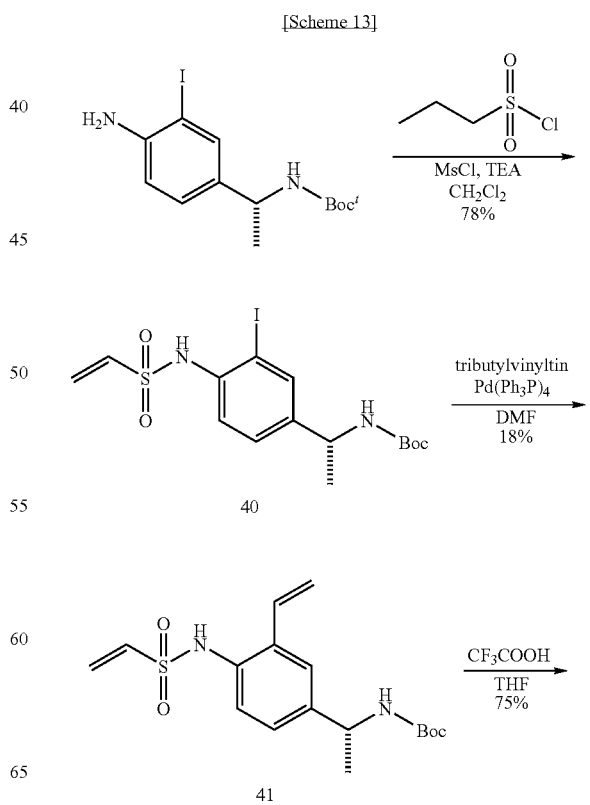

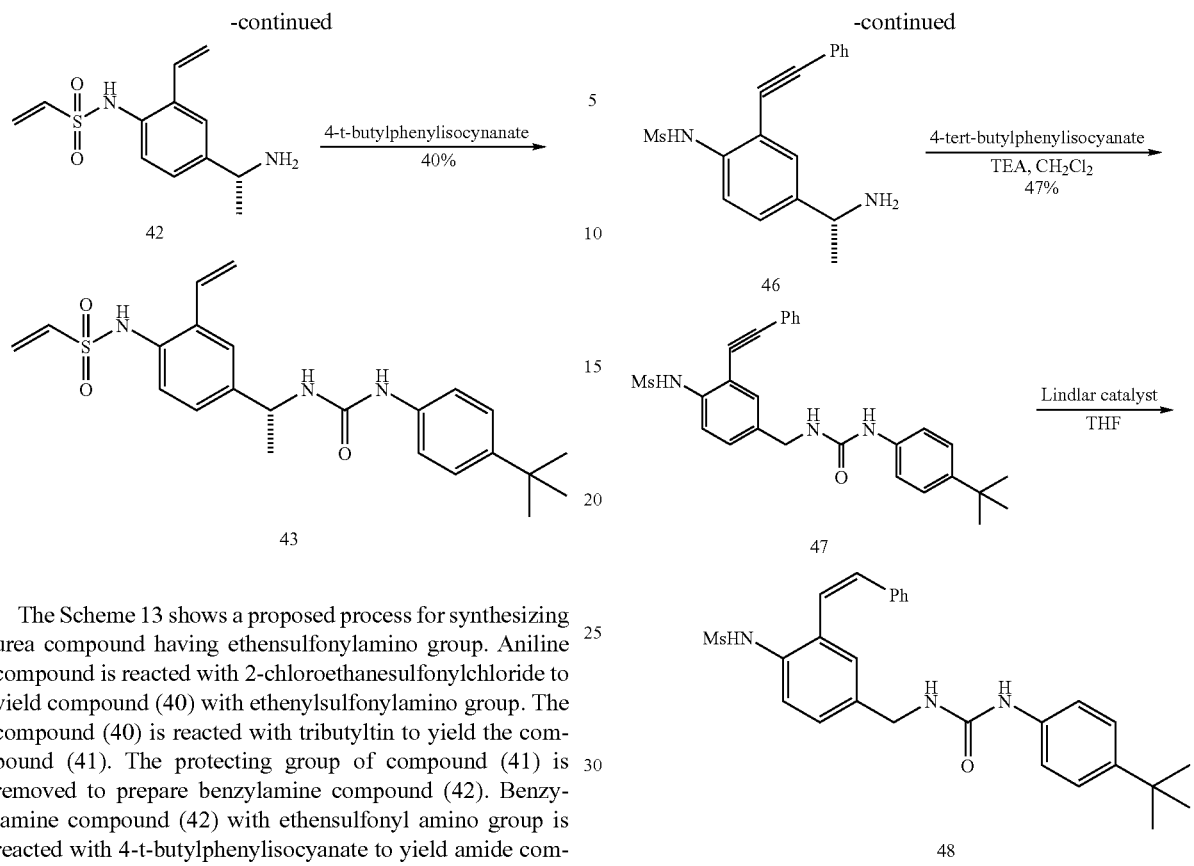

The Scheme 13 shows a proposed process for synthesizing urea compound having ethensulfonylamino group. Aniline compound is reacted with 2-chloroethanesulfonylchloride to yield compound (40) with ethenylsulfonylamino group. The compound (40) is reacted with tributyltin to yield the compound (41). The protecting group of compound (41) is removed to prepare benzylamine compound (42). Benzylamine compound (42) with ethensulfonyl amino group is reacted with 4-t-butylphenylisocyanate to yield amide compound (43).

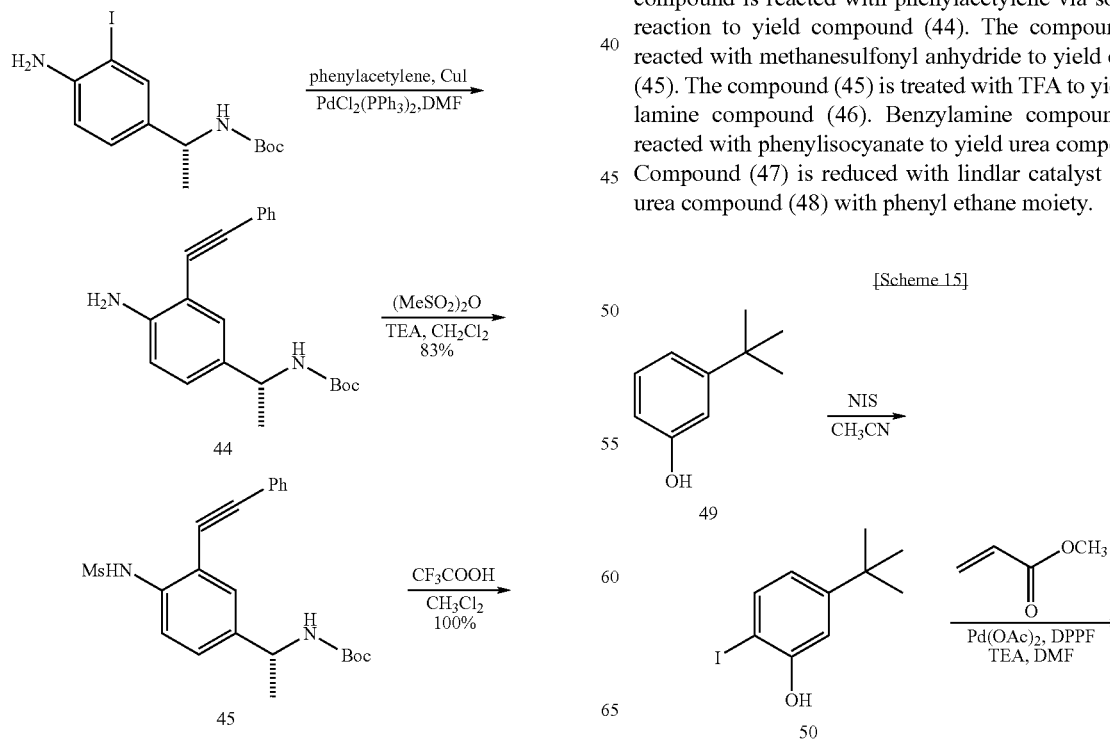

The Scheme 14 shows a proposed process for synthesizing urea compound having phenylacetylenyl group. Iodoaniline compound is reacted with phenylacetylene via sonogashira reaction to yield compound (44). The compound (44) is reacted with methanesulfonyl anhydride to yield compound (45). The compound (45) is treated with TFA to yield benzylamine compound (46). Benzylamine compound (46) is reacted with phenylisocyanate to yield urea compound (47). Compound (47) is reduced with lindlar catalyst to prepare urea compound (48) with phenyl ethane moiety.

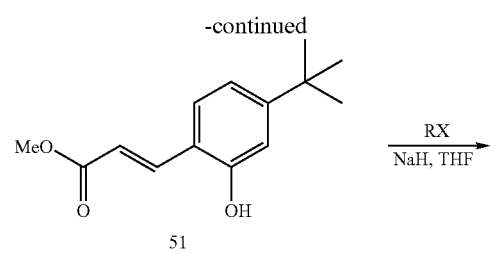

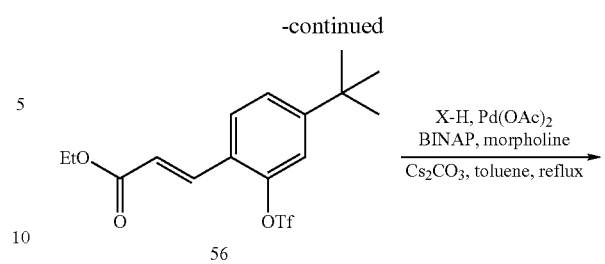

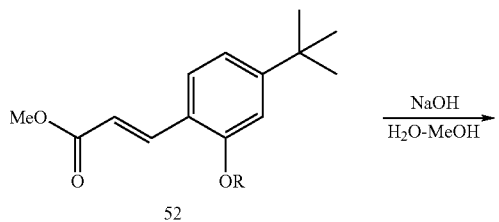

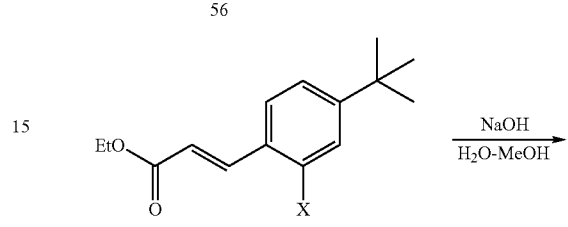

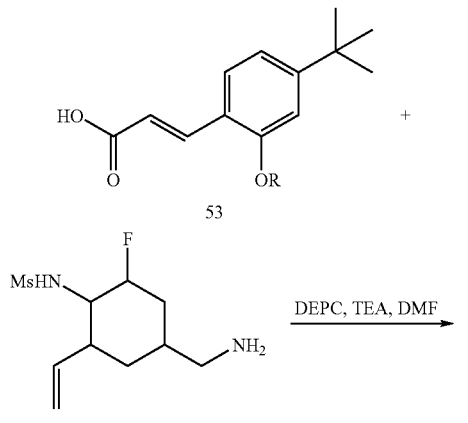

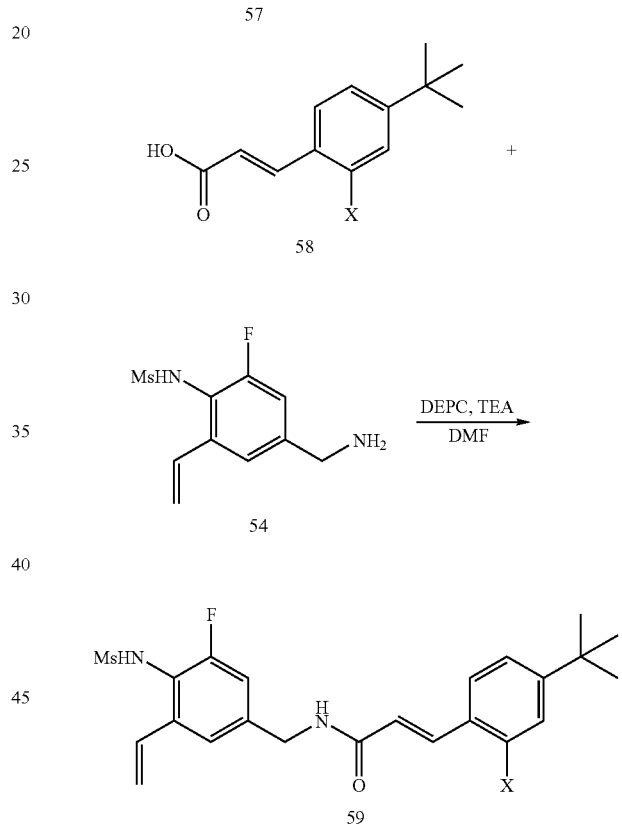

The Scheme 15 shows a proposed process for synthesizing acrylamide compound with various substituents. 3-t-Butylphenol is reacted with NIS to yield compound (50). The compound (50) is reacted with methylacrylate to give compound (51). Compound (51) is reacted with alkyl halide or alkoxylalkyl halide to yield compound (52). Compound (52) is hydrolyzed in basic condition. Compound (53) is reacted with benzylamine compound to yield the compound (55).

The Scheme 16 shows also a proposed process for synthesizing acrylamide compound with various substituents.

[Scheme 16]

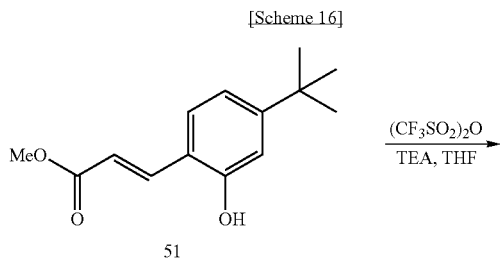

[Scheme 17]

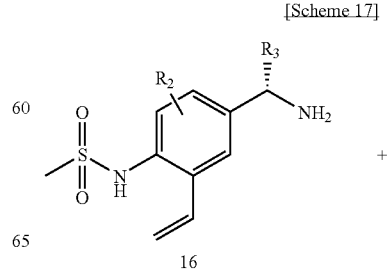

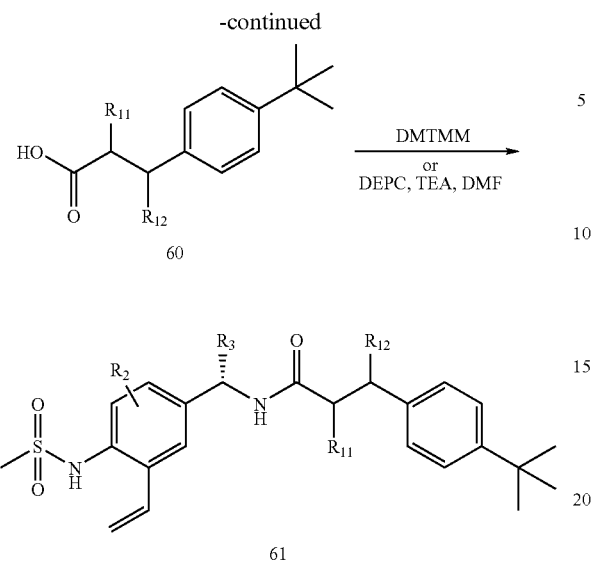

The above Scheme 17 shows two processes for synthesizing the propionamide compound (61). Amid compound (61) is obtained by using DEPC (diethylcyanophosphate) or DMTMM.

[Scheme 18]

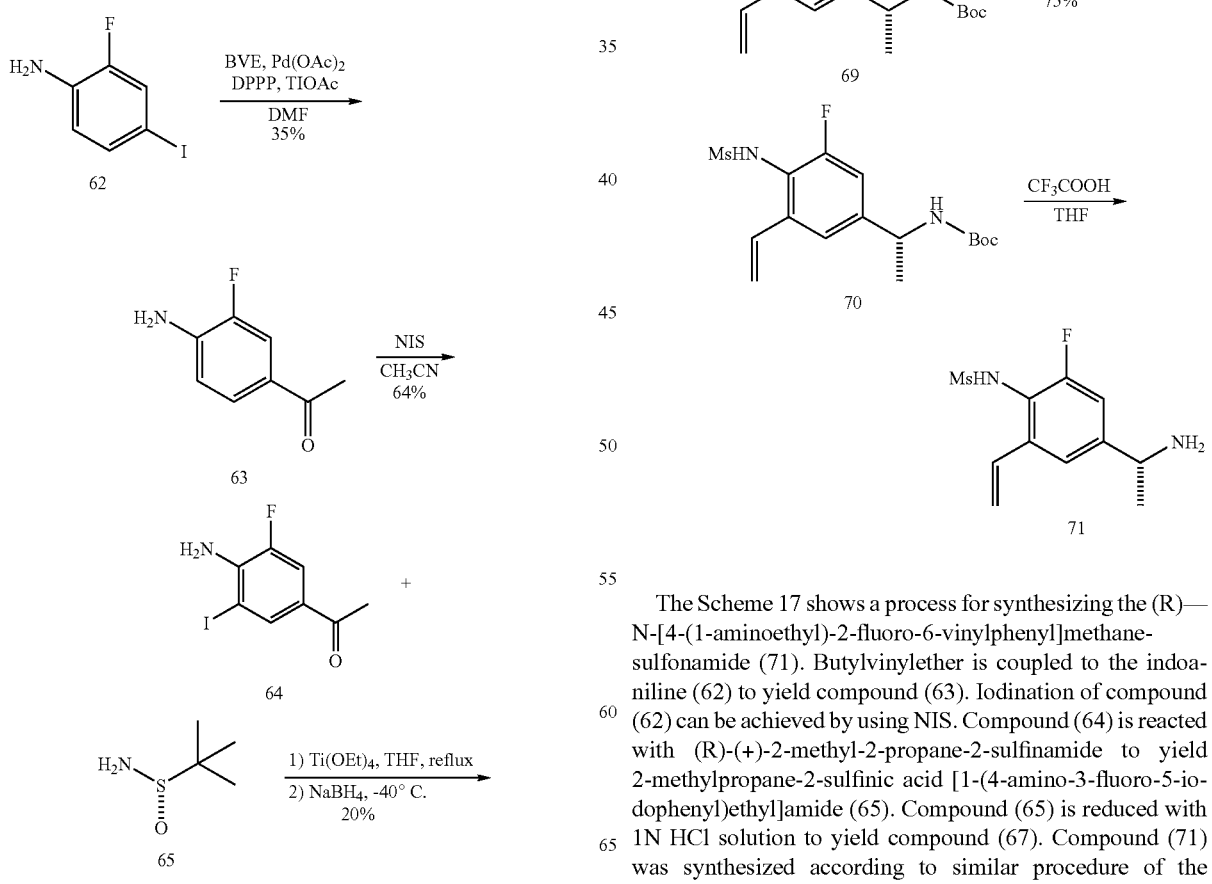

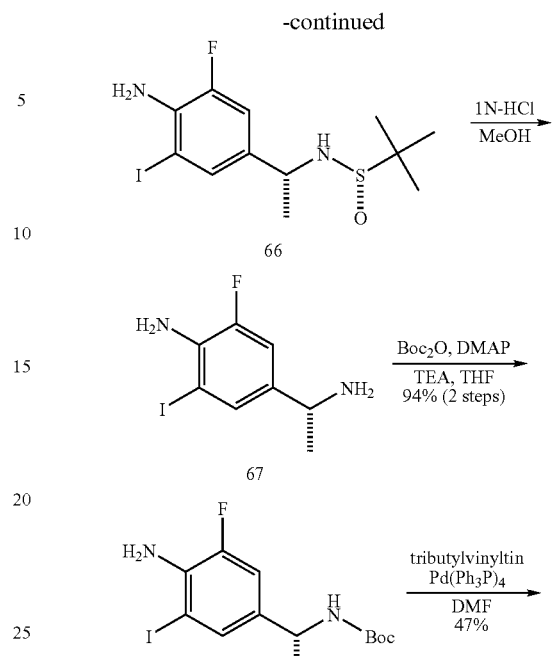

The Scheme 17 shows a process for synthesizing the (R)—N-[4-(1-aminoethyl)-2-fluoro-6-vinylphenyl]methanesulfonamide (71). Butylvinylether is coupled to the indoaniline (62) to yield compound (63). Iodination of compound (62) can be achieved by using NIS. Compound (64) is reacted with (R)-(+)-2-methyl-2-propane-2-sulfinamide to yield 2-methylpropane-2-sulfinic acid [1-(4-amino-3-fluoro-5-iodophenyl)ethyl]amide (65). Compound (65) is reduced with 1N HCl solution to yield compound (67). Compound (71) was synthesized according to similar procedure of the Scheme 3.

[Scheme 19]

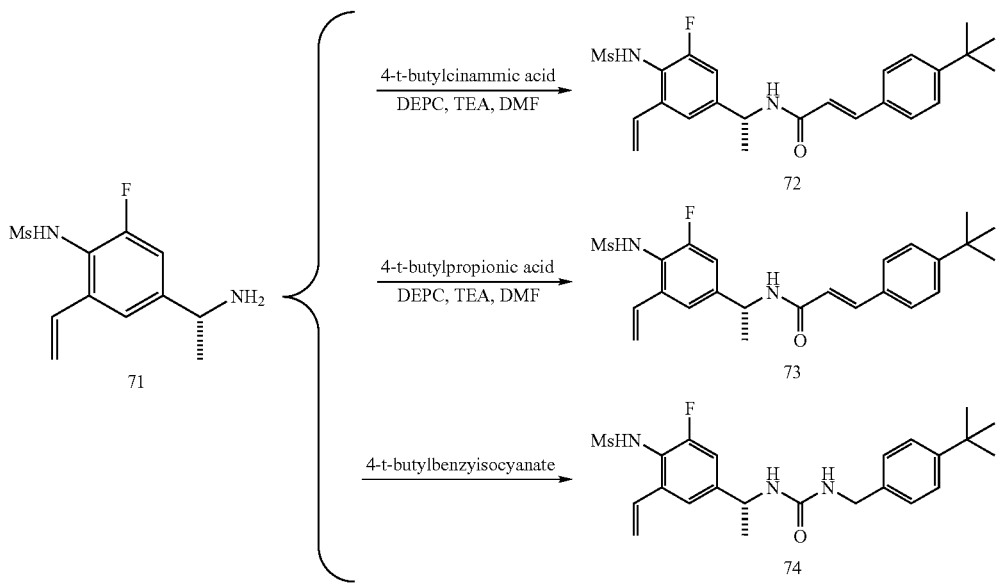

The Scheme 17 shows a process for synthesizing a specific unsaturated amide compound (72), amide compound (73) and urea compound (74).

The present invention also provides a pharmaceutical composition comprising a compound of formula (I), (Ia), (Ib), (Ic) or (Id), an isomer thereof, or a pharmaceutically acceptable salt thereof as an active ingredient together with a pharmaceutically acceptable carrier.

In said pharmaceutical composition, a compound of formula (I), (Ia), (Ib), (Ic) or (Id), an isomer thereof, or a pharmaceutically acceptable salt thereof as an active ingredient together with an pharmaceutically acceptable carrier is present in an effective amount for preventing or treating pain, acute pain, neuropathic pain, post-operative pain, migraine, arthralgia, neuropathies, nerve injury, diabetic neuropathy, neurodegeneration, stroke, neurotic/allergic/inflammatory skin disease, psoriasis, pruritus, prurigo, urinary bladder hypersensitiveness, irritable bowel syndrome, fecal urgency, Crohn's disease, respiratory disorder such as asthma or chronic obstructive pulmonary disease, irritation of skin, eye or mucous membrane, stomach-duodenal ulcer, inflammatory bowel disease or inflammatory diseases.

The present invention also provides a pharmaceutical composition for preventing and treating a disease associated with the pathological stimulation and/or aberrant expression of vanilloid receptor, wherein said composition comprises a compound of formula (I), (Ia), (Ib), (Ic) or (Id), an isomer thereof or a pharmaceutically acceptable salt thereof; and pharmaceutically acceptable carrier.

The present invention also provides a pharmaceutical composition for preventing and treating a condition related to vanilloid receptor, where said composition comprises a compound of formula (I), (Ia), (Ib), (Ic) or (Id), an isomer thereof or a pharmaceutically acceptable salt thereof and pharmaceutically acceptable carrier.

In the above, said condition related to vanilloid receptor is pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, or heart disease.

More specifically, said condition related to vanilloid receptor is acute pain, chronic pain, neuropathic pain, post-operative pain, rheumatic arthrodynia, osteoarthritis pain, postherpetic neuralgia, diabetic neuropathy, HIV-related neuropathy, neurodegeneration, stroke, neurotic/allergic/inflammatory skin disease, psoriasis, pruritus, prurigo, asthma, chronic obstructive pulmonary disease, urinary incontinence, inflammatory bowel disease, hyperacusis, tinnitus, vestibular hypersensitiveness, or inotropic ischemia.

In one preferred aspect, the present invention provides a pharmaceutical composition for treating a condition selected from pain, inflammatory disease of the joints including inflammatory autoimmune diseases of the joints, urinary bladder hypersensitivity including urinary incontinence, stomach duodenal ulcer, irritable bowel syndrome (IBS) and inflammatory bowel disease (IBD), neurotic/allergic/inflammatory skin disease, psoriasis, asthma, chronic obstructive pulmonary disease (COPD), pruritus, or prurigo comprising a compound, an isomer thereof or a pharmaceutically acceptable salt thereof according to anyone of formula (I), (Ia), (Ib), (Ic) or (Id), as defined further above.

More specific, the inventive compounds can be used in a pharmaceutical composition for treating pain, wherein the pain is—or is associated with—a condition selected from osteoarthritis ("OA"), rheumatoid arthritis ("RA"), Ankylosing Spondylitis ("AS"), diabetic neuropathic pain, post-operative pain, non-inflammatory musculoskeletal pain (including fibromyalgia, myofascial pain syndrome and back pain), migraine and other types of headaches.

If the compounds of the present invention are said to be useful to treat pain associated with osteoarthritis, it shall not be excluded that this also comprises the treatment of other signs and symptoms of osteoarthritis. Besides reducing the pain associated with osteoarthritis, the pharmacological intervention of osteoarthritis may be aimed at maintaining the mobility and minimizing the disability of the joints.

The term "inflammatory disease of the joints" includes diseases that involve to a more or less degree inflammatory processes in the joints, e.g. in knees, fingers, hips etc. An example for such a disease is osteoarthritis. The term "inflammatory disease of the joints" does also include diseases or conditions which may involve autoimmune processes, such as e.g. rheumatoid arthritis or ankylosing spondylitis. The inventive treatment of "inflammatory diseases of the joints" is primarily aimed at treating pain associated with these conditions but may also aim at improving the function of the affected joints, either directly or indirectly, e.g. by reducing the pain associated with the movement of said joints.

One outcome of the administration of the compounds of the present invention to patients suffering from an inflammatory disease of the joints may thus be reducing the pain experienced by the subject suffering from said disease relative to the pain experienced by the subject immediately before the administration of the compounds or combinations of the present invention. Another outcome of said treatment may be preventing the re-occurrence of pain which has previously been reduced as a result of pharmaco- or other therapy. Another outcome of treatment may be decreasing the occurrence of and/or the severity of manifestations related to an inflammatory disease of the joints, including particularly osteoarthritis, rheumatoid arthritis ankylosing spondylitis. The treatment may suitably result in an improved functionality of the joints, such as decreased stiffness, improved mobility.

The term "osteoarthritis (OA)" as used herein typically includes diseases with a failure of a diarthrodial (movable, synovial-lined) joint. In idiopathic (primary) OA, the most common form of the disease, no predisposing factor is apparent. Secondary OA is attributable to an underlying cause. Pain and joint dysfunction are the cardinal symptoms of OA. The joint pain of OA is often described as a deep ache and is localized to the involved joint. Typically, the pain of OA is aggravated by joint use and relieved by rest, but, as the disease progresses, it may become persistent. Nocturnal pain, interfering with sleep, is seen particularly in advance OA of the hip and may be enervating. Stiffness of the involved joint on arising in the morning or after a period of inactivity may be prominent but usually lasts less than 20 minutes.

The term "RA" refers to Rheumatoid Arthritis. RA is a chronic inflammatory autoimmune disease that causes the immune system to attack the joints, and particularly the synovium in the joint. The synovium becomes inflamed and causes swelling and pain. Cardinal symptoms of RA are joint pain and stiffness but additional symptoms include muscle aches, anemia and fever. Diagnosis of RA can be confirmed by detecting an antibody in the blood called the "rheumatic (or "rheumatoid") factor" and/or by a blood sedimentation test. Other useful and common tests are the detection of the "antinuclear antibody" or the "C-reactive protein".

"AS" stands for Ankylosing Spondylitis, which is a chronic, progressive autoimmune disease characterized by arthritis, inflammation and eventual immobility of the joints, particularly the spinal joints. It causes pain and stiffness in the back (often in the morning hours) as a result of ongoing swelling and irritation of the spinal joints (vertebrae). Inflammation of the tendons and ligaments that connect and provide support to the vertebrae can lead to pain and tenderness in the ribs, shoulder blades, hips, thighs, shins, heels and along the bony points of the spines.

If the compounds according to the present invention are said to be of use in treating pain associated with an inflammatory autoimmune disease of the joints, this refers to the administration of the compounds or combinations of the compounds of the present invention to reduce at least one pain symptom experienced by a subject suffering from an inflammatory autoimmune disease of the joints including back pain, joint pain and muscle pain associated with RA or AS. Besides the pain relief, treatment of an inflammatory autoimmune disease of the joints may also include a decrease of the inflammation and/or swelling of the synovium and may help to improve the functionality (i.e. maintaining mobility, and minimizing disability) of the joints, in particular in patients suffering from RA or AS.

Treatment of "non-inflammatory musculoskeletal pain" refers to the administration of the compounds or combinations of the compounds of the present invention to reduce the pain experienced by a subject suffering from non-inflammatory musculoskeletal pain including back pain, fibromyalgia, and myofascial pain syndrome. One outcome of treatment may be reducing the pain experienced by the subject relative to the pain experienced by the subject immediately before the administration of the compounds or combinations of the present invention. Another outcome of treatment may be preventing reoccurrence of pain which has previously been reduced as a result of pharmacotherapy. Another outcome of treatment may be decreasing the occurrence of and/or the severity of manifestations related to non-inflammatory musculoskeletal pain including back pain, fibromyalgia, and myofascial pain syndrome. The treatment may suitably result in a reduction of increased muscle sensitivity characterized by pain evoked by a normally non-nociceptive stimulus (allodynia) or increased pain intensity evoked by nociceptive stimuli (hyperalgesia). Finally, the treatment of non-inflammatory musculoskeletal pain can also improve the associated symptoms of back pain, fibromyalgia, and myofascial pain syndrome.

The terms "fibromyalgia" or "FMS" relates to a syndrome that causes widespread pain and stiffness throughout the tissue that supports and moves bones and joints. Fibromyalgia can be diagnosed by the presence of excessive tenderness on applying pressure to at least 11 of 18 specific muscle-tendon sites.

"Myofascial pain syndrome" is a chronic non-degenerative, non-inflammatory musculoskeletal pain condition. Distinct areas within muscles or their delicate connective tissue coverings (fascia) become abnormally thickened or tight. When the myofascial tissues tighten and lose their elasticity, neurotransmitter ability to send and receive messages between the brain and body is damaged. Symptoms include muscle stiffness and aching and sharp shooting pains or tingling and numbness in areas distant from the trigger point. Most commonly trigger points are in the neck, back, or buttocks.

"Back pain" is a common non-inflammatory musculoskeletal pain condition that may be either acute or chronic. It may be caused by a variety of diseases and disorders that affect the lumbar spine. Low back pain is often accompanied by sciatica, which is pain that involves the sciatic nerve and is felt in the lower back, the buttocks, and the backs of the thighs.

The compounds of the present invention are also useful for treating signs and symptoms of an overactive bladder such as urinary incontinence, more specific urinary urge incontinence, urinary stress incontinence, urinary urgency, nocturia and/or urinary frequency.

The pharmaceutical compositions according to the present invention are preferably adapted for oral administration. Alternatively, if skin diseases are to be treated the pharmaceutical composition containing the inventive compounds may be also formulated for topical or transcutaneous use.

In another aspect, the present invention relates to a method for inhibiting vanilloid ligand from binding to vanilloid receptor in a patient, comprising contacting cells expressing vanilloid receptor in the patient with a compound of formula (I), (Ia), (Ib), (Ic) or (Id), an isomer thereof, or a pharmaceutically acceptable salt thereof.

In another aspect, the present invention relates to a method for preventing or treating a disease selected from pain, migraine, arthralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, which comprises administering to a mammal including a person in need thereof a therapeutically effective amount of a compound of formula (I), (Ia), (Ib), (Ic) or (Id), an isomer thereof, or a pharmaceutically acceptable salt thereof.

In the above method, the disease is also selected from acute pain, chronic pain, neuropathic pain, post-operative pain, diabetic neuropathy, neurodegeneration, stroke, neurotic/allergic/inflammatory skin disease, psoriasis, pruritus, prurigo, asthma, chronic obstructive pulmonary disease, urinary incontinence or inflammatory bowel disease.

In one preferred aspect of the invention, the above method is treating pain that is or that is associated with a condition selected from osteoarthritis ("OA"), rheumatoid arthritis ("RA"), Ankylosing Spondylitis ("AS"), diabetic neuropathic pain, non-inflammatory musculoskeletal pain (including fibromyalgia, myofascial pain syndrome and back pain), post-operative pain, migraine and other types of headache.

In another aspect, the present invention relates to the use of a compound of formula (I), (Ia), (Ib), (Ic) or (Id), an isomer thereof, or a pharmaceutically acceptable salt thereof as an antagonist of vanilloid receptor.

In another aspect, the present invention relates to the use of a compound of formula (I), (Ia), (Ib), (Ic) or (Id), an isomer thereof, or a pharmaceutically acceptable salt thereof for prevention or treatment of a condition related to vanilloid receptor, which is more specifically associated with the aberrant expression and/or aberrant activation of a vanilloid receptor.

In another aspect, the present invention relates to the use of a compound of formula (I), (Ia), (Ib), (Ic) or (Id), an isomer thereof, or a pharmaceutically acceptable salt thereof, in preparation of a medicament for prevention or treatment of a condition related to vanilloid receptor.

In a preferred aspect, the present invention relates to the use of a compound of formula (I), (Ia), (Ib), (Ic) or (Id), an isomer thereof, or a pharmaceutically acceptable salt thereof in the preparation of a medicament for the prevention or the treatment of a condition that is selected from pain, inflammatory autoimmune disease of the joints, urinary bladder hypersensitivity including urinary incontinence, stomach duodenal ulcer, irritable bowel syndrome (IBS) and inflammatory bowel disease (IBD), neurotic/allergic/inflammatory skin disease, psoriasis, asthma, chronic obstructive pulmonary disease (COPD), pruritus, or prurigo.

In a particularly preferred aspect, the present invention relates to the use of a compound for treating pain as described above, wherein the pain is or is associated with a condition that is selected from osteoarthritis ("OA"), rheumatoid arthritis ("RA"), Ankylosing Spondylitis ("AS"), diabetic neuropathic pain, post-operative pain, non-inflammatory musculoskeletal pain (including fibromyalgia, myofascial pain syndrome and back pain), migraine and other types of headaches.

Hereinafter, the formulating methods and kinds of excipients will be described, but the present invention is not limited to them.

A compound of formula (I), (Ia), (Ib), (Ic) or (Id), an isomer thereof or a pharmaceutically acceptable salt thereof according to the present invention can be prepared as a pharmaceutical composition containing pharmaceutically acceptable carriers, adjuvants, diluents and the like. For instance, the compounds of the present invention can be dissolved in oils, propylene glycol or other solvents which are commonly used to produce an injection. Suitable examples of the carriers include physiological saline, polyethylene glycol, ethanol, vegetable oils, isopropyl myristate, etc., but are not limited to them. For topical administration, the compounds of the present invention can be formulated in the form of ointment or cream.

The compound according to the present invention may also be used in the forms of pharmaceutically acceptable salts thereof, and may be used either alone or in combination or in admixture with other pharmaceutically active compounds.

The compounds of the present invention may be formulated into injections by dissolving, suspending or emulsifying in water-soluble solvent such as saline and 5% dextrose, or in water-insoluble solvents such as vegetable oils, synthetic fatty acid glyceride, higher fatty acid esters and propylene glycol. The formulations of the invention may include any of conventional additives such as dissolving agents, isotonic agents, suspending agents, emulsifiers, stabilizers and preservatives.

The preferable dose level of the compounds according to the present invention depends upon a variety of factors including the condition and body weight of the patient, severity of the particular disease, dosage form, and route and period of administration, but may appropriately be chosen by those skilled in the art. The compounds of the present invention are preferably administered in an amount ranging from 0.001 to 100 mg/kg of body weight per day, and more preferably from 0.01 to 30 mg/kg of body weight per day. Doses may be administered once a day, or several times a day with each divided portions. The compounds of the present invention are used in a pharmaceutical composition in an amount of 0.0001~10% by weight, and preferably 0.001~1% by weight, based on the total amount of the composition.

The pharmaceutical composition of the present invention can be administered to a mammalian subject such as rat, mouse, domestic animals, human being and the like via various routes. The methods of administration which may easily be expected include oral and rectal administration; intravenous, intramuscular, subcutaneous, intrauterine, duramatral and intracerebroventricular injections.

DETAILED DESCRIPTION OF THE INVENTION
DEFINITIONS

When describing the compounds, pharmaceutical compositions containing such compounds, methods of using such compounds and compositions, and use of such compounds and compositions, all terms used in the present application shall have the meaning usually employed by a relevant person skilled in the art, e.g. by a medicinal chemists, pharmacist or physician. By the way of example some definitions of specific groups are given below:

"Alkyl" includes monovalent saturated aliphatic hydrocarbyl groups. The hydrocarbon chain may be either straight-chained or branched. This term is exemplified by groups such as methyl, ethyl, n-propyl, isopropyl, n-butyl, iso-butyl, tert-butyl.

"Alkoxy" includes the group -OR where R is alkyl. Particular alkoxy groups include, by way of example, methoxy, ethoxy, n-propoxy, isopropoxy, n-butoxy, tert-butoxy, sec-butoxy, n-pentoxy, 1,2-dimethylbutoxy, and the like.

"Alkenyl" includes monovalent olefinically unsaturated hydrocarbyl groups being straight-chained or branched and having at least 1 double bond. Particular alkenyl groups include ethenyl (—CH=CH$_2$), n-propenyl (—CH$_2$CH=CH$_2$), isopropenyl(C(CH$_3$)=CH$_2$), and the like. A preferred "alkenyl" group is ethenyl(vinyl).

"Alkynyl" includes acetylenically unsaturated hydrocarbyl groups being straight-chained or branched and having at least 1 triple bond. A preferred alkynyl group is ethynyl(acetylene).

"Alkylamino" includes the group —NR'R", wherein R' is alkyl and R" is selected from hydrogen or alkyl "Alkylsulfonyl" includes a radical —S(O)$_2$R where R is an alkyl group as defined herein. Representative examples include, but are not limited to, methanesulfonyl, ethylsulfonyl, propylsulfonyl, butylsulfonyl and the like.

"Alkylthio" includes a radical —S—R where R is an alkyl group as defined herein that may be optionally substituted as defined herein. Representative examples include, but are not limited to, methylthio, ethylthio, propylthio, butylthio, and the like.

"Amino" refers to the radical —NH$_2$.

"Carboxy" refers to the radical —C(=O)OH.

"Ethenyl" refers to —CH=CH$_s$ which in the present application is also designated "vinyl".

"Ethynyl" refers to —C≡CH.

"Halo" or "halogen" refers to fluoro, chloro, bromo and iodo. Preferred halo groups are either fluoro or chloro.

"Haloalkyl" includes an "alkyl" group as defined further above which is substituted with one or more halogens which may be the same, e.g. in trifluoromethyl or pentafluoroethyl, or which may be different.

"Hydroxy" refers to the radical —OH.

"Nitro" refers to the radical —NO$_2$.

"Piperidinyl(C1-C5) alkoxy" refers to a piperidinyl residue that is bound to "alkoxy" as defined further above, wherein the piperidinyl is preferably bound to a C-atom of "alkoxy" via the nitrogen or via the para-C-Atom of the piperidine ring.

"Morpholinyl(C1-C5) alkyloxy" refers to a morpholine residue that is bound to "alkoxy", wherein the morpholinyl ring is preferably bound to a C-Atom of "alkoxy" via the nitrogen atom of the morpholine ring.

"Tetrahydropyranyloxy" refers to a tetrahydropyranyl group that is bound to an oxo (—O—) group, wherein the oxo group is preferably bound to the para C-atom of the tetrahydropyranyl group.

"Alkylpiperazinyl" refers to a piperazine ring that carries an "alkyl" as substituent Preferably the piperazinyl ring is bound both to the "alkyl" as well as to the second attachment position via its nitrogen atoms.

"Piperidinyloxy" refers to a piperidinyl group that is bound to an oxo (—O—) group, wherein the oxo group is preferably bound to the para C-atom of the piperidinyl group.

"Pharmaceutically acceptable" means approved by a regulatory agency of the Federal or a state government or listed in the U.S. Pharmacopoeia or other generally recognized pharmacopoeia for use in animals, and more particularly in humans.

"Pharmaceutically acceptable salt" refers to a salt of a compound of the invention that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced.

"Pharmaceutically acceptable carrier" refers to a diluent, adjuvant, excipient or carrier with which a compound of the invention is administered.

"Preventing" or "prevention" refers to a reduction in risk of acquiring a disease or disorder (i.e., causing at least one of the clinical symptoms of the disease not to develop in a subject that may be exposed to or predisposed to the disease but does not yet experience or display symptoms of the disease).

"Subject" includes humans. The terms "human," "patient" and "subject" are used interchangeably herein.

"Therapeutically effective amount" means the amount of a compound that, when administered to a subject for treating a disease, is sufficient to effect such treatment for the disease. The "therapeutically effective amount" can vary depending on the compound, the disease and its severity, and the age, weight, etc., of the subject to be treated.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

MODE FOR CARRYING OUT INVENTION

The present invention is more specifically explained by following examples and expirical examples. However, it should be understood that the extent of the present invention is not limited to the following examples and expirical examples Example 1

N-{4-[3-(4-t-butylbenzyl)ureidomethyl]-2-vinylphenyl}methanesulfonamide

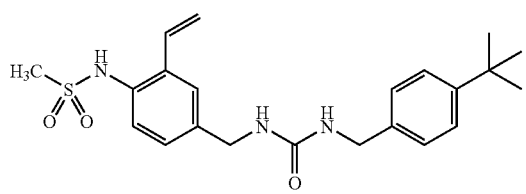

Step 1: (4-nitrobenzyl)carbamic acid t-butyl ester 4-nitrobenzylamine HCl (1 g, 5.302 mmol, 1 eq.) was put into 100 ml round-bottom flask and dissolved in the saturated solution (NaHCO$_3$:CH$_2$Cl$_2$=1:1). To the solution was added di-t-butyl dicarbonate (3.66 ml, 15.906 mmol, 3 eq.) and stirred for 3 hours. After confirming the completion of the reaction with TLC, the reaction solution was extracted with methylenechloride, washed with water (twice) and brine, dried over Na$_2$SO$_4$, filtered and concentrated under reduced pressure. The obtained liquid was column-chromatographed (n-hexane/ethyl acetate=10/1) to yield a pale light green solid (1.3171 g).

IR (KBr pellet, cm$^{-1}$): 3330, 3080, 301, 2984, 2916, 1687, 1513;
$^1$H NMR (400 MHz, CDCl$_3$): 8.11 (d, 2H, J=8.4 Hz), 7.37 (d, 2H, J=8.4 Hz), 4.99 (bs, 1H), 4.37 (d, 2H, J=5.6 Hz), 1.39 (s, 9H).

Step 2: (4-aminobenzyl)carbamic acid t-butyl ester (4-nitrobenzyl) carbamic acid t-butyl ester (1.3071 g, 5.880 mmol, 1 eq.) was put into 100 ml round-bottom flask and dissolved in methanol. The Pd/c (about 10 wt % of substrate) was added into the reaction mixture. Air in the flask was displaced with hydrogen gas fifteenth times or so. The resulting solution was stirred at room temperature for 2 hours. After confirming the progress of the reaction with TLC, the reaction solution was filtered through celite and evaporated to yield a pale yellow solid (1.1451 g).

IR (KBr pellet, cm$^{-1}$): 3426, 3346, 3021, 2995, 2976, 1687;
$^1$H NMR (400 MHz, CDCl$_3$): 7.09 (d, 2H, J=8.0 Hz), 6.70 (d, 2H, J=8.0 Hz), 4.74 (bs, 1H), 4.20 (d, 2H, J=5.0 Hz), 3.34 (bs, 2H), 1.46 (s, 9H).

Step 3: (4-amino-3-iodobenzyl)carbamic acid t-butyl ester

A 100 ml two-neck round bottom flask was filled with argon gas and the solution of (4-aminobenzyl) carbamic acid t-butyl ester (986.2 mg, 3.909 mmol, 1 eq.) in methylenechloride was put into the flask. To the solution was added iodomonochloride (698.2 mg, 4.300 mmol, 1.1 eq.) and stirred for 1 hour. After confirming the completion of the reaction with TLC, to the solution was added saturated sodium thiosulfate solution and stirred. The reaction solution was extracted with methylenechloride, washed with water (twice) and brine, dried over Na$_2$SO$_4$, filtered and concentrated under reduced pressure. The obtained liquid was column-chromatographed (n-hexane/ethyl acetate=3/1) to yield brown liquid (640 mg).

IR (NaCl neat, cm$^{-1}$): 3421, 3349, 2976, 2929, 1695;
$^1$H NMR (400 MHz, CDCl$_3$): 7.49 (d, 1H, J=2.0 Hz), 6.98 (dd, 1H, J=8.0, 2.0 Hz), 6.61 (d, 1H, J=8.0 Hz), 4.87 (bs, 1H), 4.07 (d, 2H, J=4.0 Hz), 3.98 (bs, 2H), 1.40 (s, 9H)

Step 4: (4-amino-3-vinylbenzyl)carbamic acid t-butyl ester

A 50 ml two-neck round bottom flask was filled with argon gas and the solution of tetrakis(triphenyl phosphine)palladium(0) (123.7 mg, 0.107 mmol, 0.06 eq.) and lithium chloride (211.9 mg, 4.998 mmol, 2.8 eq.) in DMF was put into the flask. To the solution was added (4-amino-3-iodobenzyl) carbamic acid t-butyl ester (621.4 mg, 1.875 mmol, 1 eq.) and tributylvinyltin (782.5 mg, 2.678 mmol, 1.5 eq.). The mixture solution was heated to 90° C. to reflux for one night. After confirming the completion of the reaction with TLC, the reaction solution was extracted with methylenechloride, washed with water and brine, dried over Na$_2$SO$_4$, filtered and evaporated. The obtained liquid was column-chromatographed (n-hexane/ethyl acetate=3/1) to yield brown liquid.

Step 5: (4-methanesulfonylamino-3-vinylbenzyl)carbamic acid t-butyl ester

A 50 ml two-neck round bottom flask was filled with argon gas and the solution of (4-aminobenzyl) carbamic acid t-butyl ester (343.0 mg, 1.381 mmol, 1 eq.) in methylenechloride was put into the flask. To the solution was added methanesulfonic anhydride (264.7 mg, 1.519 mmol, 1.1 eq.) at 0° C., followed by adding pyridine (332.0 µl, 4.413 mmol, 2 eq.) and stirring for 1 hour. After confirming the completion of the reaction with TLC, to the solution was added saturated NaHCO$_3$ solution and stirred for 5 minutes. The reaction solution was extracted with methylenechloride and washed with 5% HCl, saturated NaHCO$_3$ solution, water and brine. The resulting solution was dried over Na$_2$SO$_4$, filtered and evaporated. The obtained solid was column-chromatographed (n-hexane/ethyl acetate=2/1) to yield a pale yellow solid (161.6 mg).

IR (KBr pellet, cm$^{-1}$): 3414, 3359, 3269, 3254, 3083, 2982, 2927, 1685;
$^1$H NMR (400 MHz, CDCl$_3$): 7.35 (d, 1H, J=8.0 Hz), 7.33 (d, 1H, J=2.0 Hz), 7.14 (dd, 1H, J=8.0, 2.0 Hz), 6.84 (dd, 1H, J=17.2, 10.8 Hz), 6.44 (bs, 1H), 5.65 (d, 1H, J=17.2 Hz), 5.40 (d, 1H, J=10.8 Hz), 4.84 (bs, 1H), 4.23 (d, 2H, J=5.6 Hz), 2.91 (s, 3H), 1.39 (s, 9H)

Step 6: N-(4-aminomethyl-2-vinylphenyl)methanesulfonamide (4-methanesulfonylamino-3-vinylbenzyl) carbamic acid t-butyl ester (161.6 mg) was put into 100 ml round-bottom flask and dissolved in methylenechloride. To the solution was added trifluoroacetic acid and stirred for one night. After confirming the completion of the reaction with TLC, the reaction solution was concentrated under reduced pressure to yield brown liquid (198.6 mg).

Step 7: N-4-[3-(4-t-butylbenzyl)ureidomethyl]-2-vinylphenylmethane Sulfonamide A 25 ml two-neck round bottom flask was filled with argon gas and the solution of 4-t-butylbenzylamine (27.7 µl, 0.158 mmol, 1 eq.) in methylenechloride was put into the flask. To the solution was added 4-dimethylaminopyridine (3.9 mg, 0.032 mmol, 0.2 eq.) and di-t-butyl dicarbonate (43.6 µl, 0.190 mmol, 1.2 eq.) and stirred at room temperature for 1 hour and 30 minutes. The resulting solution was cooled to 0° C. and the solution of N-(4-aminomethyl-2-vinyl-phenyl)-methanesulfonamide (35.7 mg, 0.158 mmol, 1 eq.) and triethylamine (44.0 µl, 0.316 mmol, 2 eq.) in methylenechloride was added. The mixture solution was stirred at room temperature for overnight. After confirming the completion of the reaction with TLC, methylenechloride was removed under reduced pressure. The residue was column-chromatographed (n-hexane/ethyl acetate=1/2) to yield a pale yellow solid (35.6 mg, 54.2%).

mp: 108-109° C.;
IR (KBr pellet, cm$^{-1}$): 3413, 3023, 2961, 2927, 1735;
$^1$H NMR (400 MHz, CDCl$_3$): 7.26 (d, 1H, J=1.6 Hz), 7.24 (d, 2H, J=8.4 Hz), 7.17 (d, 1H, J=8.0 Hz), 7.10 (d, 2H, J=8.4

Hz), 6.99 (dd, 1H, J=8.0, 1.6 Hz), 6.80 (dd, 1H, J=17.2, 10.8 Hz), 6.70 (s, 1H), 5.58 (dd, 1H, J=17.2, 0.8 Hz), 5.31 (dd, 1H, J=10.8, 0.8 Hz), 4.10 (bs, 2H), 4.20 (s, 2H), 2.83 (s, 3H), 1.21 (s, 9H)

Example 2

N-{4-[3-(4-t-butylbenzyl)ureidomethyl]-2-fluoro-6-vinylphenyl}methanesulfonamide

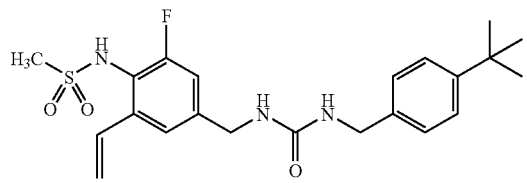

Step 1: 4-aminomethyl-2-fluoro-6-iodophenylamine

A 50 ml two-neck round bottom flask was filled with argon gas and the solution of 4-amino-3-fluoro-5-iodo-benzonitrile (84.4 mg, 0.322 mmol, 1 eq.) in tetrahydrofuran was put into the flask and then cooled to 0° C. To the solution was added Borane-THF complex solution (1.0M solution in THF, 0.64 ml, 0.64 mmol, 2 eq.). The temperature of reaction mixture was raised to room temperature. And the reaction mixture was heated and refluxed. After confirming the completion of the reaction with TLC, to the solution was added 5% HCl and stirred for 20 minutes. The resulting solution was basified using 1N KOH, extracted with ether, washed with brine and dried over $Na_2SO_4$. The obtained liquid was concentrated under reduced pressure to yield a pale yellow solid (78.4 mg, 80.5%).

IR (KBr pellet, $cm^{-1}$): 3429, 2923, 2853, 1626;
$^1$H NMR (400 MHz, $CD_3OD$): 7.33 (s, 1H), 6.93 (dd, 1H, J=11.6, 2.0 Hz), 3.58 (s, 2H),

Step 2: (4-amino-3-fluoro-5-iodobenzyl)carbamic acid t-butyl ester

A 25 ml two-neck round bottom flask was filled with argon gas and the solution of 4-aminomethyl-2-fluoro-6-iodophenylamine (31.9 mg, 0.120 mmol, 1 eq.) and triethylamine (18.4 µl, 0.132 mmol, 1.1 eq.) in methylenechloride was put into the flask and then cooled to 0° C. To the solution were added 4-dimethylaminopyridine (1.47 mg, 0.012 mmol, 0.1 eq.) and di-t-butyl dicarbonate (27.6 µl, 0.120 mmol, 1 eq.) and stirred for 5 hours. After confirming the completion of the reaction with TLC, the resulting solution was extracted with methylenechloride, washed with water and brine, dried over $Na_2SO_4$ and concentrated under reduced pressure. The obtained liquid was column-chromatographed (n-hexane/ethyl acetate=5/1) to yield a yellow liquid (9.8 mg, 22.3%).

IR (NaCl neat, $cm^{-1}$): 3451, 3351, 2975, 2928, 1698;
$^1$H NMR (400 MHz, $CDCl_3$): 7.87 (s, 0.2H), 7.44 (d, 0.2H, J=11.2 Hz), 7.26 (s, 1H), 6.87 (d, 1H, J=11.2 Hz), 4.72 (bs, 2H), 4.08 (d, 2H, J=4.4 Hz), 1.39 (s, 9H)

Step 3: (4-amino-3-fluoro-5-vinylbenzyl)carbamic acid t-butyl ester

A 25 ml two-neck round bottom flask was filled with argon gas and the solution of tetrakis (triphenyl phosphine) palladium(0) (18.9 mg, 0.016 mmol, 0.06 eq.) and lithium chloride (32.4 mg, 0.765 mmol, 2.8 eq.) in DMF was put into the flask. To the solution were added (4-amino-3-fluoro-5-iodo-benzyl)-carbamic acid t-butyl ester (100 mg, 0.273 mmol, 1 eq.) and tributylvinyltin (119.7%, 0.410 mmol, 1.5 eq.) and heated to reflux for 5 hours. After confirming the completion of the reaction with TLC, the resulting solution was extracted with ethylacetate, washed with water and brine, dried over $Na_2SO_4$ and concentrated under reduced pressure. The obtained liquid was column-chromatographed (n-hexane/ethyl acetate=5/1) to yield a brown liquid (52.5 mg, 72.2%).

IR (NaCl neat, $cm^{-1}$): 3412, 3088, 2958, 2925, 1689;
$^1$H NMR (400 MHz, $CDCl_3$): 7.53 (d, 1H, J=2.0 Hz), 7.39 (dd, 1H, J=10.8, 2.0 Hz), 6.64 (dd, 1H, J=17.6, 11.2 Hz), 5.69 (d, 1H, J=17.6 Hz), 5.42 (d, 1H, J=11.2 Hz), 4.36 (s, 2H), 1.49 (s, 9H)

Step 4: (3-fluoro-4-methanesulfonylamino-5-vinyl-benzyl)carbamic acid t-butyl ester A 25 ml two-neck round bottom flask was filled with argon gas and the solution of (4-amino-3-fluoro-5-vinyl-benzyl)-carbamic acid t-butyl ester (27.3 mg, 0.103 mmol, 1 eq.) in pyridine was put into the flask and then cooled to 0° C. To the solution was added methanesulfonyl chloride (11.9 µl, 0.154 mmol, 1.5 eq.) and heated to reflux for one night. After confirming the completion of the reaction with TLC, to the solution were added the solution ($THF:H_2O=2:1$) and NaOH (20.6 mg, 0.515 mmol, 5 eq.) and stirred at room temperature for 1 hour. The reaction solution was acidified by 10% HCl, extracted with ethylacetate, washed with water and brine, dried over $Na_2SO_4$ and evaporated. The obtained solid was column-chromatographed (n-hexane/ethyl acetate=2/1) to yield a yellow liquid.

IR (NaCl neat, $cm^{-1}$): 3349, 3236, 2956, 2921, 2850, 1689;
$^1$H NMR (400 MHz, $CDCl_3$): 7.27 (s, 1H), 7.10 (dd, 1H, J=17.6, 10.8 Hz), 6.97 (d, 1H, J=10.0 Hz), 5.88 (bs, 1H), 5.73 (d, 1H, J=17.6 Hz), 5.39 (d, 1H, J=10.8 Hz), 4.87 (bs, 1H), 4.25 (d, 2H, J=6.0 Hz), 3.00 (s, 3H), 1.40 (s, 9H)

Step 5: N-(4-aminomethyl-2-fluoro-6-vinylphenyl)methanesulfonamide (3-fluoro-4-methanesulfonylamino-5-vinyl-benzyl)-carbamic acid t-butyl ester (1 ml) was put into 25 ml round-bottom flask and dissolved in methylenechloride. To the solution was added trifluoroacetic acid (1 ml) and stirred for one night. After confirming the completion of the reaction with TLC, the reaction solution was concentrated under reduced pressure to yield a brown crude liquid (236.7 mg).

Step 6: N-4-[3-(4-t-butylbenzyl)ureidomethyl]-2-fluoro-6-vinylphenyl methane sulfonamide A 25 ml two-neck round bottom flask was filled with argon gas and the solution of 4-t-butylbenzylamine (59.3 µl, 0.338 mmol, 1 eq.) in methylenechloride was put into the flask. To the solution were added 4-dimethylaminopyridine (8.3 mg, 0.068 mmol, 0.2 eq.) and di-t-butyl dicarbonate (93.3 µl, 0.406 mmol, 1.2 eq.) and stirred at room temperature for 3 hours. The resulting solution was cooled to 0° C. and the solution of 3-fluoro-4-methanesulfonylamino-5-vinylbenzyl-ammonium, trifluoroacetate (121.1 mg, 0.338 mmol, 1 eq.) and triethylamine (94.2 µl, 0.676 mmol, 2 eq.) in methylenechloride was added. The mixture solution was stirred at room temperature for one night. After confirming the completion of the reaction with TLC, methylenechloride was removed under reduced pressure. The remain liquid was column-chromatographed (n-hexane/ethyl acetate=1/1 (only ethylacetate)) to yield a white solid (35 mg, 23.9%).

mp: 163-164° C.;

IR (KBr pellet, cm$^{-1}$): 3376, 3250, 3057, 2961, 1636, 1580, 1319, 1151;

$^1$H NMR (400 MHz, CD$_3$OD): 7.42 (d, 1H, J=1.6 Hz), 7.33 (d, 2H, J=8.4 Hz), 7.19 (d, 2H, J=8.4 Hz), 7.15 (dd, 1H, J=17.6, 11.2 Hz), 7.05 (dd, 1H, J=10.8, 1.6 Hz), 5.79 (d, 1H, J=17.6 Hz), 5.36 (d, 1H, J=11.2 Hz), 4.33 (s, 2H), 4.29 (s, 2H), 3.00 (s, 3H), 1.28 (s, 9H)

Example 3

N-{4-[3-(4-t-butylbenzyl)ureidomethyl]-2-ethynyl-6-fluorophenyl}methanesulfonamide

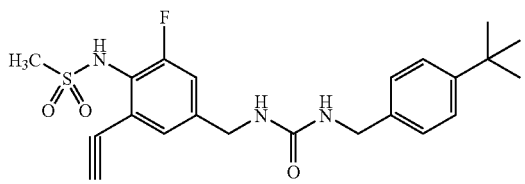

Step 1: (4-amino-3-fluoro-5-trimethylsilanylethynyl-benzyl)carbamic acid t-butyl ester The solution of (4-amino-3-fluoro-5-iodobenzyl) carbamic acid t-butyl ester (100 mg, 0.273 mmol, 1 eq.), dichloro(bis-triphenylphosphine), palladium (9.8 mg, 0.014 mmol, 0.05 eq.) and Copper iodide (2.6 mg, 0.014 mmol, 0.05 eq.) in THF was put into a 25 ml two-neck round bottom flask and stirred at room temperature for 30 minutes. To the solution were added triethylamine (114.2 µl, 0.819 mmol, 3 eq.) and (trimethylsilyl)acetylene (50.2 µl, 0.355 mmol, 1.3 eq.) and heated to reflux for one night. The reaction solution was concentrated under reduced pressure and column-chromatographed (n-hexane/ethyl acetate=5/1) to yield a brown liquid (84.0 mg, 91.4%).

IR (NaCl, neat, cm$^{-1}$): 3459, 3360, 2965, 2148, 1698;

$^1$H NMR (400 MHz, CDCl$_3$): 7.00 (d, 1H, J=0.8 Hz), 6.91 (dd, 1H, J=11.6, 0.8 Hz), 4.77 (bs, 1H), 4.36-3.91 (m, 2H), 4.15 (s, 2H), 1.46 (s, 9H), 0.27 (s, 9H).

Step 2: (3-ethynyl-5-fluoro-4-methanesulfonylami-nobenzyl)carbamic acid t-butyl ester A 25 ml two-neck round bottom flask was filled with argon gas, the solution of (4-amino-3-fluoro-5-trimethylsilanyl-ethynylbenzyl)carbamic acid t-butyl ester (80 mg, 0.238 mmol, 1 eq.) in methylenechloride was put into the flask and then cooled to 0° C. To the solution were added methanesulfonyl chloride (92.0 µl, 1.189 mmol, 5 eq.) and triethylamine (99.5 µl, 0.714 mmol, 3 eq.), and stirred at room temperature for one night. After confirming the completion of the reaction with TLC, the reaction was quenched with saturated NaHCO$_3$ solution. The resulting solution was extracted with methylene chloride, washed with saturated CuSO$_4$ solution, water and brine, dried over Na$_2$SO$_4$, filtered and concentrated under reduced pressure. The obtained solid was dissolved in the solution (THF:H$_2$O=2:1). To the solution was added NaOH (47.6 mg, 1.190 mmol, 5 eq.), stirred at room temperature for 3 hours and acidified by 10% HCl. The solution was extracted with ethylacetate, washed with water and brine, dried over Na$_2$SO$_4$, filtered and concentrated under reduced pressure. The obtained solid was column-chromatographed (n-hexane/ethyl acetate=5/1) to yield a brown solid (51.4 mg, 63.0%).

mp: 146-147° C.

IR (KBr pellet, cm$^{-1}$): 3420, 3288, 2979, 2933, 2112, 1691;

$^1$H NMR (400 MHz, CDCl$_3$): 7.17 (d, 1H, J=0.8 Hz), 7.05 (dd, 1H, J=10.8, 0.8 Hz), 6.38 (bs, 1H), 4.89 (bs, 1H), 4.20 (d, 2H, J=6.0 Hz), 3.40 (s, 1H), 3.18 (s, 3H), 1.39 (s, 9H).

Step 3: 3-ethynyl-5-fluoro-4-methanesulfonylami-nobenzylammonium; Trifluoroacetate (3-ethynyl-5-fluoro-4-methanesulfonylaminobenzyl)-carbamic acid t-butyl ester (301.6 mg, 0.881 mmol, 1 eq.) was put into 50 ml round-bottom flask and dissolved in methylenechloride. To the solution were added 10 drops of trifluoroacetic acid and stirred for one night. After confirming the completion of the reaction with TLC, the reaction solution was concentrated under reduced pressure to yield a brown crude liquid (564 mg).

Step 4: N-{4-[3-(4-t-butylbenzyl)ureidomethyl]-2-ethynyl-6-fluorophenyl}methanesulfonamide A 25 ml two-neck round bottom flask was filled with argon gas and the solution of 4-t-butylbenzylamine (83.0 µl, 0.473 mmol, 1 eq.) in methylenechloride was put into the flask. To the solution were added 4-dimethylaminopyridine (11.6 mg, 0.095 mmol, 0.2 eq.) and di-t-butyl dicarbonate (130.5 µl, 0.568 mmol, 1.2 eq.) and stirred at room temperature for 3 hours. The resulting solution was cooled to 0° C. and the solution of 3-ethynyl-5-fluoro-4-methanesulfonylaminoben-zyl ammonium, trifluoroacetate (168.5 mg, 0.473 mmol, 1 eq.), and triethylamine (131.9 µl, 0.946 mmol, 2 eq.) in methylenechloride was added. The mixture solution was stirred at room temperature for one night. After confirming the completion of the reaction with TLC, methylenechloride was removed under reduced pressure. The remain liquid was column-chromatographed (n-hexane/ethyl acetate=1/1) to yield a white solid (48.4 mg, 23.7%).

mp: 117-118° C.;

IR (KBr pellet, cm$^{-1}$): 3418, 3051, 2962, 2112, 1634, 1582, 1318, 1152;

$^1$H NMR (400 MHz, CD$_3$OD): 7.30 (d, 2H, J=8.4 Hz), 7.25 (d, 1H, J=2.0 Hz), 7.15 (d, 2H, J=8.4 Hz), 7.10 (dd, 1H, J=10.8, 2.0 Hz), 4.26 (s, 2H), 4.25 (s, 2H), 3.44 (s, 1H), 3.06 (s, 3H), 1.25 (s, 9H)

Example 4

N-{4-[3-(4-t-butylbenzyl)ureidomethyl]-5-chloro-2-vinylphenyl}methanesulfonamide

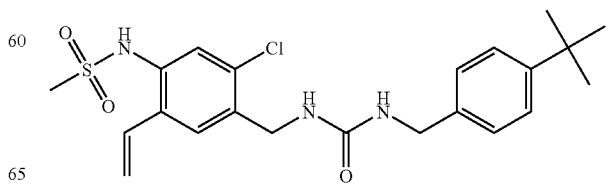

Step 1: (4-amino-2-chloro-5-vinylbenzyl)carbamic acid t-butyl ester

A dried 25 ml two-neck round bottom flask was filled with argon gas, the solution of Pd(PPh3)$_4$ (0.06 eq, 0.01 mmol, 11.09 mg) and LiCl (2.8 eq, 0.45 mmol, 18.99 mg) in DMF was added to the flask. To the solution were added (4-amino-2-chloro-5-iodo-benzyl)-carbamic acid t-butyl ester (60 mg, 0.16 mmol) and tributylvinyltin (1.5 eq, 0.24 mmol, 74.71 μl) and heated to reflux for 12 hours. After confirming the completion of the reaction with TLC, DMF was removed under reduced pressure and the residue was extracted with ethylacetate. The ethylacetate layer was washed with water and brine, dried over Na$_2$SO$_4$, filtered and concentrated under reduced pressure. The obtained liquid was column-chromatographed (n-hexane/ethyl acetate=5/1) to yield a deep yellow syrup (17.1 mg, substrate recovery-35.7 mg, 38.59%).

IR (NaCl neat, cm$^{-1}$): 3359, 3085, 2976, 1698, 760;
$^1$H NMR (400 MHz, CDCl$_3$): 7.19 (s, 1H), 6.65 (s, 1H), 6.60 (dd, 1H, J=17.2, 10.8 Hz), 5.55 (dd, 1H, J=17.2, 0.8 Hz), 5.27 (dd, 1H, J=10.8, 1.2 Hz), 4.83 (bs, 1H), 4.22 (d, 2H, J=6.0 Hz), 1.37 (s, 9H)

Step 2: (2-chloro-4-methanesulfonylamino-5-vinylbenzyl)carbamic acid t-butyl ester A dried 25 ml two-neck round bottom flask was filled with argon gas and the solution of (4-amino-2-chloro-5-vinyl-benzyl)-carbamic acid t-butyl ester (103.0 mg, 0.37 mmol) in methylenechloride was added to the flask and then cooled to 0° C. To the solution were added methanesulfonylchloride (5 eq, 1.83 mmol, 141.29 μl) and triethylamine (3 eq, 1.11 mmol, 154.71 μl) slowly and stirred at room temperature for 12 hours. After confirming the completion of the reaction with TLC, the reaction was quenched with NaHCO$_3$ solution. The resulting solution was extracted with methylenechloride, washed with CuSO$_4$, water and brine, dried over Na$_2$SO$_4$, filtered and concentrated under reduced pressure. The obtained liquid was diluted with the solution (THF:H$_2$O=2:1) and added NaOH (5 eq, 1.85 mmol, 74 mg). The solution was stirred for 1 hr and then confirmed the completion of the reaction with TLC. The reaction solution was acidified by 10% HCl, extracted with ethylacetate, washed with water and brine, dried over Na$_2$SO$_4$, filtered and concentrated under reduced pressure. The obtained liquid was column-chromatographed (n-hexane/ethyl acetate=3/1) to yield a white solid (103.9 mg, 79.03%).

mp: 136~138° C.;
IR (KBr pellet, cm$^{-1}$): 3353, 3025, 2983, 1683, 1322, 757;
$^1$H NMR (400 MHz, CDCl$_3$): δ7.42 (s, 1H), 7.39 (s, 1H), 6.76 (dd, 1H, J=17.2, 11.2 Hz), 6.69 (bs, 1H)

Step 3: N-(4-aminomethyl-5-chloro-2-vinylphenyl)methanesulfonamide

To a dried 25 ml round bottom flask was added (2-chloro-4-methanesulfonylamino-5-vinyl-benzyl)-carbamic acid t-butyl ester (103.9 mg, 0.29 mmol) and diluted with methylenechloride. To the solution were added 5-6 drops of CF$_3$COOH and stirred for 12 hours. After confirming the completion of the reaction with TLC, the resulting solution was concentrated under reduced pressure using toluene to yield a brownish syrup (98.1 mg, 130.74%).

$^1$H NMR (400 MHz, CD$_3$OD): δ 7.81 (s, 1H), 7.55 (s, 1H), 7.04 (dd, 1H, J=17.2, 10.8 Hz), 5.88 (d, 1H, J=17.2 Hz), 5.47 (d, 1H, J=10.8 Hz), 4.27 (s, 2H), 2.98 (s, 3H).

Step 4: N-{4-[3-(4-t-butylbenzyl)ureidomethyl]-5-chloro-2-vinylphenyl}methanesulfonamide A dried 25 ml two-neck round bottom flask was filled with argon gas and the solution of 4-t-butylbenzylamine (29.38 μl, 0.18 mmol) in methylene chloride was added to the flask. To the solution were added Boc$_2$O (1.5 eq, 0.27 mmol, 151.78 μl) and DMAP (0.2 eq, 0.09 mmol, 10.15 mg) slowly and stirred for 5 hours. After confirming for 1-t-butyl-4-isocyanatomethyl-benzene to be produced with TLC, to the solution were added N-(4-aminomethyl-5-chloro-2-vinyl-phenyl)-methanesulfonamide (1 eq, 0.18 mmol, 46.3 mg) and TEA (2 eq, 0.36 mmol, 50.17 μl) and stirred for 12 hours. After confirming the progress of reaction, the reaction solution was extracted with methylenechloride, washed with water and brine, dried over Na$_2$SO$_4$, filtered and concentrated under reduced pressure. The obtained liquid was column-chromatographed (n-hexane/ethyl acetate=1/1) to yield a white solid (15.5 mg, 19.18%).

mp: 140~142° C.;
IR (KBr pellet, cm$^{-1}$): 3366, 2961, 1635, 1313, 757;
$^1$H NMR (400 MHz, CDCl$_3$): δ 7.42 (s, 1H), 7.40 (s, 1H), 7.28 (d, 2H, J=8.4 Hz), 7.16 (d, 2H, J=8.4 Hz), 6.68 (dd, 1H, J=17.2, 11.2 Hz), 6.45 (bs, 1H), 5.60 (d, 1H, J=17.2 Hz), 5.41 (d, 1H, J=11.2 Hz), 4.36 (s, 2H), 4.27 (s, 2H), 2.93 (s, 3H), 1.23 (s, 9H).

Example 5

N-{4-[3-(4-t-butylbenzyl)ureidomethyl]-5-chloro-2-ethynyl phenyl}methanesulfonamide

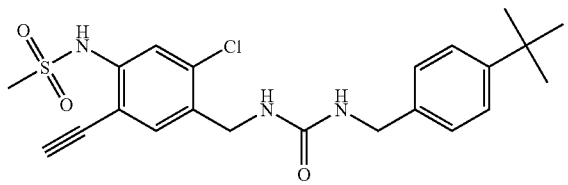

Step 1: (4-amino-2-chloro-5-trimethylsilanylethynyl-benzyl)carbamic acid t-butyl ester A dried 25 ml two-neck round bottom flask was filled with argon gas and the solution of (4-amino-2-chloro-5-iodo-benzyl)-carbamic acid t-butyl ester (60 mg, 0.16 mmol), CuI (0.05 eq, 0.008 mmol, 1.52 mg) and PdCl$_2$(PPh3)$_2$ in DMF was put into the flask. The solution was stirred at room temperature for 30 minutes. To the solution were added (TMS) acetylene (1.3 eq, 0.21 mmol, 29.39 mg) and triethylamine (3 eq, 0.48 mmol, 66.90 μl) and heated to reflux for 12 hours. After confirming the completion of the reaction with TLC, the resulting solution was extracted with ethylacetate, washed with water and brine, dried over Na$_2$SO$_4$, filtered and concentrated under reduced pressure. The obtained liquid was column-chromatographed (n-hexane/ethyl acetate=6/1) to yield an orange colored solid (44.9 mg, 81.17%).

mp: 104~106° C.;
IR (KBr pellet, cm$^{-1}$): 3356, 2962, 2143, 1698, 843;
$^1$H NMR (400 MHz, CDCl$_3$): 7.17 (s, 1H), 6.61 (s, 1H), 4.77 (bs, 1H), 4.14 (d, 2H, J=6.0 Hz), 1.35 (s, 9H), 0.15 (s, 9H).

Step 2: (2-chloro-5-ethynyl-4-methanesulfonylaminobenzyl) carbamic acid t-butyl ester A dried 25 ml two-neck round bottom flask was filled with argon gas. The solution of (4-amino-2-chloro-5-trimethylsilanylethynyl-benzyl)-carbamic acid t-butyl ester (225.3 mg, 0.64 mmol) in methylenechloride was put into the flask and then cooled to 0° C. To the solution were added methanesulfonylchloride (5 eq, 3.20 mmol, 247.60%) and triethylamine (3 eq, 1.92 mmol, 267.61 µl) slowly and stirred at room temperature for 12 hours. After confirming the completion of the reaction with TLC, the reaction was quenched with NaHCO$_3$ solution. The reaction solution was extracted with methylenechloride, washed with CuSO$_4$, water and brine, dried over Na$_2$SO$_4$, filtered and concentrated under reduced pressure. The obtained liquid was diluted with the solution (THF:H$_2$O=2:1) and to the solution was added NaOH (5 eq, 3.20 mmol, 128 mg). The mixture was stirred for 1 hour. After confirming the completion of the reaction with TLC, the reaction solution was acidified by 10% HCl, extracted with ethylacetate, washed with water and brine, dried over Na$_2$SO$_4$, filtered and concentrated under reduced pressure. The obtained liquid was column-chromatographed (n-hexane/ethyl acetate=3/1) to yield a white solid (182.6 mg, 79.70%).

mp: 138~140° C.
IR (KBr pellet, cm$^{-1}$): 3371, 3025, 2987, 1694, 1327, 701;
$^1$H NMR (400 MHz, CDCl$_3$): δ 7.53 (s, 1H), 7.40 (s, 1H), 6.99 (bs, 1H), 5.06 (s, 1H), 4.23 (d, 2H, J=6.0 Hz), 2.95 (s, 3H), 1.35 (s, 9H).

Step 3: N-(4-aminomethyl-5-chloro-2-ethynylphenyl)methanesulfonamide

A dried 25 ml two-neck round bottom flask was filled with argon gas and the solution of (2-chloro-5-ethynyl-4-methanesulfonylamino-benzyl)-carbamic acid t-butyl ester (182.6 mg, 0.51 mmol) in methylenechloride was put into the flask. To the solution were added 5~6 drops of CF$_3$COOH and stirred for 12 hours. After confirming the completion of the reaction with TLC, the resulting solution was concentrated under reduced pressure using toluene to yield brown syrup (98.1 mg, 114.23%).
$^1$H NMR (400 MHz, CD$_3$OD): δ 7.69 (s, 1H), 7.66 (s, 1H), 4.22 (s, 2H), 4.04 (s, 1H), 3.03 (s, 3H).

Step 4: N-{4-[3-(4-t-butylbenzyl)ureidomethyl]-5-chloro-2-ethynyl phenyl}methanesulfonamide A dried 25 ml two-neck round bottom flask was filled with argon gas and the solution of 4-t-butyl-benzylamine (44.08 µl, 0.27 mmol) in methylenechloride was put into the flask. To the solution were added Boc$_2$O (1.5 eq, 0.41 mmol, 93.14 µl) and DMAP (0.2 eq, 0.05 mmol, 6.59 mg) slowly and stirred for 5 hours. After confirming for 1-t-butyl-4-isocyanatomethyl-benzene to be produced with TLC, to the solution were added N-(4-aminomethyl-5-chloro-2-ethynyl-phenyl)-methanesulfonamide (1 eq, 0.27 mmol, 70 mg) and TEA (2 eq, 0.54 mmol, 75.27 µl) and stirred for 12 hours. After confirming the progress of reaction with TLC, the reaction solution was extracted with methylenechloride, washed with water and brine, dried over Na$_2$SO$_4$, filtered and concentrated under reduced pressure. The obtained liquid was column-chromatographed (n-hexane/ethyl acetate=1/1) to yield a white solid (20.20 mg, 16.73%).

mp: 116~118° C.
IR (KBr pellet, cm$^{-1}$): 3282, 3025, 2961, 2202, 1636, 1329, 762;
$^1$H NMR (400 MHz, CDCl$_3$): δ 7.53 (s, 1H), 7.46 (s, 1H), 7.27 (d, 2H, J=8.4 Hz) 7.14 (d, 2H, J=8.0 Hz), 6.91 (bs, 1H), 4.30 (s, 2H), 4.25 (s, 2H) 3.44 (s, 3H), 3.02 (s, 1H), 2.95 (s, 3H), 1.22 (s, 9H).

Example 6

N-(4-{1-(R)-[3-(4-t-butylbenzyl)ureido]ethyl}-2-vinylphenyl)methanesulfonamide

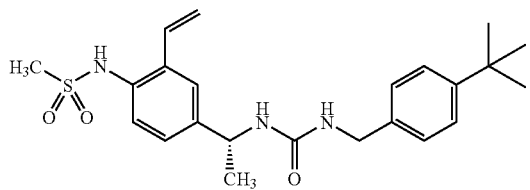

Step 1: (R)-[1-(4-nitrophenyl)ethyl]carbamic acid t-butyl ester (R)-methyl-4-nitrobenzylamine HCl (50 mg, 0.25 mmol) was put into 25 ml round-bottom flask and dissolved in the saturated solution (NaHCO$_3$:CH$_2$Cl$_2$=1:1). To the solution was added di-t-butyl dicarbonate (135 mg, 0.60 mmol, 2.5 eq) and stirred for 3 hours. The reaction mixture was diluted with methylenechloride, washed with water and brine, dried over Na$_2$SO$_4$ and concentrated under reduced pressure. The obtained liquid was column-chromatographed (n-hexane/ethyl acetate=10/1) to yield a pale yellow solid (62.0 mg, 94.38%).

[α]$^{21.6}_D$: −43.66° C. (c 1.33, CHCl$_3$);
IR (NaCl neat, cm$^{-1}$): 3403, 3332, 2977, 2932, 1697, 1522, 1347;
$^1$H NMR (400 MHz, CDCl$_3$): 8.20 (d, 2H, J=8.8 Hz), 7.47 (d, 2H, J=8.8 Hz), 4.91 (s, 1H), 4.85 (s, 1H), 1.46 (d, 3H, J=6.8 Hz), 1.42 (s, 9H).

Step 2: (R)-[1-(4-aminophenyl)ethyl]carbamic acid t-butyl ester (R)-[1-(4-nitrophenyl)ethyl]carbamic acid t-butyl ester (25 mg, 0.09 mmol) was put into 25 ml round-bottom flask and dissolved in methanol. To the solution was added Pd (7 mg, 30% of substrate. Air in the flask was displaced with hydrogen gas and stirred for 2 hours. After confirming the completion of the reaction with TLC, Pd/C was filtered off and methanol was removed under reduced pressure to yield transparent yellow liquid (21.7 mg, 91.93%).

[α]$^{22.0}_D$: −69.75° C. (c 1.02, CHCl$_3$);
IR (NaCl neat, cm$^{-1}$): 3353, 3035, 2974, 2937, 1695, 1623, 1366;
$^1$H NMR (400 MHz, CDCl$_3$): 7.10 (d, 2H, J=8.0 Hz), 6.40 (d, 2H, J=8.0 Hz), 4.70 (s, 2H), 3.60 (s, 2H), 1.42 (s, 12H).

Step 3: (R)-[1-(4-amino-3-iodophenyl)ethyl]carbamic acid t-butyl ester

The solution of [1-(4-amino-phenyl)-ethyl]-carbamic acid t-butyl ester (141.1 mg, 0.60 mmol, 1 eq.) in methylenechloride was put into 50 ml two-neck round bottom flask. To the solution was added iodomonochloride (106.6 mg, 0.66 mmol, 1.1 eq.) and stirred at room temperature for 1 hour. After confirming the completion of the reaction with TLC, the resulting solution was washed with saturated $Na_2S_2O_3$ solution, water and brine, dried over $Na_2SO_4$, filtered, and evaporated. The obtained liquid was column-chromatographed (n-hexane/ethyl acetate=5/1) to yield brown liquid (102.7 mg).

$[\alpha]^{23}_D$: +55.03° C. (c 0.60, $CHCl_3$);
IR (NaCl neat, $cm^{-1}$): 3423, 3343, 2973, 296, 1692, 1498, 1167;
$^1$H NMR (400 MHz, $CDCl_3$): 7.48 (d, 1H, J=1.6 Hz), 7.01 (d, 1H, J=8.4 Hz), 6.62 (d, 1H, J=8.4 Hz), 4.63-4.57 (m, 2H), 1.35 (s, 9H), 1.32 (d, 3H, J=6.8 Hz).

Step 4: (R)-[1-(4-amino-3-ethenylphenyl)ethyl]carbamic acid t-butyl ester

A dried 25 ml two-neck round bottom flask was filled with argon gas and the solution of tetrakis(triphenyl phosphine) palladium(0) (27.9 mg, 0.02 mmol, 0.06 eq.) and lithium chloride (47.7 mg, 1.13 mmol, 2.8 eq.) in DMF was put into the flask. To the solution were added [1-(4-amino-3-iodophenyl)ethyl]carbamic acid t-butyl ester (145.5 mg, 0.40 mmol, 1 eq.) and tributylvinyltin (176.2 μl, 0.60 mmol, 1.5 eq.) and heated to 90° C. to reflux for one night. After confirming the completion of the reaction with TLC, DMF was removed under reduced pressure and extracted with methylenechloride. The methylenechloride layer was washed with water and saturated brine, dried over $Na_2SO_4$, filtered and concentrated under reduced pressure. The obtained liquid was column-chromatographed (n-hexane/ethyl acetate=5/1) to yield brown liquid (76.3 mg, 72.3%).

$[\alpha]^{23}_D$: +59.07° C. (c 0.43, $CHCl_3$);
IR (NaCl neat, $cm^{-1}$): 3369, 2972, 2922, 2852, 1687;
$^1$H NMR (400 MHz, $CDCl_3$): 7.14 (d, 1H, J=1.6 Hz), 6.96 (dd, 1H, J=8.4, 1.6 Hz), 6.69 (dd, 1H, J=17.6, 11.2 Hz), 6.58 (d, 1H, J=8.4 Hz), 5.56 (dd, 1H, J=17.6, 1.6 Hz), 5.25 (dd, 1H, J=11.2, 1.6 Hz), 4.64 (bs, 2H), 1.37-1.35 (m, 12H).

Step 5: (R)-[1-(4-methanesulfonylamino-3-ethenylphenyl)ethyl]carbamic acid t-butyl ester A 100 ml two-neck round bottom flask was filled with argon gas and the solution of (R)-[1-(4-amino-3-ethenylphenyl)ethyl]carbamic acid t-butyl ester (358.5 mg, 1.366 mmol, 1 eq.) in methylenechloride was put into the flask and then cooled to 0° C. To the solution was added methanesulfonic anhydride (285.7 mg, 1.640 mmol, 1.2 eq.) and followed by adding pyridine (328.4 μl, 4.098 mmol, 2 eq.) and stirring for 1 hour. After confirming the completion of the reaction with TLC, to the solution was added saturated $NaHCO_3$ solution and stirred for 5 minutes. The resulting solution was extracted with methylenechloride, washed with 5% HCl, sat. $NaHCO_3$ solution, water and brine, dried over $Na_2SO_4$, filtered and evaporated. The obtained solid was column-chromatographed (n-hexane/ethyl acetate=2/1) to yield pale yellow solid (169.0 mg, 47.2%).

$[\alpha]^{20}_D$: +34.74° C. (c 0.43, $CHCl_3$);
IR (KBr pellet, $cm^{-1}$): 3361, 3265, 3080, 2978, 2929, 2851, 1682;
$^1$H NMR (400 MHz, $CDCl_3$): 7.36 (d, 1H, J=8.4 Hz), 7.34 (d. 1H, J=2.0 Hz), 7.17 (dd, 1H, J=8.4, 2.0 Hz), 6.83 (dd, 1H, J=17.2, 10.8 Hz), 6.35 (bs, 1H), 5.66 (d, 1H, J=17.2 Hz), 5.40 (d, 1H, J=10.8 Hz), 4.82-4.63 (m, 2H), 2.92 (s, 3H), 1.38-1.36 (m, 12H).

Step 6: (R)-[1-(4-methanesulfonylamino-3-ethenylphenyl)ethyl]ammonium trifluoro-acetate

[1-(4-methanesulfonylamino-3-vinylphenyl)ethyl]carbamic acid t-butyl ester (158.4 mg, 0.465 mmol, 1 eq.) was put into 100 ml round-bottom flask and dissolved in methylenechloride. To the solution was added trifluoroacetic acid (179.2 μl, 2.326 mmol, 5 eq.) and stirred for one night. After confirming the completion of the reaction with TLC, the reaction solution was concentrated under reduced pressure to yield brown crude liquid (236.7 mg).

Step 7: N-(4-{1-(R)-[3-(4-t-butylbenzyl)ureido]ethyl}-2-vinylphenyl)methanesulfonamide A 25 ml two-neck round bottom flask was filled with argon gas and the solution of 4-t-butylbenzylamine (14.8 μl, 0.084 mmol, 1 eq.) in methylenechloride was put into the flask. To the solution were added 4-dimethylaminopyridine (2.1 mg, 0.017 mmol, 0.2 eq.) and di-t-butyl dicarbonate (23.2 μl, 0.101 mmol, 1.2 eq.) and stirred at room temperature for 3 hours. The resulting solution was cooled to 0° C. and the solution of [1-(4-methanesulfonylamino-3-ethenylphenyl)ethyl]ammoniumtrifluoro-acetate (30 mg, 0.084 mmol, 1 eq.) and triethylamine (23.4 μl, 0.168 mmol, 2 eq.) in methylenechloride was added. The mixture solution was stirred at room temperature for one night. After confirming the completion of the reaction with TLC, methylenechloride was removed under reduced pressure. The remain liquid was column-chromatographed (n-hexane/ethyl acetate=1/1) to yield a pale yellow solid (21.8 mg, 60.4%).

mp: 105.1-105.8° C.;
$[\alpha]^{23}_D$: −5.00° C. (c 0.46, $CHCl_3$);
IR (KBr pellet, $cm^{-1}$): 3418, 3029, 2963, 2926, 2869, 1634;
$^1$H NMR (400 MHz, $CDCl_3$): 7.33 (d, 1H, J=1.6 Hz), 7.30 (d, 1H, J=8.4 Hz), 7.26 (d, 2H, J=8.0 Hz), 7.11-7.08 (m, 3H), 6.81 (dd, 1H, J=17.2, 10.8 Hz), 6.49 (bs, 1H), 5.62 (d, 1H, J=17.2 Hz), 5.37 (d, 1H, J=10.8 Hz), 4.77 (q, 1H, J=6.8 Hz), 4.64 (bs, 2H), 4.24 (s, 2H), 2.89 (s, 3H), 1.34 (d, 3H, J=6.8 Hz), 1.23 (s, 9H).

Example 7

(R)—N-(4-{1-[3-(4-tert-Butyl-benzyl)-ureido]-ethyl}-2-fluoro-6-vinyl-phenyl)-methanesulfonamide

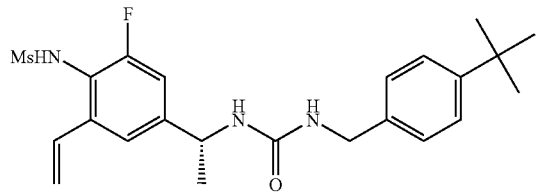

Step 1: 1-(4-Amino-3-fluorophenyl)ethanone

A 25 ml two neck round-bottom flask was filled with Ar gas and the solution of 2-fluoro-4-iodophenylamine (1500 mg, 6.33 mmol) in DMF, palladium (II) acetate (0.19 mmol, 42.62 mg), 1,3-bisdiphenyl phosphinopropane (0.06 eq, 0.38 mmol, 156.65 mg), Thallium (I) acetate (6.96 mmol, 1834.19 mg), butyl vinyl ether (2 eq, 12.66 mmol, 1.64 ml) were put into the flask. The reaction mixture was heated and stirred for 15 hr. The reaction mixture was poured into the THF solution, and then 10% HCl was added slowly. The reaction mixture was extracted with ethyl acetate (300×3), washed with $H_2O$ and brine. The combined organic solution was dried with $Na_2SO_4$ and then purified with column chromatography (n-Hx:EA=3:1) to yield a pale yellow solid (343.0 mg, 35.40%).

mp: 77~79° C.;

IR (KBr pellet, $cm^{-1}$): 3373, 3326, 1663, 1296; $^1$H NMR (400 MHz, $CDCl_3$): δ 7.53 (m, 2H), 6.69 (m, 1H), 3.41 (s, 2H), 2.43 (s, 3H).

Step 2: 1-(4-Amino-3-fluoro-5-iodophenyl)ethanone 1-(4-amino-3-fluorophenyl)ethanone (0.30 mmol, 45.6 mg) was added in the acetonitrile, and then NIS (0.33 mol, 73.73 mg) was added. A reaction mixture was stirred for 12 hr. A reaction mixture was quenched by sodium thiosulfate. A reaction mixture was extracted with EtOAC and $H_2O$, a combined organic layer was washed with brine and dried with $Na_2SO_4$ and then concentrated in vacuo. The remain layer was purified with column chromatography (n-Hx:EtOAc=7:1) to yield brownish solid (53.92 mg, 64.43%).

mp: 124~126° C.;

IR (KBr pellet): 3455, 3331, 3073, 2921, 1659, 1259 $cm^{-1}$;

$^1$H NMR (400 MHz, $CDCl_3$): δ 8.01 (dd, 1H, J=1.6, 1.2 Hz), 7.65 (dd, 1H, J=11.6, 2.0 Hz), 4.61 (bs, 2H), 2.46 (s, 3H).

Step 3: 2-Methylpropane-2-sulfinic Acid [1-(4-amino-3-fluoro-5-iodophenyl)ethyl]amide 1-(4-Amino-3-fluoro-5-iodophenyl)ethanone (0.36 mmol, 100 mg), $Ti(OEt)_4$ (0.59 mmol, 122.68 µl), (R)-(+)-2-methyl-2-propane sulfinamide (0.32 mmol, 39.27 mg) was added to THF solution. A reaction mixture was heated and stirred for 12 hr. After confirming the completion of the reaction with TLC, a reaction mixture was cooled down to −40° C. $NaBH_4$ (1.19 mmol, 45.08 mg) was added into the reaction mixture. A reaction mixture was stirred for 12 hr at −40° C. MeOH was added into the reaction mixture. The reaction mixture was heated to room temperature. A reaction mixture was filtered with Celite. The filterate was extracted with EtOAC, washed with $H_2O$ and brine, dried with $Na_2SO_4$ and then concentrated in vacuo. The remain layer was purified with column chromatography (n-Hexane:EtOAc=3:1) to yield brownish syrup (29.1 mg, 20.30%).

$[α]_D^{20}$: −6.0 ($CHCl_3$, c 0.24);

IR (KBr pellet): 3322, 3211, 2974, 1491, 1051, 717 $cm^{-1}$;

$^1$H NMR (400 MHz, $CDCl_3$): δ 7.34 (s, 1H), 6.96 (dd, 1H, J=11.2, 2.0 Hz), 4.34 (qd, 1H, J=6.4, 2.8 Hz), 3.33 (d, 1H, J=2.0 Hz), 1.41 (d, 3H, J=6.4 Hz), 1.18 (s, 9H).

Step 4: 4-(1-Aminoethyl)-2-fluoro-6-iodophenylamine 2-methylpropane-2-sulfinic acid [1-(4-amino-3-fluoro-5-iodophenyl)ethyl]amide (0.07 mmol, 29.1 mg) was added to MeOH 1 ml. 4N HCl in 0.25 ml of 1,4-dioxane was added. A reaction mixture was stirred for 12 hr. A reaction mixture was concentrated in vacuo. A residue was filtered with glass filter. A filterated was concentrated in vacuo to yield brownish solid (31.2 mg).

mp: 180~182° C.;

$[α]_D^{20}$: +3.27 ($CHCl_3$, c 0.41); IR (KBr pellet): 3354, 3018, 2966, 1283, 756 $cm^{-1}$;

$^1$H NMR (400 MHz, $CDCl_3$): δ 7.72 (s, 1H), 7.35 (dd, 1H, J=11.2, 2.0 Hz), 4.41 (q, 1H, J=6.8 Hz), 1.58 (d, 3H, J=6.8 Hz), 1.30 (s, 3H).

Step 5: [1-(4-Amino-3-fluoro-5-iodophenyl)ethyl]carbamic acid tert-butylester

A 25 ml two-necked flask was filled with argon gas and the 4-(1-aminoethyl)-2-fluoro-6-iodophenylamine (0.18 mmol, 50.0 mg) was dissolved in THF. $BOC_2O$ (0.20 mol, 45.18 mg), DMAP (0.02 mol, 2.20 mg), and TEA (0.23 mol, 32.61 mg) was added. A reaction mixture was stirred for 12 hr. A reaction mixture was extracted with EtOAc, washed with $H_2O$ and brine, dried with $Na_2SO_4$, and concentrated in vacuo. A residue was purified with column chromatography (n-Hexane:EtOAc=7:1) to yield solid (65.9 mg, 94.44%).

mp: 88~90° C.;

$[α]_D^{20}$: 33.35 ($CHCl_3$, c 2.98);

IR (KBr pellet): 3364, 3026, 2958, 1696, 1169 $cm^{-1}$;

$^1$H NMR (400 MHz, $CDCl_3$): δ 7.31 (s, 1H), 6.90 (d, 1H, J=11.6 Hz), 4.72 (s, 1H), 4.59 (s, 1H), 3.76 (bs, 2H), 1.38 (s, 9H), 1.3 (d, 3H, J=6.8 Hz).

Step 6: [1-(4-Amino-3-fluoro-5-vinylphenyl)ethyl]carbamic acid tert-butylester $Pd(PPh_3)_4$ (0.01 mmol, 11.79 mg) and LiCl (0.48 mmol, 20.58 mg) were added DMF under argon atmosphere. [1-(4-Amino-3-fluoro-5-vinylphenyl)ethyl]carbamic acid tert-butyl ester (0.17 mmol, 65.9 mg) and tributylvinyltin (0.25 mmol, 74.52 µl) were added. A reaction mixture was stirred for 12 hr in reflux. A reaction solvent was removed in vacuo. A reaction mixture was extracted with EtOAc, washed with $H_2O$ and brine, dried with $Na_2SO_4$, and concentrated in vacuo. A residue was purified with column chromatography (n-Hexane:EtOAc=7:1) to yield yellow solid (23.4 mg, 47.06%).

mp: 59~61° C.;

$[α]_D^{20}$: +47.0 ($CHCl_3$, c 0.10);

IR (KBr pellet): 3357, 3088, 2975, 1696, 1640, 1168 $cm^{-1}$;

$^1$H NMR (400 MHz, $CDCl_3$): δ 6.93 (s, 1H), 6.81 (dd, 1H, J=11.6, 2.0 Hz), 6.65 (dd, 1H, J=17.2, 11.2 Hz), 5.29 (dd, 1H, J=11.2, 1.2 Hz), 4.64 (s, 1H), 4.61 (s, 1H), 3.66 (bs, 2H), 1.35 (s, 12H).

Step 7: [1-(3-Fluoro-4-methanesulfonylamino-5-vinylphenyl)ethyl]carbamic acid tert-butyl ester A 25 ml two-necked flask was filled with argon gas and the [1-(4-Amino-3-fluoro-5-vinylphenyl)ethyl]carbamic acid tert-butyl ester (0.08 mmol, 23.4 mg) was added methylene chloride. The reaction mixture was cooled down to 0° C. Methanesulfonyl chloride (0.40 mmol, 32.32 mmol) and TEA (0.24 mmol, 33.45 mg) was added into the reaction mixture. A reaction mixture was heated room temperature. A reaction mixture was quenched by adding $NaHCO_3$ solution. A reaction mixture was extracted with $CH_2Cl_2$. A combined organic layer washed with $CuSO$, $H_2O$ and brine, dried with $Na_2SO_4$, and concentrated in vacuo. A residue was added into the $THF:H_2O$=2:1 soln. NaOH (0.40 mmol, 16 mg) was added. A reaction mixture was stirred for 12 hr. After confirming the completion of the reaction with TLC, the reaction mixture was acidified with 10% HCl soln. The reaction mixture was stirred for 12 hr. The reaction mixture was extracted with EtOAc, washed with $H_2O$ and brine, dried with $Na_2SO_4$, and concentrated in vacuo. A residue was purified with column chromatography (n-Hexane:EtOAc=7:1) to yield brownish syrup (20.2 mg, 75.0%).

$[\alpha]_D^{20}$: +110.0 (CHCl$_3$, c 0.05);

IR (KBr pellet): 3235, 2977, 1685, 1156 cm$^{-1}$;

$^1$H NMR (400 MHz, CDCl$_3$): δ 7.28 (s, 1H), 7.10 (dd, 1H, J=18.0, 11.2 Hz), 6.95 (d, 1H, J=10.4 Hz), 6.16 (s, 1H), 5.73 (d, 1H, J=17.6 Hz), 5.37 (d, 1H, J=11.2 Hz), 4.80 (s, 1H), 4.69 (s, 1H), 2.99 (s, 3H), 1.35 (s, 12H).

Step 8: N-[4-(1-Aminoethyl)-2-fluoro-6-vinylphenyl]methanesulfonamide

[1-(3-fluoro-4-methanesulfonylamino-5-vinyl phenyl)ethyl]carbamic acid tert-butyl ester (0.06 mmol, 20.2 mg) was dissolved in methylene chloride, 5~6 drops of CF$_3$COOH were added. A reaction mixture was stirred for 12 hr. A toluene was added. The reaction mixture was concentrated in vacuo to yield brownish syrup (20.8 mg, 100.0%).

$^1$H NMR (400 MHz, CD$_3$OD): δ 7.60 (s, 1H), 7.25 (dd, 1H, J=10.4, 2.0 Hz), 7.16 (dd, 1H, J=18.0, 11.2 Hz), 5.89 (d, 1H, J=17.6 Hz), 5.43 (d, 1H, J=11.2 Hz), 4.48 (q, 1H, J=6.8 Hz), 3.02 (s, 3H), 1.61 (d, 3H, J=6.8 Hz).

Step 9: N-(4-{1-[3-(4-tert-Butylbenzyl)ureido]ethyl}-2-fluoro-6-vinylphenyl)methanesulfonamide A 25 ml two-necked flask was filled with argon gas and the 4-tert-Butylbenzylamine (2 eq., 35.10 µl, 0.22 mmol) was added in the Methylene chloride. BOC$_2$O (1.5 eq., 0.17 mmol, 37.95 µl) and DMAP (0.2 eq., 0.02 mmol, 2.69 mg) were slowly added. A reaction mixture was stirred for 5 hr. After the confirming the synthesis of 1-tert-Butyl-4-isocyanatomethylbenzene, N-[4-(1-Amino-ethyl)-2-fluoro-6-vinyl-phenyl]-methanesulfonamide (0.11 mmol, 40.0 mg) and TEA (2 eq., 0.58 mmol, 80.84 µl) were added. A reaction mixture was stirred for 12 hr. After the confirming the completion of reaction with TLC, The reaction mixture was extracted with methylene chloride, washed with H$_2$O and brine, dried with Na$_2$SO$_4$, and concentrated in vacuo. A residue was purified with column chromatography (n-Hexane:EtOAc=1:1) to yield white solid (21.7 mg, 27.56%).

mp: 89~91° C.;

$[\alpha]_D^{20}$: -8.34 (CHCl$_3$, c 0.49);

IR (KBr pellet): 337, 3092, 2963, 1636, 1154 cm$^{-1}$;

$^1$H NMR (400 MHz, CDCl$_3$): δ 7.29 (d, 2H, J=8.0 Hz), 7.27 (s, 1H), 7.13 (d, 2H, J=8.0 Hz), 7.09 (dd, 1H, J=17.6, 11.2 Hz), 6.91 (d, 1H, J=10.0 Hz), 6.41 (s, 1H), 5.71 (d, 1H, J=17.6 Hz), 5.37 (d, 1H, J=11.2 Hz), 4.79 (q, 1H, J=6.0 Hz), 4.24 (s, 2H), 2.99 (s, 3H), 1.33 (d, 3H, J=6.8 Hz), 1.26 (s, 9H).

Example 8

N-{4-[3-(4-tert-Butyl-benzyl)-ureidomethyl]-2-methyl-6-vinyl-phenyl}-methanesulfonamide

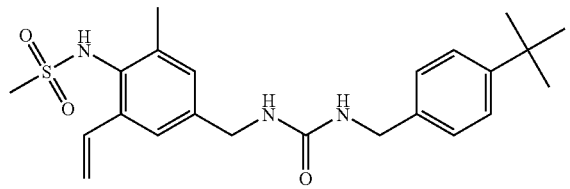

Step 1: 4-Amino-3-methylbenzonitrile 4-iodo-2-methylaniline (2000 mg, 8.58 mmol) and cyanide (1.15 g, 12.87 mmol, 1.5 eq) were added pyridine. A reaction mixture was heated to 150-160° C., stirred for 12 hr. A reaction mixture was diluted with methylene chloride. A diluted solution was washed with copper sulfate for several times. A mixture was washed with H$_2$O (2 times) and brine, and then dried with Na$_2$SO$_4$. A residue was purified with column chromatography (n-Hexane:EtOAc=2:1) to yield solid (786.5 mg, 69.34%).

mp: 78~80° C.;

IR (NaCl neat, cm$^{-1}$): 3403, 3335, 3220, 2942, 2220;

$^1$H NMR (400 MHz, CDCl$_3$): 7.24 (m, 2H), 6.57 (d, 1H, J=8.4 Hz), 4.03 (bs, 2H), 2.08 (s, 9H).

Step 2: 4-Amino-3-iodo-5-methylbenzonitrile

4-Amino-3-methyl-benzonitrile (786.5 µl, 5.95 mmol) and ICl (1.1 eq, 6.55 mmol, 1.06 g) was added to methylene chloride. A reaction mixture was stirred for 12 hr. A reaction mixture was quenched by adding sodium thiosulfate solution. A aqueous solution was extracted with MC. A combined organic solution was washed with H$_2$O and brine, dried with Na$_2$SO$_4$ and concentrated in vacuo. A residue was purified with column chromatography (n-Hx:EA=3:1) to yield solid (600.6 mg, 39.11%).

mp: 131~133° C.;

IR (KBr pellet, cm$^{-1}$): 3462, 3366, 2923, 2214, 1623;

$^1$H NMR (400 MHz, CDCl$_3$): δ7.22 (d, 1H, J=2.0 Hz), 7.21 (m, 1H), 2.16 (s, 3H)

Step 3: (4-Amino-3-iodo-5-methylbenzyl)carbamic acid tert-butyl ester

4-Amino-3-iodo-5-methylbenzonitrile (200 mg, 0.77 mmol) was dissolved in THF at 0° C. After Borane-THF complex (4 eq, 3.10 mmol, 3.10 ml) was slowly added into the reaction mixture, a reaction temperature was heated to reflux. The reaction mixture was stirred for 12 hr with reflux. After confirming the completion of the reaction, MeOH was added. The mixture was stirred for 4 hrs. The reaction solvent was removed in vacuo. A residue was extracted with Ethyl acetate, washed with H$_2$O and brine, dried with Na$_2$SO$_4$ and concentrated in vacuo to yield 4-Aminomethyl-2-iodo-6-methylphenylamine (194 mg).

4-Aminomethyl-2-iodo-6-methyl-phenylamine (195 mg, 0.76 mmol) was dissolved in THF, and then BOC$_2$O (1.1 eq, 0.21 mmol, 47.48 ml) was slowly added. The reaction mixture was stirred for 12 hr. A reaction mixture was extracted with Ethyl acetate, washed with H$_2$O and brine, dried with Na$_2$SO$_4$, concentrated in vacuo. A residue was purified with column chromatography (n-Hx:EA=5:1) to obtain a solid (73.2 mg, 34.77%).

mp: 135~137° C.;

IR (KBr pellet, cm$^{-1}$): 3354, 2995, 1675, 1617, 726;

$^1$H NMR (400 MHz, CDCl$_3$): δ7.38 (s, 1H), 6.90 (s, 1H), 4.78 (s, 1H), 4.08 (d, 2H, J=5.2 Hz), 4.01 (bs, 2H), 2.16 (s, 3H), 1.42 (s, 9H)

Step 4: (4-Amino-3-methyl-5-vinylbenzyl)carbamic acid tert-butyl ester

Pd(PPh$_3$)$_4$ (0.06 eq, 0.017 mmol, 19.41 mg) and LiCl (2.8 eq, 0.74 mmol, 33.23 mg) was dissolved in DMF. (4-Amino-3-iodo-5-methylbenzyl)carbamic acid tert-butyl ester (100 mg, 0.28 mmol) and Tributylvinyltin (1.5 eq, 0.41 mmol, 121.08 μl) were added into the reaction mixture. The reaction mixture was stirred for 12 hr in reflux. The reaction mixture was purified according to a similar procedure to step 3 to obtain solid (61.8 mg, 85.34%).

IR (NaCl neat, cm$^{-1}$): 3373, 2965, 1697, 1632;

$^1$H NMR (400 MHz, CDCl$_3$): δ 6.99 (s, 1H), 6.85 (s, 1H), 6.69 (dd, 1H, J=17.2, 10.8 Hz), 5.53 (dd, 1H, J=17.2, 1.6 Hz), 5.24 (dd, 1H, J=10.8, 1.6 Hz), 4.68 (bs, 1H), 4.10 (d, 2H, J=5.2 Hz), 3.70 (bs, 2H), 2.08 (s, 3H), 1.38 (s, 9H)

Step 5: (4-Methanesulfonylamino-3-methyl-5-vinyl-benzyl)carbamic acid tert-butyl ester (4-Amino-3-methyl-5-vinyl-benzyl)-carbamic acid tert-butyl ester (30.9 mg, 0.12 mmol), Methanesulfonyl chloride (10 eq, 1.2 mmol, 91 μl) and Triethylamine (6 eq, 0.36 mmol, 50.17) were added to Methylene chloride. The reaction mixture was stirred for 12 hr. A reaction mixture was purified with similar procedure to step 4 of example 8 to obtain syrup (9.5 mg, 23.70%).

IR (NaCl neat, cm$^{-1}$): 3371, 2961, 1697, 1513, 1316;

$^1$H NMR (400 MHz, CDCl$_3$): δ 7.27 (s, 1H), 7.06 (s, 1H), 7.01 (dd, 1H, J=17.6, 11.2 Hz), 5.80 (s, 1H), 5.68 (dd, 1H, J=17.7, 0.8 Hz), 5.33 (dd, 1H, J=11.2, 0.8 Hz), 4.79 (s, 1H), 4.22 (d, 2H, J=6.0 Hz), 2.98 (s, 3H), 2.36 (s, 3H), 1.40 (s, 9H).

Step 6: N-(4-Aminomethyl-2-methyl-6-vinyl-phenyl)-methanesulfonamide (4-Methanesulfonylamino-3-methyl-5-vinylbenzyl)carbamic acid tert-butyl ester (85.9 mg, 0.09 mmol) was dissolved in CH$_2$Cl$_2$. 5~6 drops of CF$_3$COOH were added. The reaction mixture was stirred for 12 hr. The reaction mixture was concentrated to yield brownish syrup (100.4 mg).

$^1$H NMR (400 MHz, CD$_3$OD): δ 7.57 (d, 1H, J=1.6 Hz), 7.28 (d, 1H, J=1.6 Hz), 7.17 (dd, 1H, J=17.6, 10.8 Hz), 5.03 (d, 1H, J=17.6 Hz), 5.38 (d, 1H, J=10.8 Hz), 4.06 (s, 2H), 3.00 (s, 3H), 2.41 (s, 3H)

Step 7: N-{4-[3-(4-tert-Butyl-benzyl)ureidomethyl]-2-methyl-6-vinylphenyl}methanesulfonamide 4-tert-Butyl-benzylamine (1.5 eq, 71.91 μl, 0.44 mmol) was added in CH$_2$Cl$_2$ and then BOC$_2$O (1.5 eq, 0.44 mmol, 101.19 μl) and DMAP (0.2 eq, 0.06 mmol, 7.08 mg) were slowly added. After confirming the synthesis of the 1-tert-Butyl-4-isocyanatomethyl-benzene, N-(4-Aminomethyl-2-methyl-6-vinyl-phenyl)-methanesulfonamide (1 eq, 0.29 mmol, 70.5 mg) and TEA (2 eq, 0.58 mmol, 80.84 μl) were added into the reaction mixture. The reaction mixture was stirred for 12 hr. The reaction mixture was purified according to step 9 of example 7 to obtain N-{4-[3-(4-tert-Butyl-benzyl)ureidomethyl]-2-methyl-6-vinylphenyl}methanesulfonamide (29.75 mg, 23.9%).

mp: 105~107° C.;

IR (KBr pellet, cm$^{-1}$): 3359, 3280, 2963, 1636, 1316; $^1$H NMR (400 MHz, CDCl$_3$): δ 7.32 (s, 1H), 7.27 (d, 2H, J=8.0 Hz), 7.16 (d, 2H, J=8.0 Hz), 7.09 (s, 1H), 6.72 (dd, 1H, J=17.2, 10.8 Hz), 5.71 (d, 1H, J=17.6 Hz), 5.37 (d, 2H, J=10.8 Hz), 4.30 (d, 4H, J=10.0 Hz), 3.42 (s, 3H), 2.23 (s, 3H), 1.22 (s, 9H)

Example 9

N-{4-[3-(4-tert-Butyl-benzyl)-ureidomethyl]-2-chloro-6-vinyl-phenyl}-methanesulfonamide

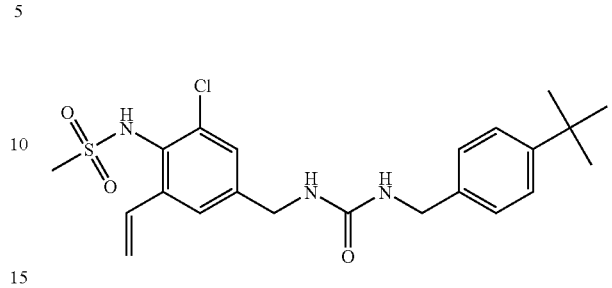

Step 1: 4-Amino-3-chloro-5-iodobenzonitrile

4-Amino-3-chloro-benzonitrile (100 mg, 0.66 mmol) and ICl (1.1 eq, 0.72 mmol, 117.05 mg) were added in methylene chloride. The reaction mixture was stirred for 12 hr. The reaction mixture was purified according to similar procedure to step 2 of Example 8 to obtain 4-Amino-3-chloro-5-iodo-benzonitrile (65.2 mg, 35.80%).

mp: 121~123° C.;

IR (KBr pellet, cm$^{-1}$): 3365, 2942, 2221, 1634, 728;

$^1$H NMR (400 MHz, CDCl$_3$): δ 7.42 (d, 1H, J=1.6 Hz), 7.43 (d, 1H, J=1.6 Hz), 5.01 (bs, 2H).

Step 2: (4-Amino-3-chloro-5-iodobenzyl)carbamic acid tert-butyl ester

4-Amino-3-chloro-5-iodobenzonitrile (65.2 mg, 0.23 mmol) was dissolved in THF at 0° C. After Borane-THF complex (4 eq, 0.94 mmol, 0.94 ml) was slowly added into the reaction mixture, A reaction temperature was heated to reflux. The reaction mixture was stirred for 12 hr with reflux. After confirming the completion of the reaction, MeOH was added. The mixture was stirred for 4 hr. The reaction solvent was removed in vacuo. A residue was extracted with Ethyl acetate, washed with H$_2$O and brine, dried with Na$_2$SO$_4$ and concentrated in vacuo to yield 4-Aminomethyl-2-iodo-6-methyl-phenylamine (19.4 mg).

4-Aminomethyl-2-chloro-6-iodophenylamine (52.92 mg, 0.19 mmol) was dissolved in THF, and then BOC$_2$O (1.1 eq, 0.21 mmol, 47.48 ml) was slowly added. The reaction mixture was stirred for 12 hr. A reaction mixture was extracted with Ethyl acetate, washed with H$_2$O and brine, dried with Na$_2$SO$_4$ and concentrated in vacuo. A residue was purified with column chromatography (n-Hx:EA=5:1) to obtain a solid (34.37 mg, 47.94%).

mp: 113~115° C.;

IR (KBr pellet, cm$^{-1}$): 3343, 1615, 717;

$^1$H NMR (400 MHz, CDCl$_3$): δ 7.39 (s, 1H), 7.09 (s, 1H), 4.76 (bs, 1H), 4.05 (bs, 2H), 4.05 (s, 2H), 1.38 (s, 9H)

Step 3: (4-Amino-3-chloro-5-vinylbenzyl)carbamic acid tert-butyl ester

Pd(PPh$_3$)$_4$ (0.06 eq, 0.01 mmol, 18.15 mg) and LiCl (2.8 eq, 0.73 mmol, 30.86 mg) were dissolved in DMF. 4-Amino-3-chloro-5-iodobenzyl)carbamic acid tert-butyl ester (100 mg, 0.26 mmol) and tributylvinyltin (1.5 eq, 0.39 mmol, 114.76 μl) were added. The reaction mixture was stirred for 12 hr in reflux. A reaction mixture was purified according to a similar procedure to step 3 to obtain solid (61.8 mg, 85.34%).

mp: 85~87° C.;

IR (KBr pellet, cm$^{-1}$): 3316, 2977, 1702, 1635, 725;

$^1$H NMR (400 MHz, CDCl$_3$): δ7.06 (d, 1H, J=2.0 Hz), 7.01 (d, 1H, J=2.0 Hz), 6.64 (dd, 1H, J=17.6, 11.2 Hz), 5.56 (dd, 1H, J=17.2, 1.2 Hz), 5.30 (dd, 1H, J=11.2, 1.2 Hz), 4.72 (bs, 1H), 4.11 (d, 2H, J=5.2 Hz), 1.38 (s, 9H).

Step 4: (3-Chloro-4-methanesulfonylamino-5-vinyl-benzyl)carbamic acid tert-butyl ester (4-Amino-3-chloro-5-vinylbenzyl)carbamic acid tert-butyl ester (40.2 mg, 0.14 mmol), methanesulfonyl chloride (5 eq, 0.71 mmol, 55.15 μl), and triethylamine (3 eq, 0.42 mmol, 58.34 μl) were added in methylene chloride. The reaction mixture was stirred for 5 hr. The reaction mixture was purified with similar procedure to step 5 of Example 8 to obtain a title compound (30.7 mg, 59.83%).

mp: 133~135° C.;

IR (KBr pellet, cm$^{-1}$): 3353, 2981, 1691, 1524, 1322, 740;

$^1$H NMR (400 MHz, CDCl$_3$): δ 7.40 (s, 1H), 7.25 (d, 1H, J=1.2 Hz), 7.19 (d, 1H, J=1.2 Hz), 7.14 (dd, 1H, J=17.6, 11.2 Hz), 6.18 (s, 1H), 5.70 (d, 1H, J=17.2 Hz), 5.34 (d, 1H, J=11.2 Hz), 4.88 (s, 1H), 4.24 (d, 2H, J=6.0 Hz), 3.00 (s, 3H), 1.40 (s, 9H).

Step 5: N-(4-Aminomethyl-2-chloro-6-vinylphenyl) methanesulfonamide (3-Chloro-4-methanesulfonylamino-5-vinylbenzyl)carbamic acid tert-butyl ester (30.7 mg, 0.09 mmol) and CF$_3$COOH (5-6 drops) was added into methylene chloride. The reaction mixture was stirred for 12 hr. The reaction mixture was concentrated in vacuo to give a title compound (33.4 mg, 100%).

$^1$H NMR (400 MHz, CD$_3$OD): δ7.75 (d, 1H, J=1.6 Hz), 7.55 (d, 1H, J=2.0 Hz), 7.22 (dd, 1H, J=17.6, 10.8 Hz), 5.88 (d, 1H, J=17.6 Hz), 5.43 (d, 1H, J=11.2 Hz), 4.13 (s, 2H), 3.10 (s, 3H)

Step 6: N-{4-[3-(4-tert-Butylbenzyl)ureidomethyl]-2-chloro-6-vinylphenyl}methanesulfonamide 4-tert-butylbenzylamine (1.5 eq, 71.10 μl, 0.44 mmol), BOC$_2$O (1.5 eq, 0.44 mmol, 101.19 μl), and DMAP (0.2 eq, 0.06 mmol, 7.08 mg) were added in methylene chloride. The reaction mixture was stirred for 5 hr. After confirming the synthesis of the 1-tert-butyl-4-isocyanatomethylbenzene with TLC, N-(4-Aminomethyl-2-chloro-6-vinylphenyl) methanesulfonamide (1 eq, 0.29 mmol, 108.6 mg) and TEA (2 eq, 0.58 mmol, 80.84 μl) were added into the reaction mixture. The reaction mixture was stirred for 12 hr and purified with similar procedure to step 7 of example 8 to gave a title compound (23.0 mg, 17.66%).

mp: 165~167° C.;

IR (KBr pellet, cm$^{-1}$): 3333, 2961, 1625, 1323, 1155, 765;

$^1$H NMR (400 MHz, CD$_3$OD): δ 7.52 (d, 1H, J=1.6 Hz), 7.33 (d, 1H, J=1.6 Hz), 7.31 (d, 2H, J=8.4 Hz), 7.18 (dd, 1H, J=17.6, 11.2 Hz), 7.17 (d, 2H, J=8.4 Hz), 5.75 (d, 1H, J=17.6 Hz), 5.32 (d, 1H, J=11.2 Hz), 4.30 (s, 2H), 4.27 (s, 2H), 3.05 (s, 3H), 1.26 (s, 9H).

Example 10

N-{4-[3-(4-tert-Butyl-benzyl)-ureidomethyl]-2-trifluoromethyl-6-vinyl-phenyl}-methanesulfonamide

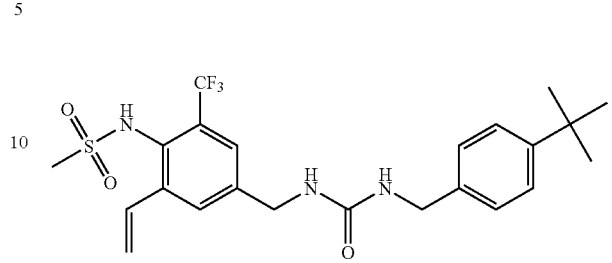

Step 1: 4-Iodo-2-trifluoromethylphenylamine

2-Trifluoromethylphenylamine (30 mg, 0.21 mmol) and ICl (1.1 eq, 0.24 mmol, 38.97 mg) were added into methylene chloride. The reaction mixture was stirred for 12 hr. The reaction mixture was purified according to step 2 of Example 8 to give a title compound (25.6 mg, 42.48%).

IR (NaCl neat, cm$^{-1}$): 3411, 3066, 1109, 701;

$^1$H NMR (400 MHz, CDCl$_3$): δ 7.61 (d, 1H, J=2.0 Hz), 7.46 (dd, 1H, J=8.4, 1.2 Hz), 6.45 (d, 1H, J=8.4 Hz), 4.05 (bs, 2H).

Step 2: 4-Amino-3-trifluoromethylbenzonitrile

4-Iodo-2-trifluoromethylphenylamine (50 mg, 0.17 mmol), Zn(CN)$_2$ (0.88 eq, 0.15 mmol, 18.00 mg), and Pd(PPh$_3$)$_4$ (0.1 eq, 0.02 mmol, 19.64 mg) were added in DMF. Zn(CN)$_2$ (0.88 eq, 0.15 mmol, 18.00 mg) and Pd(PPh$_3$)$_4$ (0.1 eq, 0.02 mmol, 19.64 mg) were added into the reaction mixture. The reaction mixture was stirred for 12 hr. The reaction mixture was purified according to step 1 of Example 8 to give a title product as a yellow solid (31.4 mg, 99.28%).

Mp: 54~56° C.; IR (KBr pellet, cm$^{-1}$): 3385, 3263, 2924, 2220, 1124, 701

$^1$H NMR (400 MHz, CDCl$_3$): δ 7.65 (d, 1H, J=2.0 Hz), 7.45 (dd, 1H, J=8.4, 2.0 Hz), 6.69 (d, 1H, J=8.4 Hz), 4.65 (s, 2H).

Step 3: 4-Amino-3-iodo-5-trifluoromethylbenzonitrile

4-Amino-3-trifluoromethylbenzonitrile (100 mg, 0.54 mmol) and ICl (1.1 eq, 0.58 mmol, 96.00 mg) were added methylene chloride. The mixture was stirred for 12 hr. The reaction mixture was purified according to step 2 of Example 8 to give a title compound (30.5 mg, 18.10%).

mp: 86~88° C.;

IR (KBr pellet, cm$^{-1}$): 3371, 3080, 2924, 2226, 1125, 701;

$^1$H NMR (400 MHz, CDCl$_3$): δ 8.02 (d, 1H, J=1.6 Hz), 7.35 (dd, 1H, J=133.2, 1.6 Hz), 7.65 (dd, 1H, J=10.0, 1.6 Hz), 5.20 (d, 2H, J=22.0 Hz).

Step 4: (4-Amino-3-iodo-5-trifluoromethylbenzyl)carbamic acid tert-butyl Ester 4-Amino-3-iodo-5-trifluoromethylbenzonitrile (1805.2 mg, 5.19 mmol) was dissolved in THF at 0° C. After Borane-THF complex (3 eq, 17.36 mmol, 17.36 ml) was slowly added into the reaction mixture, A reaction temperature was heated to reflux. The reaction mixture was stirred for 12 hr with reflux. After confirming the completion of the reaction, MeOH was added. The mixture was stirred for 4 hr. The reaction solvent was removed in vacuo. A residue was extracted with Ethyl acetate, washed with H₂O and brine, dried with Na₂SO₄ and concentrated in vacuo to yield 4-Aminomethyl-2-iodo-6-trifluoromethylphenylamine (55.1 mg).

4-Aminomethyl-2-iodo-6-trifluoromethyl-phenylamine (2025.7 mg, 6.45 mmol) was dissolved in THF, and then BOC₂O (0.8 eq, 5.16 mmol, 1187.15 μl) was slowly added. The reaction mixture was stirred for 12 hr. A reaction mixture was extracted with Ethyl acetate, washed with H₂O and brine, dried with Na₂SO₄, and concentrated in vacuo. A residue was purified with column chromatography (n-Hx:EA=5:1) to yield a solid (1501.1 mg, 55.94%).

mp: 120~122° C.;

IR (KBr pellet, cm⁻¹): 3387, 2984, 1687, 1107, 701;

¹H NMR (400 MHz, CDCl₃): δ 7.43 (d, 1H, J=160.4 Hz), 7.27 (d, 1H, J=37.2 Hz), 4.92 (s, 1H), 4.54 (s, 2H), 4.13 (s, 2H), 1.41 (s, 9H).

Step 5: (4-Amino-3-trifluoromethyl-5-vinylbenzyl)carbamic acid tert-butyl ester

Pd(PPh₃)₄ (0.06 eq, 0.014 mmol, 16.64 mg) and LiCl (2.8 eq, 0.67 mmol, 28.49 mg) were added into DMF. (4-Amino-3-iodo-5-trifluoromethylbenzyl)carbamic acid tert-butyl ester (100 mg, 0.24 mmol) and tributylvinyltin (1.5 eq, 0.36 mmol, 105.37 μl) were added into the reaction mixture. The reaction mixture was stirred for 12 ha in reflux. The reaction mixture was purified according to step 4 of Example 8 to give a title product, yellow syrup (51.5 mg, 67.87%).

mp: 90~92° C.;

IR (NaCl neat, cm⁻¹): 3357, 2981, 1702, 1635, 1116;

¹H NMR (400 MHz, CDCl₃): δ 7.24 (s, 1H), 7.22 (s, 1H), 6.64 (dd, 1H, J=17.2, 6.4 Hz), 5.57 (dd, 1H, J=17.2, 1.2 Hz), 5.36 (dd, 1H, J=10.8, 1.2 Hz), 4.71 (s, 1H), 4.15 (s, 2H), 4.14 (d, 2H J=5.2 Hz), 1.39 (s, 9H)

Step 6: (4-Methanesulfonylamino-3-trifluoromethyl-5-vinylbenzyl)carbamic acid tert-butyl ester (4-Amino-3-trifluoromethyl-5-vinylbenzyl)carbamic acid tert-butyl ester (235.6 mg, 0.75 mmol), Methanesulfonyl chloride (5 eq, 3.73 mmol, 288.40 μl), and triethylamine (3 eq, 2.25 mmol, 313.60 μl) were added to methylene chloride. The reaction mixture was stirred for 5 hr. The reaction mixture was purified according to step 5 of Example 8 to give a title product, yellow syrup (89.3 mg, 30.21%).

IR (KBr pellet, cm⁻¹): 3361, 2977, 1692, 1330, 1152;

¹H NMR (400 MHz, CDCl₃): 7.65 (s, 1H), 7.46 (s, 1H), 7.13 (dd, 1H, J=11.2, 17.6 Hz), 6.09 (s, 1H), 5.73 (d, 1H, J=17.6 Hz), 5.42 (d, 1H, J=11.2 Hz), 4.90 (s, 1H), 4.29 (d, 2H, J=5.6 Hz), 3.07 (s, 3H), 1.40 (s, 9H)

Step 7: N-(4-Aminomethyl-2-trifluoromethyl-6-vinylphenyl)methanesulfonamide (4-Methanesulfonylamino-3-trifluoromethyl-5-vinylbenzyl)carbamic acid tert-butyl ester (89.3 mg, 0.23 mmol) and CF₃COOH (5~6 drops) were added into methylene chloride. The mixture was stirred for 12 hr. The reaction mixture was purified according to step 6 of Example 8 to give a title product (101.4 mg, 100%).

¹H NMR (400 MHz, CD₃OD): 8.02 (s, 1H), 7.77 (s, 1H), 7.27 (dd, 1H, J=17.6, 11.2 Hz), 5.92 (d, 1H, J=17.6 Hz), 5.51 (d, 1H, J=11.2 Hz), 4.20 (s, 2H), 3.11 (s, 3H).

Step 8: N-{4-[3-(4-tert-Butylbenzyl)ureidomethyl]-2-trifluoromethyl-6-vinylphenyl}methanesulfonamide 4-tert-Butyl-benzylamine (1.5 eq, 15.20 μl, 0.09 mmol), BOC₂O (1.5 eq, 0.09 mmol, 20.70 μl), and DMAP (0.2 eq, 0.01 mmol, 1.34 mg) were added to methylene chloride. The reaction mixture was stirred for 5 hr. After confirming the synthesis of the 1-tert-butyl-4-isocyanatomethylbenzene with TLC, N-(4-Aminomethyl-2-trifluoromethyl-6-vinylphenyl)methanesulfonamide (1 eq, 0.06 mmol, 20.5 mg) and TEA (2 eq, 0.12 mmol, 16.72 μl) were added into the reaction mixture. The reaction mixture was stirred for 12 hr and purified with similar procedure to step 7 of example 8 to gave title compound (10.7 mg 36.88%).

mp: 134~136° C.;

IR (KBr pellet, cm⁻¹): 3361, 2962, 1642, 1261, 1151;

¹H NMR (400 MHz, CDCl₃): δ 7.64 (s, 1H), 7.44 (s, 1H), 7.28 (d, 2H, J=8.0 Hz), 7.16 (d, 2H, J=8.0 Hz), 7.11 (dd, 1H, J=17.2, 11.2 Hz), 6.03 (s, 1H), 5.71 (d, 1H, J=17.2 Hz), 5.41 (d, 1H, J=11.2 Hz), 4.37 (s, 2H), 4.29 (s, 2H), 3.06 (s, 3H), 1.23 (s, 9H).

Example 11

3-(4-t-butylphenyl)-N-[1-(R)-(4-methanesulfonylamino-3-vinylphenyl)ethyl]propiolicamide

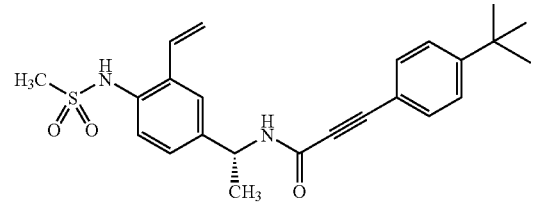

Step 1: (4-t-butyl-phenyl)-propynoic acid methyl ester

A 100 ml two-neck round bottom flask was filled with argon gas and the solution of 4-t-butyl-benzoyl chloride (500 mg, 2.34 mmol) in toluene was put into the flask. To the solution was added (triphenylphoshoranylidene)acetic acid methyl ester (1.5 eq, 3.52 mmol, 1178.39 mg) and refluxed at 90~100° C. for 12 hours. After confirming the completion of the reaction with TLC, toluene was removed under reduced pressure and column-chromatographed (n-hexane/ethyl acetate=4/1) to yield a yellow solid (product 1).

A 50 ml two-neck round bottom flask was filled with argon gas and the product(1) was put into the flask, heated, and stirred at 250° C. for 90 minutes. The reaction compound was extracted with methylenechloride and column-chromatographed (n-hexane/ethyl acetate=25/1) to yield yellow liquid (product(2), 81.7 mg, 19.69%).

IR (KBr pellet, cm⁻¹): 2963, 2224, 1715, 1506, 1460;

¹H NMR (400 MHz, CDCl₃): product(1) 7.70~7.65 (m, 6H), 7.59 (d, 2H, J=8.4 Hz), 7.47~7.35 (m, 9H), 7.29 (d, 2H, J=8.8 Hz); product(2) 7.50 (d, 2H, J=8.0 Hz), 7.36 (d, 2H, J=8.0 Hz), 3.80 (s, 3H), 1.28 (s, 9H).

Step 2: (4-t-Butylphenyl)-propynoic acid (4-t-butyl-phenyl)-propionic acid methyl ester (21.7 mg, 0.11 mmol) was put into 25 ml round-bottom flask and dissolved in a little amount of methanol. To the solution was added $K_2CO_3$ solution slowly and stirred for 1 hour. After confirming the completion of the reaction with TLC, methanol was removed under reduced pressure and the residue was extracted with ethylacetate. The ethylacetate layer was washed with water and brine, dried over $Na_2SO_4$, filtered and concentrated under reduced. The obtained liquid was column-chromatographed (methanol: ethylacetate=1:1) to yield white liquid (20.8 mg, 95.37%).

IR (KBr pellet, $cm^{-1}$): 3419, 2963, 2214, 1576, 1460;
$^1$H NMR (400 MHz, $CDCl_3$): 7.44 (d, 2H, J=8.8 Hz), 7.40 (d, 2H, J=8.4 Hz), 1.30 (s, 9H).

Step 3: 3-(4-t-butylphenyl)-N-[1-(R)-(4-methanesulfonylamino-3-vinyl phenyl)ethyl]propiolicamide A dried 25 ml two-neck round bottom flask was filled with argon gas and the solution of N—(R)-[4-(1-amino-ethyl)-2-vinyl-phenyl]-methanesulfonamide (110.55 mg, 0.46 mmol) and (4-t-butyl-phenyl)-propionic acid (1.2 eq, 0.56 mmol, 110.4 mg) in DMF was put into the flask. To the solution were added triethylamine (2 eq, 0.92 mmol, 128.23 mg) and diethylcyano phosphonate (1.2 eq, 0.56 mmol, 83.76 μl) and stirred for 12 hours. After confirming the completion of the reaction with TLC, DMF was removed under reduced pressure and the residue was extracted with ethylacetate. The ethylacetate layer was washed with water and brine, dried over $Na_2SO_4$, filtered and concentrated under reduced. The obtained liquid was column-chromatographed (n-hexane/ethyl acetate=2/1) to yield a yellow solid (54 mg, 28.62%).

mp: 89~91° C.;
$[\alpha]^{20}_D$: –30.72° C. ($CHCl_3$, c 1.51);
IR (KBr pellet, $cm^{-1}$): 3259, 3023, 2965, 2212, 1628, 1323;
$^1$H NMR (400 MHz, $CDCl_3$): 7.45 (d, 1H, J=2.0 Hz), 7.44 (d, 2H, J=8.4 Hz), 7.39 (d, 1H, J=8.4 Hz), 7.32 (d, 2H, J=8.8 Hz), 7.24 (dd, 1H, J=8.0, 2.4 Hz), 6.91 (dd, 1H, J=17.2, 11.2 Hz), 6.76 (s, 1H), 6.35 (d, 1H, J=8.0 Hz), 5.70 (dd, 1H, J=17.6, 0.8 Hz), 5.42 (dd, 1H, J=10.8, 0.8 Hz), 5.15 (quin, 1H, J=6.8 Hz), 2.93 (s, 3H), 1.50 (d, 3H, J=6.8 Hz), 1.26 (s, 9H)

Example 12

3-(4-tert-Butylphenyl)propynoic acid 3-fluoro-4-methanesulfonylamino-5-vinylbenzylamide

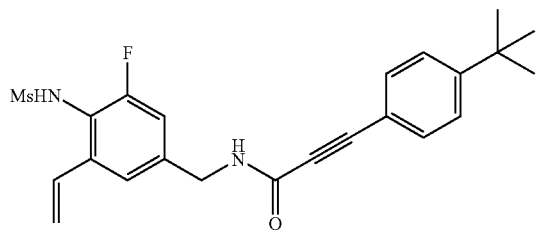

A mixture of (4-tert-Butylphenyl)propynoic acid (step 2 of Example 11, 0.16 mmol, 33.0 mg) and N-(4-aminomethyl-2-fluoro-6-vinylphenyl)methanesulfonamide (step 6 of Example 2, 0.19 mmol, 39.20 mg), DEPC (1.2 eq, 0.19 mmol, 29.13 μl), TEA (2 eq, 0.32 mmol, 44.60 μl) in DMF under an Ar atmosphere was stirred at room temperature for 12 h. Upon completion, as determined by TLC, the reaction solution was extracted by EtOAc (150 ml×3) and the organic phase was washed with $H_2O$, dried ($Na_2SO_4$), filtered and concentrated. After silica gel column chromatography (n-hexane/EtOAc=2:1), 3-(4-tert-butylphenyl)propynoic acid 3-fluoro-4-methanesulfonylamino-5-vinylbenzylamide (49.5 mg, 0.11 mmol, 72.25%) was isolated.

mp: 155~157° C.;
IR (KBr pellet, $cm^{-1}$): 3238, 3026, 2964, 2223, 1634, 1321, 1154;
$^1$H NMR (400 MHz, $CDCl_3$): δ 7.51 (d, 1H, J=8.8 Hz), 7.45 (d, 2H, J=8.4 Hz), 7.35 (s, 1H), 7.14 (dd, 1H, J=17.6, 11.2 Hz), 7.07 (dd, 1H, J=10.0, 1.6 Hz), 6.28 (t, 1H, J=5.6 Hz), 6.03 (s, 1H), 5.80 (d, 1H, J=17.6 Hz), 5.45 (d, 1H, J=11.2 Hz), 4.51 (d, 2H, J=6.0 Hz), 3.06 (s, 3H), 1.28 (s, 9H)

Example 13

3-(4-tert-Butylphenyl)propynoic acid N-[1-(3-fluoro-4-methanesulfonylamino-5-vinylphenyl)ethyl]amide

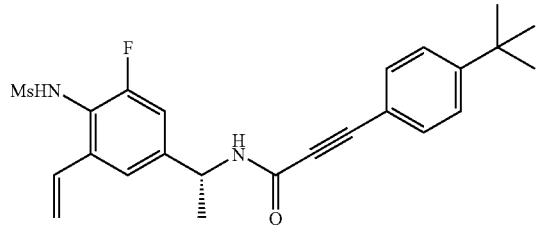

N-[4-(1-Amino-ethyl)-2-fluoro-6-vinylphenyl]methanesulfonamide (0.03 mmol, 10.0 mg), (4-tert-butylphenyl)propynoic acid (step 2 of Example 11, 0.03 mmol, 6.52 mg), DEPC (0.03 mmol, 5.46 μl), and TEA (0.06 mmol, 8.36 μl) were added into DMF. The mixture was stirred for 12 hr. The reaction mixture was purified according to Example 12 to give a title product (11.3 mg, 95.09%).

mp: 108~110° C.;
$[\alpha]_D^{20}$: –14.54 ($CHCl_3$, c 0.81);
IR (KBr pellet, $cm^{-1}$): 3248, 3025, 2965, 2211, 1629, 1323, 1152; $^1$H NMR (400 MHz, $CDCl_3$): δ 7.44 (d, 2H, J=8.4 Hz), 7.38 (s, 1H), 7.34 (d, 2H, J=8.4 Hz), 7.14 (dd, 1H, J=17.6, 10.8 Hz), 7.06 (dd, 1H, J=10.4, 2.0 Hz), 6.17 (d, 1H, J=7.6 Hz), 5.80 (d, 1H, J=17.6 Hz), 5.43 (d, 1H, J=10.8 Hz), 5.15 (quin, 1H, J=7.2 Hz), 3.05 (s, 3H), 1.52 (d, 3H, J=6.8 Hz), 1.28 (s, 9H)

Example 14

3-(4-t-butylphenyl)-N-[1-(R)-(4-methanesulfonylamino-3-vinyl phenyl) ethyl]acrylamide

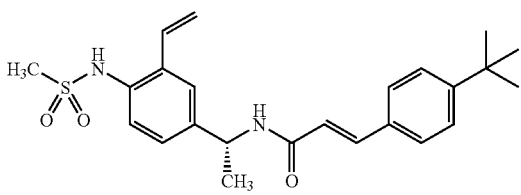

A 25 ml two-neck round bottom flask was filled with argon gas and the solution of 3-(4-t-butyl-phenyl)-acrylic acid (21.1 mg, 0.103 mmol, 1 eq.) and diethylcyanophosphate (17.2 µl, 0.113 mmol, 1.1 eq.) in DMF was put into the flask. To the solution were added the solution of 1-(R)-(4-methanesulfonylamino-3-vinyl-phenyl)-ethyl-ammonium, trifluoro-acetate (36.7 mg, 0.103 mmol, 1 eq.) and triethylamine (43.1 µl, 0.309 mmol, 3 eq.) in DMF. The mixture solution was stirred for one night. After confirming the completion of the reaction with TLC, DMF was removed under reduced pressure and the residue was extracted with ethylacetate. The ethylacetate layer was washed with water and brine, dried over $Na_2SO_4$ and ethylacetate was removed under reduced pressure. The obtained liquid was column-chromatographed (n-hexane/ethyl acetate=1/1) to yield a pale yellow solid (33.4 mg, 76.0%).

mp: 111.2-112.5° C.;
$[\alpha]^{23}_D$: −19.70° C. (c 1.12, $CHCl_3$);
IR (KBr pellet, $cm^{-1}$): 3428, 3377, 3274, 3087, 2964, 2868, 1655, 1618;
$^1$H NMR (400 MHz, $CDCl_3$): 7.55 (d, 1H, J=115.6 Hz), 7.39 (d, 1H, J=1.6 Hz), 7.35 (d, 2H, J=8.0 Hz), 7.29 (d, 3H, J=8.0 Hz), 6.84 (dd, 1H, J=17.2, 10.8 Hz), 6.68 (bs, 1H), 6.33 (d, 1H, J=15.6 Hz), 6.07 (d, 1H, J=8.0 Hz), 5.63 (dd, 1H, J=17.2, 0.8 Hz), 5.34 (dd, 1H, J=10.8, 0.8 Hz), 5.15 (quin, 1H, J=6.8 Hz), 2.90 (s, 3H), 1.45 (d, 3H, J=6.8 Hz), 1.24 (s, 9H)

Example 15

3-(4-t-butylphenyl)-N-(3-fluoro-4-methanesulfonylamino-5-vinylbenzyl)acrylamide

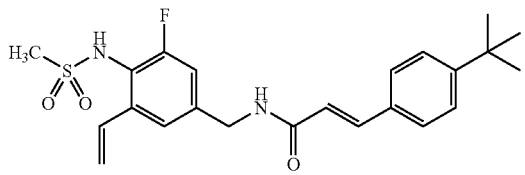

A 25 ml two-neck round bottom flask was filled with argon gas and the solution of 3-(4-t-butylphenyl)-acrylic acid (46.4 mg, 0.227 mmol, 1 eq.) and diethylcyanophosphate (37.9 µl, 0.250 mmol, 1.1 eq.) in DMF was put into the flask. To the solution were added the solution of 3-fluoro-4-methanesulfonylamino-5-vinylbenzyl-ammonium synthesized in step 5 of Example 2, trifluoroacetate (81.4 mg, 0.227 mmol, 1 eq.) and triethylamine (94.9 µl, 0.681 mmol, 3 eq.) in DMF. The solution was stirred for one night. After confirming the completion of the reaction with TLC, DMF was removed under reduced pressure and the residue was extracted with ethylacetate. The ethylacetate layer was washed with water and brine, dried over $Na_2SO_4$, and ethylacetate was removed under reduced pressure. The obtained liquid was column-chromatographed (n-hexane/ethyl acetate=1/1) to yield a white solid (80.9 mg, 82.8%).

mp: 182-183° C.
IR (KBr pellet, $cm^{-1}$): 3418, 3238, 3073, 2962, 1654, 1622, 1321, 1153;
$^1$H NMR (400 MHz, $CD_3OD$): 7.53 (d, 1H, J=16.0 Hz), 7.47 (d, 2H, J=8.4 Hz), 7.45 (d, 1H, J=2.0 Hz), 7.40 (d, 2H, J=8.4 Hz), 7.15 (dd, 1H, J=17.6, 10.8 Hz), 7.08 (dd, 1H, J=10.4, 2.0 Hz), 6.58 (d, 1H, J=16.0 Hz), 5.81 (d, 1H, J=17.6 Hz), 5.35 (d, 1H, J=10.8 Hz), 4.47 (s, 2H), 2.98 (s, 3H), 1.29 (s, 9H)

Example 16

3-(4-t-butylphenyl)-N-(3-fluoro-5-ethynyl-4-methanesulfonyl amino-benzyl)acrylamide

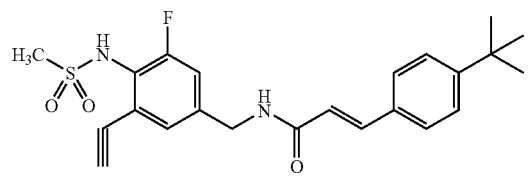

A 25 ml two-neck round bottom flask was filled with argon gas and the solution of 3-(4-t-butylphenyl)-acrylic acid (66.6 mg, 0.326 mmol, 1 eq.) and diethylcyanophosphate (54.4 µl, 0.359 mmol, 1.1 eq.) in DMF was put into the flask. To the solution was added the solution of 3-fluoro-5-ethynyl-4-methanesulfonylaminobenzyl-ammonium obtained in step 3 of Example 3, trifluoroacetate (116.3 mg, 0.326 mmol, 1 eq.) and triethylamine (136.3 µl 0.978 mmol, 3 eq.) in DMF. The solution was stirred for one night. After confirming the completion of the reaction with TLC, DMF was removed under reduced pressure and the residue was extracted with ethylacetate. The ethylacetate layer was washed with water and brine, dried over $Na_2SO_4$ and ethylacetate was removed under reduced pressure. The obtained liquid was column-chromatographed(n-hexane/ethyl acetate 1/1) to yield a white solid (109.6 mg, 77.9%).

mp: 149-150° C.;
IR (KBr pellet, $cm^{-1}$): 3413, 3254, 3069, 2963, 2107, 1621, 1325, 1154;
$^1$H NMR (400 MHz, $CD_3OD$): 7.54 (d, 1H, J=16.0 Hz), 7.48 (d, 2H, J=8.4 Hz), 7.41 (d, 2H, J=8.4 Hz), 7.30 (d, 1H, J=2.0 Hz), 7.19 (dd, 1H, J=10.4, 2.0 Hz), 6.58 (d, 1H, J=16.0 Hz), 4.44 (s, 2H), 3.86 (s, 1H), 3.09 (s, 3H), 1.30 (s, 9H)

Example 17

3-(4-t-butylphenyl)-N-(4-methanesulfonylamino-3-vinylbenzyl)acryl amide

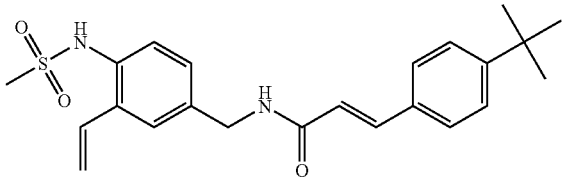

A dried 25 ml two-neck round bottom flask was filled with argon gas and the solution of N-(4-aminomethyl-2-vinylphenyl)-methanesulfonamide (51 mg, 0.23 mmol) and 3-(4-t-butyl-phenyl)-acrylic acid (1.2 eq, 0.27 mmol, 55.26 mg) in DMF was put into the flask. To the solution were added triethylamine (2 eq, 0.46 mmol, 64.12 mg) and diethylcyanophosphonate (1.2 eq, 0.27 mmol, 41.88 µl) and stirred for 12 hours. After confirming the completion of the reaction with TLC, the reaction solution was extracted with methylenechloride, washed with water and brine, dried over $Na_2SO_4$, filtered and concentrated under reduced pressure. The obtained liquid was column-chromatographed (n-hexane/ethyl acetate=1/1) to yield a white solid (48.4 mg, 43.37%).

$^1$H NMR (400 MHz, CDCl$_3$): 7.59 (d, 1H, J=15.6 Hz), 7.37 (d, 2H, J=8.0 Hz), 7.34 (s, 1H), 7.31 (d, 1H, J=10.4 Hz), 7.18 (d, 2H, J=8.0 Hz), 6.82 (dd, 1H, J=17.6, 11.2 Hz), 6.44 (s, 1H), 6.33 (d, 1H, J=7.6 Hz), 6.01 (bs, 1H), 5.65 (d, 1H, J=17.6 Hz), 5.39 (d, 1H, J=11.2 Hz), 4.47 (d, 2H, J=5.6 Hz), 2.91 (s, 3H), 1.24 (s, 9H).

Example 18

3-(4-trifluoromethylphenyl)-N-(4-methanesulfonylamino-3-vinylbenzyl)acrylamide

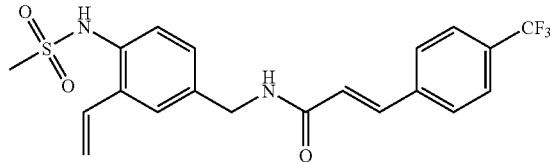

The acryl amide (90 mg) was synthesized according to the same procedure as described similar procedure in Example 17.

$^1$H NMR (300 MHz, CDCl$_3$): 7.71 (d, 1H, J=15.9 Hz), 7.62 (m, 4H), 7.47 (m, 2H), 6.88 (dd, 1H, J=17.4, 11.1 Hz), 6.53 (d, 1H, J=15.6 Hz), 6.27 (bs, 1H), 5.93 (bs, 1H), 5.74 (d, 1H, J=17.4 Hz), 5.51 (d, 1H, J=11.1 Hz), 4.59 (d, 2H, J=6 Hz), 3.01 (s, 3H)

Example 19

3-(4-methylthiophenyl)-N-(4-methanesulfonylamino-3-vinylbenzyl)acrylamide

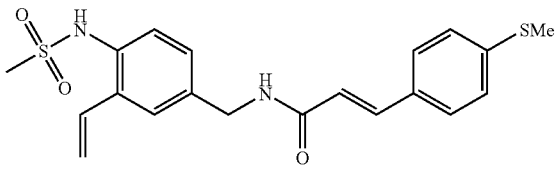

The acrylamide (120 mg) was synthesized according to the same procedure as described in Example 11.

$^1$H NMR (300 MHz, CDCl$_3$): 7.64 (d, 1H, J=15.6 Hz), 7.43 (m, 2H), 7.25 (m, 4H), 6.87 (dd, 1H, J=17.1, 6.6 Hz), 6.36 (d, 1H, J=15.3 Hz), 6.26 (bs, 1H), 5.86 (bs, 1H), 5.74 (d, 1H, J=17.1 Hz), 5.50 (d, 1H, J=11.1 Hz), 4.58 (d, 2H, J=6 Hz), 3.00 (s, 3H), 2.50 (s, 3H)

Example 20

3-(4-tert-Butyl-phenyl)-N-(4-methanesulfonylamino-3-methyl-5-vinylbenzyl)acrylamide

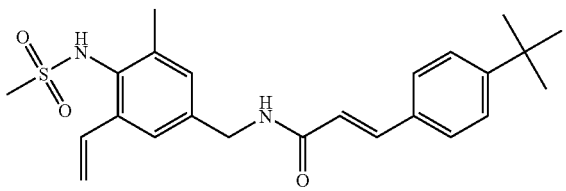

N-(4-Aminomethyl-2-methyl-6-vinylphenyl)methanesulfonamide (1 eq, 33.5 mg, 0.14 mmol), 3-(4-tert-butylphenyl)acrylic acid (1.2 eq, 0.17 mmol, 34.18 mg), DEPC (1.2 eq, 0.17 mmol, 25.49 µl), and TEA (2 eq, 0.28 mmol, 39.03 µl) were added in DMF. The mixture was stirred for 12 hr. The reaction mixture was purified according to Example 17 to give a white solid (29.83 mg, 51.3%).

mp: 182~184° C.; IR (KBr pellet, cm$^{-1}$): 3287, 3069, 2963, 1655, 1315

$^1$H NMR (400 MHz, CD$_3$OD): δ 7.52 (d, 1H, J=15.6 Hz), 7.46 (d, 2H, J=8.4 Hz), 7.43 (s, 1H), 7.40 (d, 2H, J=8.4 Hz), 7.16 (s, 1H), 7.15 (dd, 1H, J=17.6, 11.2 Hz), 6.58 (d, 1H, J=15.6 Hz), 5.75 (d, 1H, J=17.6 Hz), 5.32 (d, 1H, J=11.2 Hz), 4.43 (s, 2H), 2.97 (s, 3H), 2.38 (s, 3H), 1.29 (s, 9H)

Example 21

3-(4-tert-Butylphenyl)-N-(3-chloro-4-methanesulfonylamino-5-vinylbenzyl)acrylamide

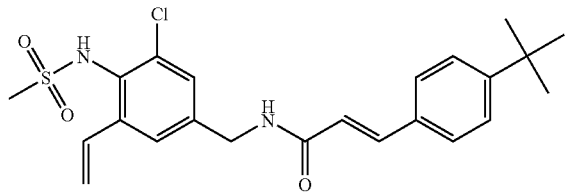

N-(4-Aminomethyl-2-chloro-6-vinylphenyl)methanesulfonamide (step 5 of Ex 9, 1 eq, 33.4 mg, 0.09 mmol), 3-(4-tert-butylphenyl)acrylic acid (1.2 eq, 0.11 mmol, 21.87 mg), DEPC (1.2 eq, 0.11 mmol, 16.63 µl), and TEA (2 eq, 0.18 mmol, 25.09 µl) were added in DMF. The mixture was stirred for 12 hr. The reaction mixture was purified according to Example 17 to give a white solid (20.8 mg, 51.80%).

mp: 157~159° C.;

IR (KBr pellet, cm$^{-1}$): 3248, 3064, 2962, 1653, 1321, 701;

$^1$H NMR (400 MHz, CD$_3$OD): δ 7.58 (d, 1H, J=1.6 Hz), 7.53 (d, 1H, J=16.0 Hz), 7.47 (d, 2H, J=8.4 Hz), 7.40 (d, 2H, J=8.4 Hz), 7.38 (d, 1H, J=1.6 Hz), 7.19 (dd, 1H, J=17.6, 11.2 Hz), 6.59 (d, 1H, J=16.0 Hz), 5.79 (d, 1H, J=17.6 Hz), 5.34 (d, 1H, J=11.2 Hz), 4.46 (s, 2H), 3.05 (s, 3H), 1.29 (s, 9H).

Example 22

3-(4-tert-Butyl-2-morpholin-4-yl-phenyl)-N-(3-fluoro-4-methanesulfonylamino-5-vinylbenzyl)acrylamide

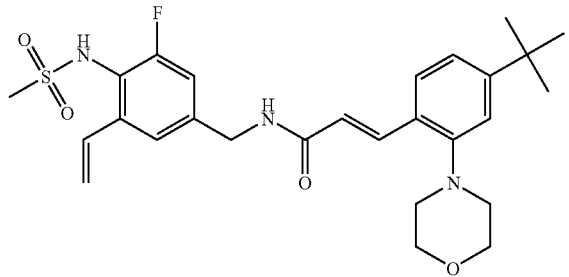

Step 1:
3-(4-tert-Butyl-2-morpholin-4-yl-phenyl)acrylic acid ethyl ester

Palladium(II) acetate (1.4 mg, 0.006 mmole, 6 mol % eq), rac-2,2'-bis(diphenylphosphino)-1,1'-binaphthyl (7.5 mg, 0.012 mmole, 12 mol % eq), and cesium carbonate (50.3 mg, 0.155 mmole, 1.5 eq) were added into anhydrous toluene.

3-(4-tert-Butyl-2-trifluoromethanesulfonyloxyphenyl) acrylic acid ethyl ester (36.2 mg, 0.103 mmol, 1 eq) in toluene solvent was added by cannula. Morpholine (13.5 µl, 0.155 mmol, 1.5 eq) was added. The mixture was stirred for 12 hr in reflux. After confirming the completion of the reaction with TLC, the reaction mixture was filtered with celite. The filterate was concentrated in vacuo, and then the residue was purified with column chromatography(n-Hx:EA=12:1) to give title product (16.7 mg, 51.2%).

$^1$H NMR (400 MHz, CDCl$_3$): δ 7.98 (d, J=16.0 Hz, 1H), 7.41 (d, J=8.0 Hz, 1H), 7.05 (dd, J=8.0, 1.6 Hz, 1H), 6.99 (d, J=1.6 Hz, 1H), 6.32 (d, J=16.0 Hz, 1H), 4.19 (q, J=7.2 Hz, 2H), 3.82 (t, J=4.8 Hz, 4H), 2.90 (t, J=4.8 Hz, 4H), 1.29-1.25 (m 12H)

Step 2: 3-(4-tert-Butyl-2-morpholin-4-yl-phenyl)-N-(3-fluoro-4-methanesulfonylamino-5-vinylbenzyl) acrylamide 3-(4-tert-Butyl-2-morpholin-4-yl-phenyl)acrylic acid ethyl ester (29.1 mg, 0.092 mmol, 1 eq) was added into methanol and H$_2$O. Sodium hydroxide (36.7 mg, 0.917 mmole, 10 eq) was added. The mixture was stirred for 12 hr. After confirming the completion of the reaction, The reaction mixture was cooled down to 0° C. The reaction mixture was acidified with 5% HCl. The reaction solvent was removed under reduced pressure to give a yellow solid (26.6 mg, 100%). TLC: R$_f$=0.15 (n-Hexane EtOAc=2:1/KMnO$_4$)

3-(4-tert-Butyl-2-morpholin-4-yl-phenyl)acrylic acid 25.9 mg (0.092 mmol, 1 eq.) and diethylcyanophosphine (16.8 µl, 0.110 mmol, 1.2 eq) were added in DMF under argon atmosphere. N-(4-Aminomethyl-2-fluoro-6-vinylphenyl)methanesulfonamide (49.3 mg, 0.138 mmol, 1.2 eq.) and Triethylamine (38.5 µl, 0.276 mmol, 3 eq) were added into the reaction mixture. After confirming the completion of the reaction, reaction solvent was eliminated in vacuo. The residue was extracted with EtOAc, washed with brine, dried with Na$_2$SO$_4$ and then concentrated in vacuo. The residue was purified with column chromatography (n-Hexane:EtOAc=1:1) to give whitish solid (28.2 mg, 62.4%).

mp (° C.): 171-173° C.; IR (KBr pellet, cm$^{-1}$): 3422, 2959, 2857, 1649, 1617, 1322, 1154;

$^1$H NMR (400 MHz, CDCl$_3$): 8.01 (d, J=15.6 Hz, 1H), 7.53 (d, J=8.8 Hz, 1H), 7.50 (s, 1H), 7.19 (dd, J=11.2, 17.6 Hz, 1H), 7.15-7.11 (m, 3H), 6.61 (d, J=15.6 Hz, 1H), 5.84 (d, J=17.6 Hz, 1H), 5.38 (d, J=11.2 Hz, 1H), 4.51 (s, 2H), 3.88 (t, J=4.4 Hz, 4H), 3.02 (s, 2H), 2.94 (t, J=4.4 Hz, 4H), 1.32 (s, 9H)

Example 23

3-[4-tert-Butyl-2-(2-methoxy-ethoxy)-phenyl]-N-(3-fluoro-4-methanesulfonylamino-5-vinyl-benzyl)-acrylamide

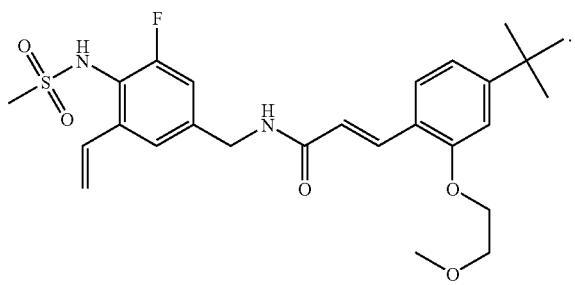

Step 1: 4-tert-Butyl-1-iodo-2-(2-methoxyethoxy)benzene

NaH (21.0 mg, 0.5250 mmol, 60% disp. oil, 5 eq) and tert-Butyl-2-iodo-phenol (29.0 mg, 0.105 mmol, 1 eq) were added DMF. Chloroethyl methyl ether (23.96 µl, 0.26 mmol, 2.5 eq) was added into the mixture. The reaction mixture was stirred overnight at 90° C. The reaction mixture was quenched by adding H$_2$O. After DMF was removed in vacuo, the residue was extracted with EtOAc. A combined organic layer was washed by H$_2$O and brine, dried with Na$_2$SO$_4$, and then concentrated in vacuo. The residue was purified with column chromatography (n-Hexane:EtOAc=20:1) to give liquid (32.0 mg, 91.2%).

$^1$H NMR (400 MHz, CDCl$_3$): δ 7.58 (d, J=8.4 Hz, 1H), 6.82 (d, J=2.0 Hz, 1H), 6.69 (dd, J=8.4, 2.4 Hz, 1H), 4.10 (t, J=4.8 Hz, 2H), 3.75 (dd, J=4.8, 4.4 Hz, 2H), 3.43 (s, 3H), 1.22 (s, 9H); IR (NaCl Neat, cm$^{-1}$): 2960, 2871, 1713, 1628, 1607, 1165.

Step 2: 3-[4-tert-Butyl-2-(2-methoxyethoxy)phenyl]acrylic acid methyl ester

Palladium acetate (63.77 mg, 0.2841 mmol, 6% mol eq), and 1.1'-Bis(diphenylphosphino)ferrocene (314.99 mg, 0.5682 mmol, 12% mol eq) were add in DMF solution. Methyl acrylate (469.01 µl, 5.2082 mmol, 1.1 eq), triethylamine (1.3171 ml, 9.4694 mmol, 2 eq), and 4-tert-Butyl-1-iodo-2-(2-methoxy-ethoxy)-benzene (1.5823 g, 4.7347 mmol, 1 eq) were added. The reaction mixture was stirred for overnight at 60° C. The reaction mixture was purified according to step 1 to give reddish liquid (1.1156 g, 83.5%).

$^1$H NMR (400 MHz, CDCl$_3$): δ 7.96 (d, J=16.0 Hz, 1H), 7.43 (d, J=8.4 Hz, 1H), 6.99 (dd, J=8.0, 1.6 Hz, 1H), 6.96 (d, J=1.6 Hz, 1H), 6.52 (d, J=16.4 Hz, 1H), 4.23 (q, J=7.2 Hz, 2H), 4.19 (t, J=4.8 Hz, 2H), 3.81 (t, J=4.8 Hz, 2H), 3.47 (s, 3H), 1.33-1.30 (m, 12H); IR (NaCl Neat, cm$^{-1}$): 3408, 2964, 2869, 1683, 1624

Step 3: 3-(4-tert-Butyl-2-morpholine-4-yl-phenyl)-N-(3-fluoro-4-methanesulfonylamino-5-vinylbenzyl) acrylamide 3-[4-tert-Butyl-2-(2-methoxyethoxy)phenyl]acrylic acid ethyl ester (40.4 mg, 0.132 mmol, 1 eq) and sodium hydroxide (52.8 mg, 1.32 mmole, 10 eq) were added in methanol and H$_2$O. The reaction mixture was purified according to step 2 of Example 22 to give 3-[4-tert-Butyl-2-(2-methoxyethoxy)phenyl]acrylic acid (36.5 mg, 77.3%). 3-[4-tert-Butyl-2-(2-methoxyethoxy)-phenyl]acrylic acid (26.4 mg, 0.095 mmol, 1 eq.), Diethylcyanophosphine (17.3 µl, 0.114 mmol, 1.2 eq), N-(4-Aminomethyl-2-fluoro-6-vinylphenyl)methanesulfonamide (40.8 mg, 0.1114 mol, 1.2 eq.), and Triethylamine (39.7 µl, 0.285 mmol, 3 eq) were added in DMF. The mixture was stirred for overnight at room temperature. The reaction mixture was purified according to Example 17 to give a whitish solid (28.4 mg, 59.2%).

IR (KBr pellet, cm$^{-1}$): 3422, 2959, 2857, 1649, 1617, 1322, 1154;

$^1$H NMR (400 MHz, CDCl$_3$): 7.79 (d, J=16.0 Hz, 1H), 7.48 (s, 1H), 7.38 (d, J=8.0 Hz, 1H), 7.08 (dd, J=11.2, 17.6 Hz, 1H), 7.01 (dd, J=10.4, 1.6 Hz, 1H), 6.95-6.89 (m, 2H), 6.60 (d, J=16.0 Hz, 1H), 5.74 (d, J=17.6 Hz, 1H), 5.28 (d, J=11.2 Hz, 1H), 4.39 (s, 2H), 4.10 (t, J=4.4 Hz, 2H), 3.71 (t, J=4.4 Hz, 2H), 3.64-3.60 (m, 2H), 3.34 (s, 2H), 2.91 (s, 3H), 1.22 (s, 9H)

Example 24

3-(4-tert-Butylphenyl)-N-(4-methanesulfonylamino-3-trifluoromethyl-5-vinylbenzyl)acrylamide

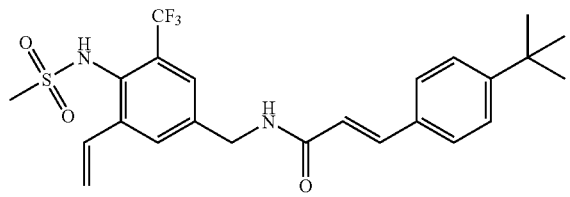

N-(4-Aminomethyl-2-trifluoromethyl-6-vinylphenyl)methanesulfonamide (step 7 in Example 10, 1 eq, 44.1 mg, 0.13 mmol), 3-(4-tert-Butyl-phenyl)-acrylic acid (1.1 eq, 0.15 mmol, 29.99 mg), DEPC (1.2 eq, 0.16 mmol, 23.67 μl) and TEA (2 eq, 0.26 mmol, 36.24 μl) were added in DMF. The reaction mixture was stirred for 12 hr. The reaction mixture was purified according to Example 17 to give a white solid (55.4 mg, 88.75%).

mp: 174~176° C.; IR (KBr pellet, cm$^{-1}$): 3257, 3078, 2964, 1653, 1326;

$^1$H NMR (400 MHz, CDCl$_3$): δ 7.67 (d, 1H, J=1.6 Hz), 7.60 (d, 1H, J=15.6 Hz), 7.47 (d, 1H, J=1.6 Hz), 7.38 (d, 2H, J=8.4 Hz), 7.32 (d, 2H, J=8.4 Hz), 7.13 (dd, 1H, J=17.6, 10.8 Hz), 6.65 (s, 1H), 6.62 (t, 1H, J=6.0 Hz), 6.39 (d, 1H, J=16.0 Hz), 5.71 (d, 1H, J=17.6 Hz), 5.39 (d, 1H, J=11.2 Hz), 4.49 (d, 2H, J=5.6 Hz), 3.07 (s, 3H), 1.26 (s, 9H).

Example 25

3-[4-tert-Butyl-2-(4-methylpiperazin-1-yl)phenyl]-N-(3-fluoro-4-methanesulfonylamino-5-vinylbenzyl)acrylamide

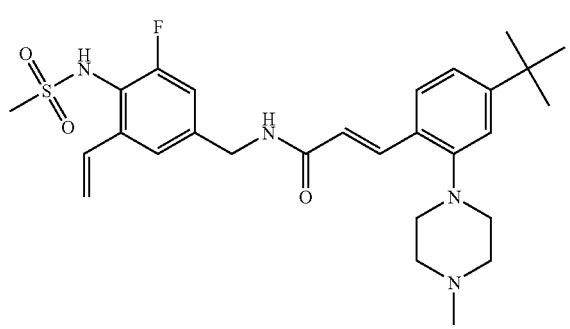

Step 1: 3-[4-tert-Butyl-2-(4-methylpiperazine-1-yl)phenyl]acrylic acid ethyl ester Palladium acetate (2.8 mg, 0.013 mmol, 6% mol eq), rac-2,2'-bis(diphenylphosphino)1,1'-binaphthyl (16.2 mg, 0.026 mmol, 12% mol eq), and cesium carbonate (102.6 mg, 0.315 mmol, 1.5 eq) were added in anhydrous toluene under argon atmosphere. After stirring for 5 min, 3-(4-tert-butyl-2-trifluoromethanesulfonyloxyphenyl)acrylic acid ethyl ester (74.0 mg, 0.210 mmol, 1 eq) and N-Methylpiperazine (34.9 μl, 0.315 mmole, 1.5 eq) were added. The mixture was stirred for 24 hr at 80° C. The reaction mixture was purified according to step 1 of Example 22 to give yellow liquid (50.8 mg, 73.2%).

Step 2: 3-[4-tert-Butyl-2-(4-methylpiperazin-1-yl)phenyl]-N-(3-fluoro-4-methanesulfonylamino-5-vinylbenzyl)acrylamide 3-[4-tert-Butyl-2-(4-methylpiperazin-1-yl)phenyl]acrylic acid ethyl ester (29.1 mg, 0.092 mmol, 1 eq) and sodium hydroxide (36.7 mg, 0.917 mmole were added in methanol and H$_2$O. The mixture was stirred for 12 hrs. The reaction mixture acidified with 5% HCl. The reaction mixture was concentrated in vacuo to give a yellow solid (27.8 mg, 100%).

3-[4-tert-Butyl-2-(4-methylpiperazin-1-yl)phenyl]acrylic acid (46.6 mg, 0.154 mmol, 1 eq.) and diethylcyanophosphine (28.0 μl, 0.185 mmol, 1.2 eq) were added in DMF. N-(4-Aminomethyl-2-fluoro-6-vinylphenyl)methanesulfonamide (60.7 mg, 0.169 mmol, 1.1 eq.) and triethylamine (64.4 μl, 0.462 mmol, 3 eq) were added. The reaction mixture was stirred overnight at room temperature. A reaction solvent was removed in vacuo. A residue was extracted with EtOAc. A combined organic layer was washed with brine, dried over Na$_2$SO$_4$, and then concentrated in vacuo. A residue was purified with column chromatography (MeOH:EtOAc=1:1) to give a solid (63.9 mg, 71.3%).

IR (KBr pellet, cm$^{-1}$): 3422, 2959, 2857, 1649, 1617, 1322, 1154;

$^1$H NMR (400 MHz, CDCl$_3$): 7.96 (d, J=15.6 Hz, 1H), 7.54 (d, J=8.8 Hz, 1H), 7.49 (s, 1H), 7.26-7.09 (m, 4H), 6.62 (d, J=15.6 Hz, 1H), 5.84 (d, J=17.6 Hz, 1H), 5.39 (d, J=10.8 Hz, 1H), 4.51 (s, 2H), 3.03 (s, 4H), 2.87 (s, 4H), 2.51 (s, 4H), 1.32 (s, 9H)

Example 26

3-[4-tert-Butyl-2-(2-piperidine-1-yl-ethoxy)phenyl]-N-(3-fluoro-4-methanesulfonylamino-5-vinylbenzyl)acrylamide

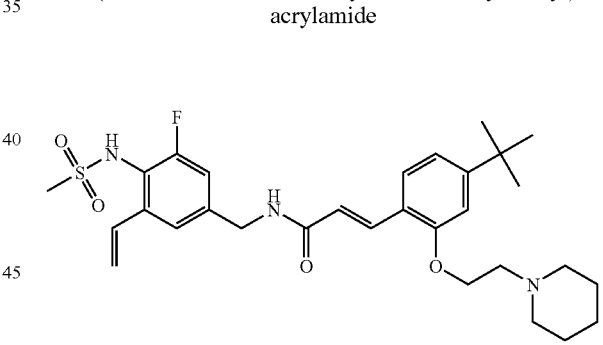

Step 1: 3-[4-tert-Butyl-2-(2-piperidine-1-yl-ethoxy)phenyl]acrylic acid ethyl ester 3-(4-tert-Butyl-2-hydroxyphenyl)acrylic acid ethyl ester (59.0 mg, 0.238 mmol) and NaH (47.5 mg, 60% disp. oil, 5 eq) were added in anhydrous DMF. The reaction mixture was cooled down to 0° C. 1-(2-Chloroethyl)piperidine hydrochloride (87.6 mg 0.476 mmol, 2 eq) was added. The mixture was heated to 90° C. The reaction was stirred for 12 hr at 90° C. The reaction was quenched by adding H$_2$O. The reaction mixture extracted with EtOAc and then washed with H$_2$O and brine. The residue was purified with column chromatography (EtOAc) to give a yellow liquid (14.0 mg, 16.4%).

$^1$H NMR (400 MHz, CDCl$_3$): δ 7.86 (d, J=16.0 Hz, 1H), 7.39 (d, J=8.8 Hz, 1H), 6.95-6.93 (m, 2H), 4.15-4.09 (m, 4H), 2.77 (t, J=5.6 Hz, 2H), 2.52 (s, 4H), 1.54 (quin, J=5.6 Hz, 4H), 1.42-1.36 (m, 2H), 1.23 (s, 9H)

Step 2: 3-[4-tert-Butyl-2-(2-piperidine-1-yl-ethoxy) phenyl]-N-(3-fluoro-4-methanesulfonylamino-5-vinylbenzyl)acrylamide 3-[4-tert-Butyl-2-(2-piperidin-1-yl-ethoxy)phenyl]acrylic acid ethyl ester (14.0 mg, 0.039 mmol, 1 eq) and sodium hydroxide (7.8 mg, 0.195 mmole, 5 eq) were added in methanol and H$_2$O. The reaction mixture was stirred for 12 hrs at room temperature. The reaction mixture was acidified with 5% HCl solution. The reaction mixture was concentrated in vacuo to give a yellow solid (12.9 mg, 100%).

3-[4-tert-Butyl-2-(2-piperidin-1-yl-ethoxy)phenylacrylic acid (0.039 mmol, 1 eq.), diethylcyanophosphine 7.1 μl (0.0.047 mmol, 1.2 eq), N-(4-aminomethyl-2-fluoro-6-vinylphenyl)-methanesulfonamide 16.8 mg (0.047 mmol, 1.2 eq.), and triethylamine 16.3 μl (0.117 mmol, 3 eq) were added in DMF. The mixture was stirred overnight at room temperature. The reaction mixture was purified according to Example 25 to give solid (32.6 mg, 100%).

$^1$H NMR (400 MHz, CDCl$_3$): 7.83 (d, J=16.0 Hz, 1H), 7.44 (d, J=8.0 Hz, 1H), 7.38 (s, 1H), 7.09 (dd, J=11.2, 18.0 Hz, 1H), 7.03-6.99 (m, 2H), 6.96 (s, 1H), 6.55 (d, J=16.0 Hz, 1H), 5.73 (d, J=17.6 Hz, 1H), 4.04 (s, 2H), 4.25 (t, J=10.2 Hz, 2H), 3.17 (t, J=10.2 Hz, 2H), 2.97-2.92 (m, 9H), 1.66 (quin, J=5.6 Hz, 4H), 1.48-1.47 (m, 2H), 1.23 (s, 9H)

Example 27

3-[4-tert-Butyl-2-(2-methoxyethylamino)phenyl]-N-(3-fluoro-4-methanesulfonylamino-5-vinylbenzyl) acrylamide

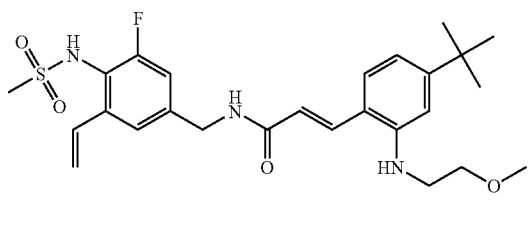

Step 1: 3-[4-tert-Butyl-2-(2-methoxyethylamino) phenyl]acrylic acid methyl ester Tris(dibenzylideneacetone)-dipalladium (19.1 mg, 0.021 mmol), 1,1'-bis(diphenylphosphino)-ferrocene (34.7 mg, 0.063 mmol), 2-methoxyethylamine (72.5 μl, 0.834 mmol), and 3-(4-tert-butyl-2-trifluoromethanesulfonyloxyphenyl)-acrylic acid methyl ester (152.6 mg, 0.417 mmol, 1 eq) were added to anhydrous toluene. Cesium carbonate (203.8 mg, 0.623 mmol) was added into the mixture. The reaction mixture was stirred for 12 hrs at 80° C. The reaction mixture was purified according to step 1 of Example 27 to give a greenish liquid (64.3 mg, 52.9%).

$^1$H NMR (400 MHz, CDCl$_3$): δ 7.75 (d, J=16.0 Hz, 1H), 7.25 (d, J=8.0 Hz, 1H), 6.71 (dd, J=8.0, 1.6 Hz, 1H), 6.63 (d, J=1.6 Hz, 1H), 6.24 (d, J=16.0 Hz, 1H), 3.72 (s, 3H), 3.57 (t, J=5.2 Hz, 2H), 3.33 (s, 3H), 3.29 (t, J=5.2 Hz, 2H), 1.23 (s, 9H); IR (NaCl Neat, cm$^{-1}$): 3441, 2960, 2871, 1713, 1628, 1607, 1165.

Step 2: 3-[4-tert-Butyl-2-(2-methoxyethylamino) phenyl]-N-(3-fluoro-4-methanesulfonylamino-5-vinylbenzyl)acrylamide 3-[4-tert-Butyl-2-(2-methoxyethylamino)phenyl]acrylic acid methyl ester (64.3 mg, 0.221 mmol, 1 eq) and sodium hydroxide (44.1 mg, 1.103 mmole, 5 eq) were added in methanol and H$_2$O. The reaction mixture was stirred for 12 hrs at room temperature. The reaction mixture was acidified with 5% HCl solution. The reaction mixture was concentrated in vacuo to give a yellow solid (50.2 mg, 100%).

3-[4-tert-Butyl-2-(2-methoxyethylamino)phenyl]acrylic acid (0.221 mmol), and diethylcyanophosphine (40.2 μl, 0.265 mmol, 1.2 eq) were added in DMF. N-(4-Aminomethyl-2-fluoro-6-vinylphenyl)methanesulfonamide (95.5 mg, 0.265 mmol) and triethylamine (92.4 μl, 0.663 mmol) was added. The reaction mixture was stirred overnight at room temperature. A reaction mixture was purified according to step 2 of Example 24 to give greenish solid (77.8 mg, 71.3%).

mp (° C.): 196-198; IR (KBr pellet, cm$^{-1}$): 3434, 3254, 2961, 1648, 1608, 1321, 1153, 974; $^1$H NMR (400 MHz, CDCl$_3$): 7.76 (d, J=15.2 Hz, 1H), 7.27 (s, 1H), 7.23 (d, J=8.4 Hz, 1H), 7.07 (dd, J=17.6, 10.8 Hz, 1H), 6.97 (d, J=8.0 Hz, 1H), 6.69 (d, J=8.0 Hz, 1H), 6.34 (s, 1H), 6.23 (t, 8.0 Hz, 1H), 5.71 (d, J=17.6 Hz, 1H), 5.45 (d, J=10.4 Hz, 1H), 4.46 (d, J=6.0 Hz, 2H), 3.57 (t, J=5.2 Hz, 2H), 3.32-3.28 (m, 5H), 2.99 (s, 3H), 2.51 (s, 3H), 1.23 (s, 9H)

Example 28

3-(4-tert-Butyl-2-methoxyphenyl)-N-(3-fluoro-4-methanesulfonylamino-5-vinyl-benzyl)acrylamide

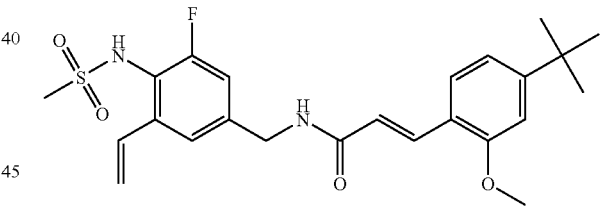

Step 1: 3-(4-tert-Butyl-2-methoxyphenyl)acrylic acid methyl Ester

Potassium carbonate (59.0 mg, 0.427 mmol) and iodoethane (25.6 μl, 0.320 mmol) were added in acetone. 3-(4-tert-Butyl-2-hydroxyphenyl)acrylic acid methyl ester (50.0 mg, 0.213 mmol) was added into reaction mixture. The reaction mixture was stirred for 5 hrs with reflux. A reaction solvent was removed in vacuo. The residue was extracted with EtOAc. A combined organic layer was washed with brine, dried over Na$_2$SO$_4$, concentrated under reduced pressure. The residue was purified with column chromatography(n-Hexane:EtOAc=10:1) to obtain a solid (56.4 mg, 67.2%).

IR (KBr pellet, cm$^{-1}$): 2952, 1686, 1625, 1439;

$^1$H NMR (400 MHz, CDCl$_3$): δ 7.99 (d, J=16.8 Hz, 1H), 7.44 (d, J=8.0 Hz, 1H), 6.96 (dd, J=8.0, 19.2 Hz, 2H), 4.13 (dd, J=6.8, 13.6 Hz, 2H), 3.80 (s, 3H), 1.33 (bs, 9H).

Step 2: 3-(4-tert-Butyl-2-methoxyphenyl)-N-(3-fluoro-4-methanesulfonylamino-5-vinyl-benzyl) acrylamide 3-(4-tert-butyl-2-methoxyphenyl)acrylic acid methyl ester (125 mg, 1 eq), and NaOH (75 mg, 1.88 mmol) were added into H$_2$O. The reaction mixture was stirred for 12 hrs. The reaction mixture was acidified with 5% HCl solution. The reaction mixture was concentrated in vacuo to give a solid (121 mg, 100%).

3-(4-tert-butyl-2-methoxyphenyl)acrylic acid (121 mg, 0.519 mmol, 1 eq), N-(4-aminomethyl-2-fluoro-6-vinyl-phenyl)-methanesulfonamide (148.8 mg, 0.415 mmol), DEPC (94.5 μl, 0.62 mmol, 1.2 eq) and TEA (217 μl, 1.56 mmol) were added in DMF. The reaction mixture was stirred for 5 hrs. A reaction solvent was removed in vacuo. A residue was extracted with EtOAc. A combined organic layer was washed with brine, dried over Na$_2$SO$_4$, concentrated in vacuo. The residue was purified with column chromatography(n-Hexane:EtOAc=1:1) to obtain a solid (96.2 mg, 50.3%).

mp.: 150-152° C.; IR (KBr pellet, cm$^{-1}$): 3435, 1651, 1616, 1448, 1321;
$^1$H NMR (400 MHz, CDCl$_3$): δ 7.77 (d, J=15.6 Hz, 1H), 7.37 (d, J=9.2 Hz, 1H), 7.12 (dd, J=11.2, 18.0 Hz, 1H), 7.01 (dd, J=10.4, 1.6 Hz, 1H), 6.95-6.89 (m, 2H), 6.62 (d, J=15.6 Hz, 1H), 5.74 (dd, J=17.6, 0.8 Hz, 1H), 5.28 (d, J=11.6 Hz, 1H), 4.39 (s, 2H), 3.79 (s, 3H), 2.92 (d, J=0.8 Hz, 3H), 1.23 (s, 3H).

Example 29

3-(4-tert-Butyl-2-hydroxyphenyl)-N-(3-fluoro-4-methanesulfonylamino-5-vinylbenzyl)acrylamide

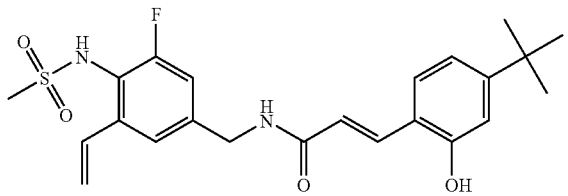

Step 1: 5-tert-Butyl-2 iodophenol 3-tert-Butylphenol (30 mg, 0.199 mmol, 1 eq) and N-iodosuccinimide (44.9 mg, 0.199 mmol) were added in anhydrous acetonitrile under argon atmosphere. The mixture was stirred for 1 hr. The reaction solvent was removed in vacuo. The residue was extracted with CH$_2$Cl$_2$. A combined organic layer was washed with H$_2$O and brine, dried over Na$_2$SO$_4$, and concentrated in vacuo. A residue was purified with column chromatography (n-Hexane:EtOAc=30:1) to obtain yellow syrup (46.9 mg, 85.1%).

$^1$H NMR (400 MHz, CDCl$_3$): δ 7.46 (d, J=8.0 Hz, 1H), 6.95 (s, 1H), 6.64 (dd, J=8.0, 2.4 Hz, 1H), 5.20 (bs, 1H), 1.20 (s, 9H); IR (NaCl Neat, cm$^{-1}$): 3489, 2963, 1561, 1399, 1304, 1190

Step 2: (4-tert-Butyl-2-hydroxyphenyl)acrylic acid methyl Ester

Palladium acetate (16.8 mg, 0.075 mmol), 1.1'-bis(diphenylphosphino)ferrocene (49.9 mg, 0.090 mmol), triethylamine (418.1 μl, 3.000 mmol), and methyl acrylate (148.6 μl, 1.650 mmol) were added to anhydrous toluene. 5-tert-Butyl-2-iodophenol (414.4 mg, 1.500 mmol) was added. The reaction mixture was stirred overnight at 60° C. A reaction solvent was removed in vacuo. The residue was purified according to previous similar workup method to obtain a solid (322.3 mg, 91.7%).

$^1$H NMR (400 MHz, CDCl$_3$): δ 7.93 (d, J=16.0 Hz, 1H), 7.31 (d, J=8.0 Hz, 1H), 6.87 (dd, J=8.0, 2.0 Hz, 1H), 6.80 (d, J=1.6 Hz, 1H), 6.53 (dd, J=16.0, 2.0 Hz, 1H), 3.75 (s, 3H), 1.21 (s, 9H); IR (KBr pellet, cm$^{-1}$): 3362, 2952, 1686, 1625, 1439, 1325

Step 3: 3-(4-tert-Butyl-2-hydroxyphenyl)-N-(3-fluoro-4-methanesulfonylamino-5-vinylbenzyl)acrylamide 3-(4-tert-Butyl-2-hydroxy-phenyl)-N-(3-fluoro-4-methanesulfonylamino-5-vinylbenzyl)acrylic acid (25.9 mg, 0.092 mmol), diethylcyanophosphine (19.85 μl, 0.131 mmol), N-(4-Aminomethyl-2-fluoro-6-vinylphenyl)-methanesulfonamide (46.8 mg, 0.131 mmol), and triethylamine (45.58 μl, 0.327 mmol) were added in DMF under argon atmosphere. The reaction mixture was purified according to step 2 to obtain a solid (30.1 mg, 51%).

mp (° C.): 171-173; IR (KBr pellet, cm$^{-1}$): 3422, 2959, 2857, 1649, 1617, 1322, 1154;
$^1$H NMR (400 MHz, CDCl$_3$): 7.74 (d, J=16 Hz, 1H), 7.38 (S, 1H), 7.29 (d, 1H, J=804 Hz), 7.08 (dd, 1H, J=15.6, 11.2 Hz), 7.01 (d, 1H, J=10.4 Hz), 6.81 (d, 2H, J=11.2 Hz), 6.65 (d, J=16 Hz, 1H), 5.75 (d, J=17.6 Hz, 1H), 5.28 (d, J=10.8 Hz, 1H), 4.39 (s, 2H), 2.92 (s, 3H), 1.19 (s, 9H)

Example 30

3-(2-Allyloxy-4-tert-butylphenyl)-N-(3-fluoro-4-methanesulfonylamino-5-vinylbenzyl)acrylamide

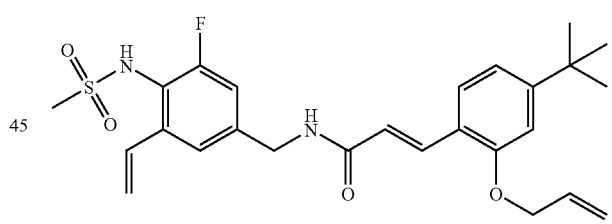

Step 1: 3-(2-Allyloxy-4-tert-butylphenyl)acrylic acid methyl Ester 3-(4-tert-Butyl-2-hydroxy-phenyl)-acrylic acid methyl ester (50 mg, 0.21 mmol), allyl-iodide (29.26 μl, 0.32 mmol), and K$_2$CO$_3$ (58.05 mg, 0.42 mmol) were added in acetone. The reaction mixture was stirred overnight. The purification with column chromatography (n-Hexane:EtOAc=10:1) was carried out to give a solid (51.4 mg, 89.3%).

mp.: 170.5~171.2° C.; IR (KBr pellet, cm$^{-1}$): 3227, 3076, 1685, 1651, 1617, 1153;
$^1$H NMR (400 MHz, CDCl$_3$): δ 7.93 (d, J=16.0 Hz, 1H), 7.36 (d, J=8.0 Hz, 1H), 6.91 (d, J=8.0 Hz, 1H), 6.84 (s, 1H), 6.43 (d, J=16.0 Hz, 1H), 5.98 (m, 1H), 5.36 (d, J=17.2 Hz, 1H), 5.23 (d, J=10.4 Hz, 1H), 4.56 (s, 2H), 3.70 (s, 3H), 1.23 (s, 9H)

Step 2: 3-(2-Allyloxy-4-tert-butylphenyl)-N-(3-fluoro-4-methanesulfonylamino-5-vinylbenzyl)acrylamide 3-(2-Allyloxy-4-tert-butyl-phenyl)acrylic acid methyl ester (51.4 mg, 0.18 mmol, 1 eq) and NaOH (37.5 mg, 0.94 mmol, 5 eq) were added in H$_2$O. The reaction mixture was stirred for 12 hrs. A reaction mixture was acidified with 5% HCl solution. A reaction mixture was concentrated in vacuo to give a solid (46.8 mg, 100%).

3-(2-Allyloxy-4-tert-butyl-phenyl)-acrylic acid (46.8 mg, 0.18 mmol), N-(4-aminomethyl-2-fluoro-6-vinyl-phenyl)-methanesulfonamide (78.83 mg, 0.22 mmol), DEPC (33.38 μl, 0.22 mmol, 1.2 eq), and TEA (75.27 μl, 0.54 mmol) were added in DMF. The reaction mixture was stirred for 5 hrs. A reaction mixture was purified according to step 2 of Example 27 to give a solid (78.7 mg, 89.9%).

mp.: 176.3~178.2° C.; IR (KBr pellet, cm$^{-1}$): 3440, 3076, 1652, 1617, 1321;

$^1$H NMR (400 MHz, CDCl$_3$): δ 7.85 (d, J=15.6 Hz, 1H), 7.34 (d, J=8.0 Hz, 1H), 7.28 (s, 1H), 7.08 (dd, J=17.6, 11.2 Hz, 1H), 7.01 (d, J=1.2 Hz, 1H), 6.98 (s, J=1.2 Hz, 1H), 6.90 (dd, J=8.0, 1.6 Hz, 1H), 6.49 (d, J=16 Hz, 1H), 5.72 (d, J=17.6 Hz, 1H), 5.40 (m, 1H), 5.34 (d, J=6 Hz, 1H), 5.26 (m, 1H), 5.23 (s, 1H), 4.56 (d, J=1.2 Hz, 2H), 4.80 (d, J=5.6 Hz, 2H), 2.99 (s, 3H), 1.24 (m, 9H)

Example 31

4-(5-tert-Butyl-2-[2-(3-fluoro-4-methanesulfonylamino-5-vinylbenzylcarbamoyl)vinyl]phenoxy)-piperidine-1-carboxylic acid tert-butyl ester

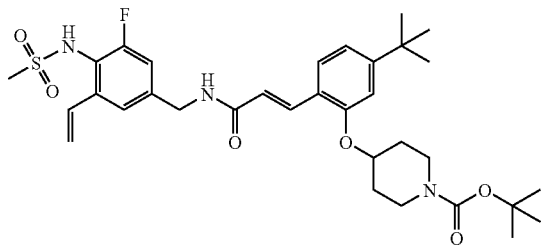

Step 1: 4-[5-tert-Butyl-2-(2-methoxycarbonylvinyl)phenoxy]piperidine-1-carboxylic acid tert-butyl ester 3-(4-tert-Butyl-2-hydroxyphenyl)acrylic acid methyl ester (24.7 mg, 0.105 mmole), 4-methanesulfonyloxypiperidine-1-carboxylic acid tert-butyl ester (58.7 mg, 0.210 mmol), potassium carbonate (43.7 mg, 0.316 mmol) was added in DMF. The reaction mixture was stirred overnight. The reaction mixture was purified according to step 1 of Example 30 to give solid (45.6 mg, 100%).

$^1$H NMR (400 MHz, CDCl$_3$): δ 7.90 (d, J=16.4 Hz, 1H), 7.39 (d, J=8.0 Hz, 1H), 6.93 (d, J=8.0 Hz, 1H), 6.85 (s, 1H), 6.41 (dd, J=8.0, 2.8 Hz, 1H), 4.50 (quin, J=3.2 Hz, 1H), 3.72 (s, 3H), 3.61 (m, 2H), 3.35 (m, 2H), 1.87 (m, 2H), 1.76 (m, 2H), 1.41 (s, 9H), 1.24 (s, 9H).

Step 2: 4-(5-tert-Butyl-2-[2-(3-fluoro-4-methanesulfonylamino-5-vinylbenzylcarbamoyl)vinyl]phenoxy)-piperidine-1-carboxylic acid tert-butyl ester 4-[5-tert-Butyl-2-(2-methoxycarbonylvinyl)phenoxy]piperidine-1-carboxylic acid tert-butyl ester (56.3 mg, 0.135 mol, 1 eq) and NaOH (26.9 mg, 0.674 mmol) was added in H$_2$O. The reaction mixture was stirred for 12 hr. The reaction mixture was acidified with 5% HCl solution. The reaction mixture was concentrated in vacuo to give solid (54.5 mg, 100%).

3-[4-tert-Butyl-2-(2-methoxyethoxy)-phenyl]acrylic acid (0.135 mmol), diethylcyanophosphine (24.6 μl, 0.162 mmol, 1.2 eq), N-(4-aminomethyl-2-fluoro-6-vinylphenyl)methanesulfonamide (58.0 mg, 0.162 mmol), and triethylamine (56.4%, 0.405 mmol, 3 eq) was added in DMF under argon atmosphere. The reaction mixture was stirred overnight. The reaction mixture was purified according to step 2 of Example 27 to give solid (52.6 mg, 100%).

mp (° C.): 122-124° C.; IR (KBr pellet, cm$^{-1}$): 3423, 3086, 2964, 1655, 1607, 1420, 1329, 1275, 1156;

$^1$H NMR (400 MHz, CDCl$_3$): δ 7.87 (d, J=16.0 Hz, 1H), 7.35 (d, J=8.0 Hz, 1H), 7.20 (s, 1H), 7.04 (dd, J=17.6, 10.8 Hz, 1H), 6.94 (d, J=10.0 Hz, 1H), 6.88-6.80 (m, 3H), 6.45 (d, J=15.6 Hz, 1H), 5.66 (d, J=17.6 Hz, 1H), 5.29 (d, J=11.6 Hz, 1H), 4.42 (d, J=6.0 Hz, 1H), 4.06-3.98 (m. 1H), 3.61-3.57 (m. 2H), 3.30-3.24 (m. 2H), 2.94 (s, 3H), 1.86-1.82 (m. 2H), 1.76-1.70 (m. 2H), 1.37 (s, 9H), 1.22 (s, 9H)

Example 32

3-[4-tert-butyl-2-(3-methylbutylamino)phenyl]-N-(3-fluoro-4-methanesulfonylamino-5-vinylbenzyl)acrylamide

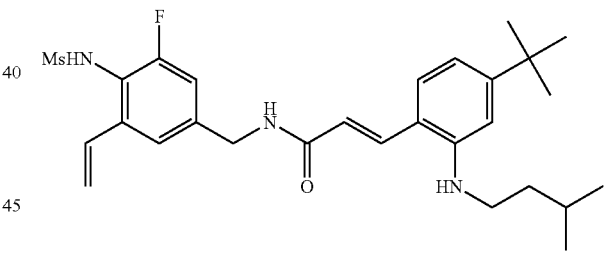

Step 1: 3-(4-tert-Butyl-2-butylaminophenyl)acrylic acid methyl Ester

Tris(dibenzylidene acetone)dipalladium (5%, 0.04 mmol, 37.49 mmol), 1,1'-bis(diphenylphosphino) ferrocene (15%, 0.12 mmol, 68.19 mg), isoamylamine (1.64 mmol, 190.87 μl), and 3-(4-tert-butyl-2-trifluoromethanesulfonyloxyphenyl)acrylic acid methyl ester (0.82 mmol, 300 mg) were added to toluene. Cesium carbonate (1.23 mmol, 400.76 mg) was added. The reaction mixture was stirred for 12 hrs at 80° C. The reaction mixture was purified according to step 1 of Example 27 to give yellow syrup (100.5 mg, 40.42%).

IR (NaCl neat, cm$^{-1}$): 3353, 3235, 3028, 2977, 1685, 1156;

$^1$H NMR (400 MHz, CDCl$_3$): δ 7.80 (d, 1H, J=15.6 Hz), 7.33 (s, 1H), 7.30 (d, 1H, J=8.0 Hz), 6.78 (d, 1H, J=8.0 Hz), 6.77 (s, 1H), 6.28 (d, 1H, J=15.6 Hz), 3.77 (s, 3H), 3.17 (t, 2H, J=7.6 Hz), 1.64~1.53 (m, 1H), 1.28 (s, 9H), 1.94 (d, 6H, J=6.8 Hz).

Step 2: 3-[4-tert-butyl-2-(3-methylbutylamino)phe-nyl]-N-(3-fluoro-4-methanesulfonylamino-5-vinyl-benzyl)acrylamide 3-(4-tert-Butyl-2-butylaminophenyl)acrylic acid methyl ester (0.20 mmol, 61.1 mg) and NaOH (5 eq, 1.00 mmol, 40.30 mg) were added in methanol and water. The reaction mixture was stirred for 12 hrs. The reaction mixture was acidified with 5% HCl solution. The reaction residue was concentrated in vacuo to give a solid (39.34 mg, 100%).

3-[4-tert-butyl-2-(3-methylbutylamino)phenyl]acrylic acid (0.13 mmol, 39.34 mg), N-(4-aminomethyl-2-fluoro-6-vinylphenyl)methanesulfonamide (0.15 mmol, 51.99 mg), DEPC (1.2 eq, 0.16 mmol, 23.67 µl), and TEA (2 eq, 0.26 mmol, 36.24 µl) were added in DMF. The reaction mixture was stirred overnight. The reaction mixture was purified according to step 2 of Example 27 to give a yellow solid (45.3 mg, 61.54%).

mp: 164~166° C.;

IR (KBr pellet, cm$^{-1}$): 3279, 3239, 3073, 2957, 1649, 1611, 1321, 1153; $^1$H NMR (400 MHz, CDCl$_3$): δ 7.76 (d, 1H, J=15.2 Hz), 7.24 (s, 1H), 7.21 (d, 1H, J=8.0 Hz), 7.05 (dd, 1H, J=17.6, 11.2 Hz), 6.94 (d, 1H, J=10.0 Hz), 6.65 (d, 1H, J=8.0 Hz), 6.62 (s, 1H), 6.38 (s, 1H), 6.21 (d, 1H, J=14.8 Hz), 6.12 (s, 1H), 5.69 (d, 1H, J=17.6 Hz), 5.34 (d, 1H, J=11.2 Hz), 4.44 (d, 2H, J=6.4 Hz), 3.13 (t, 2H, J=7.2 Hz), 2.98 (s, 3H), 1.65 (dq, 1H, J=13.2, 6.4 Hz), 1.48 (td, 2H, J=7.2 Hz), 1.23 (s, 9H), 0.88 (d, 6H, J=6.4 Hz), Example 33

3-(4-tert-Butyl-2-isobutylaminophenyl)-N-(3-fluoro-4-methanesulfonylamino-5-vinylbenzyl)acrylamide

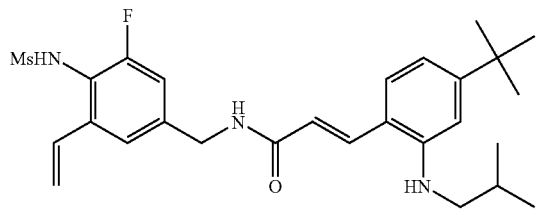

Step 1:
3-(4-tert-Butyl-2-isobutylaminophenyl)acrylic acid methyl ester

Tris(dibenzylideneacetone)-dipalladium (5%, 0.04 mmol, 37.24 mmol), 1,1'-bis(diphenylphosphino)-ferrocene (15%, 0.12 mmol, 67.36 mg), isobutylamine (1.62 mmol, 160.98 µl), and 3-(4-tert-butyl-2-trifluoromethanesulfonyloxy-phenyl)acrylic acid methyl ester (0.81 mmol, 298 mg) were added in toluene. Cesium carbonate (1.22 mmol, 395.87 mg) was added. The reaction mixture was stirred for 12 hrs at 80° C. A reaction mixture was purified according to step 1 of Example 27 to give yellow syrup (22.8 mg, 10%).

IR (NaCl neat, cm$^{-1}$): 3440, 2961, 1651, 1597;

$^1$H NMR (400 MHz, CDCl$_3$): δ 7.80 (d, 1H, J=15.6 Hz), 7.30 (d, 1H, J=8.0 Hz), 6.76 (d, 1H, J=8.0 Hz), 6.75 (s, 1H), 6.28 (d, 1H, J=15.6 Hz), 3.77 (s, 3H), 2.98 (d, 2H, J=6.8 Hz), 1.99~1.89 (m, 1H), 1.28 (s, 9H), 1.00 (d, 6H, J=6.8 Hz).

Step 2:
3-(4-tert-Butyl-2-isobutylaminophenyl)acrylic acid 3-(4-tert-butyl-2-isobutylaminophenyl)acrylic acid methyl ester (0.08 mmol, 22.8 mg) and NaOH (0.39 mmol, 15.76 mg) were added in methanol and water. The reaction mixture was stirred for 12 hrs. The reaction mixture was acidified with 5% HCl solution. The reaction mixture was concentrated in vacuo to give a solid (22.02 mg, 100%).

$^1$H NMR (400 MHz, CD$_3$OD): δ 7.86 (d, 1H, J=15.2 Hz), 7.82 (d, 1H, J=8.0 Hz), 7.63 (s, 1H), 7.58 (d, 1H, J=8.0 Hz), 6.59 (d, 1H, J=15.6 Hz), 3.18 (d, 2H, J=7.2 Hz), 2.21~2.12 (m, 1H), 1.33 (s, 9H), 1.10 (d, 6H, J=6.8 Hz),

Step 3: 3-(4-tert-Butyl-2-isobutylaminophenyl)-N-(3-fluoro-4-methanesulfonylamino-5-vinylbenzyl)acrylamide 3-(4-tert-butyl-2-isobutylaminophenyl)acrylic acid (0.08 mmol, 22.02 mg), N-(4-Aminomethyl-2-fluoro-6-vinylphenyl)methanesulfonamide (0.08 mmol, 31.54 mg), DEPC (0.09 mmol, 14.57 µl), and TEA (2 eq, 0.16 mmol, 22.30 µl) were added in DMF. The reaction mixture was stirred overnight. The reaction mixture was purified according to step 2 of Example 27 to obtain a yellow solid (23.1 mg, 57.60%).

mp: 165~167° C.; IR (KBr pellet, cm$^{-1}$): 3238, 2957, 1649, 1608, 1321, 1154;

$^1$H NMR (400 MHz, CD$_3$OD): δ 7.76 (d, 1H, J=15.6 Hz), 7.46 (s, 1H), 7.30 (d, 1H, J=8.0 Hz), 7.16 (dd, 1H, J=17.6, 11.2 Hz), 7.09 (dd, 1H, J=10.4, 1.2 Hz), 6.67 (d, 1H, J=8.0 Hz), 6.64 (s, 1H), 6.42 (d, 1H, J=15.2 Hz), 5.82 (d, 1H, J=17.6 Hz), 5.36 (d, 1H, J=11.2 Hz), 4.47 (s, 2H), 2.29 (s, 3H), 2.96 (d, 2H, J=6.8 Hz), 1.97~1.87 (m, 1H), 1.26 (s, 9H), 0.98 (d, 6H, J=6.8 Hz),

Example 34

3-(4-tert-Butyl-2-isopropylaminophenyl)-N-(3-fluoro-4-methanesulfonylamino-5-vinylbenzyl)acry-lamide

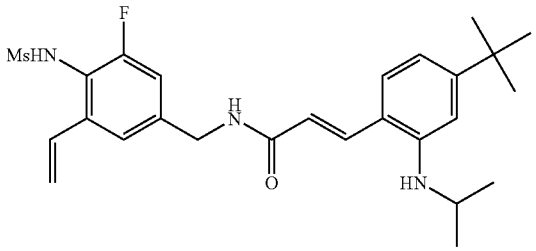

Step 1: 3-(4-tert-Butyl-2-trifluoromethanesulfony-loxyphenyl)acrylic acid ethyl ester After 3-(4-tert-Butyl-2-hydroxyphenyl)acrylic acid ethyl ester (101.9 mg, 0.410 mmol) was added in methylene chloride. The reaction temperature cooled down to −78° C. 2,6-Lutidine (119.5 µl, 1.026 mmol) and triflic anhydride (137.9 µl, 0.820 mmol, 2 eq) were added. The reaction mixture was warmed up to room temperature. The reaction was quenched by adding sat. NaHCO₃ solution. A reaction mixture was extracted with CH₂Cl₂. A combined organic layer was washed with H₂O and brine, dried over Na₂SO₄. The residue was purified with column chromatography (n-Hexane: EtOAc=10:1) to give a syrup (103.9 mg, 72.4%).

¹H NMR (400 MHz, CDCl₃): δ 7.77 (d, J=16.0 Hz, 1H), 7.55 (d, J=8.4 Hz, 1H), 7.34 (dd, J=8.0, 1.6 Hz, 1H), 7.25 (d, J=1.6 Hz, 1H), 6.39 (d, J=16.0 Hz, 1H), 4.20 (q, J=7.2 Hz, 2H), 1.31-1.25 (m, 12H); IR (NaCl Neat, cm⁻¹): 2960, 2871, 1713, 1628, 1607, 1165

Step 2:
3-(4-tert-Butyl-2-isopropylaminophenyl)acrylic acid methyl ester

Tris(dibenzylidene acetone)dipalladium (5%, 0.04 mmol, 37.24 mmol), 1,1'-bis(diphenylphosphino) ferrocene (15%, 0.12 mmol, 67.36 mg), isopropylamine (1.62 mmol, 137.98 µl) and 3-(4-tert-butyl-2-trifluoromethanesulfonyloxyphenyl)-acrylic acid methyl ester (0.81 mmol, 298 mg) were added in toluene under argon atmosphere. Cesium carbonate (1.22 mmol, 395.87 mg) was added into reaction mixture. The reaction mixture was stirred for 12 hrs at 80° C. The reaction mixture was purified according to step 1 of Example 22 to yield a syrup (37.3 mg, 17.28%).

IR (NaCl neat pellet, cm⁻¹): 3428, 2965, 1725, 1638;

¹H NMR (400 MHz, CDCl₃): δ 7.76 (d, 1H, J=15.6 Hz), 7.29 (d, 1H, J=8.0 Hz), 6.71 (d, 1H, J=8.4 Hz), 6.68 (s, 1H), 6.27 (d, 1H, J=15.6 Hz), 3.77 (s, 3H), 3.74~3.67 (m, 1H), 1.28 (s, 9H), 1.24 (d, 6H, J=6.4 Hz),

Step 3:
3-(4-tert-Butyl-2-isopropylaminophenyl)acrylic acid 3-(4-tert-butyl-2-isopropylaminophenyl)acrylic acid methyl ester (0.14 mmol, 37.7 mg) and NaOH (0.68 mmol, 27.39 mg) were added in methanol and water. The reaction mixture was stirred for 12 hrs at room temperature. The reaction mixture was acidified with 5% HCl solution. The mixture was concentrated in vacuo to yield a yellow solid (36.56 mg, 100%).

¹H NMR (400 MHz, CD₃OD): δ 7.84 (d, 1H, J=15.6 Hz), 7.35 (d, 1H, J=8.0 Hz), 6.77 (s, 1H), 6.76 (d, 1H, J=8.0 Hz), 6.26 (d, 1H, J=15.6 Hz), 3.67-3.61 (m, 1H), 1.26 (s, 9H), 1.22 (d, 6H, J=6.4 Hz),

Step 4: 3-(4-tert-Butyl-2-isopropylaminophenyl)-N-(3-fluoro-4-methanesulfonylamino-5-vinylbenzyl)acrylamide 3-(4-tert-butyl-2-isopropylaminophenyl)acrylic acid (0.14 mmol, 36.56 mg), N-(4-Aminomethyl-2-fluoro-6-vinylphenyl)methanesulfonamide (0.15 mmol, 55.17 mg), DEPC (1.2 eq, 0.17 mmol, 25.49%) and TEA (2 eq, 0.28 mmol, 39.02 µl) were added in DMF. The reaction mixture was stirred overnight. The reaction mixture was purified according to step 2 of Example 22 to yield a yellow solid (38.9 mg, 57.03%).

mp: 168~170° C.; IR (KBr pellet, cm⁻¹): 3236, 3022, 2964, 1609, 1321, 1154

¹H NMR (400 MHz, CD₃OD): δ 7.74 (d, 1H, J=15.6 Hz), 7.46 (s, 1H), 7.31 (d, 1H, J=8.0 Hz), 7.16 (dd, 1H, J=17.6, 10.8 Hz), 7.09 (dd, 1H, J=10.4, 1.6 Hz), 6.71 (s, 1H), 6.69 (d, 1H, J=8.0 Hz), 6.41 (d, 1H, J=15.6 Hz), 5.82 (d, 1H, J=17.6 Hz), 5.36 (d, 1H, J=11.2 Hz), 4.47 (s, 2H), 3.74-3.64 (m, 1H), 2.99 (s, 3H), 1.26 (s, 9H), 1.21 (d, 6H, J=6.4 Hz).

Example 35

(R)-3-(4-tert-Butylphenyl)-N-[1-(3-fluoro-4-methanesulfonylamino-5-vinylphenyl)ethyl]propionamide

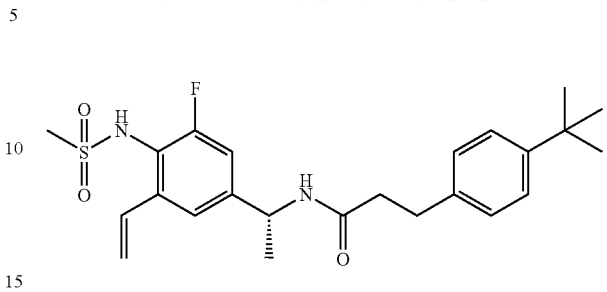

N-[4-(1-Aminoethyl)-2-fluoro-6-vinylphenyl]methanesulfonamide (step 5 of Example 7, 0.08 mmol, 30.6 mg), 3-[4-tert-butyl-2-(3-methylbutylamino) phenyl]propionic acid (0.09 mmol, 18.65), DEPC (0.10 mmol, 14.57 µl) and TEA (0.16 mmol, 22.49 µl) were added in DMF. The reaction mixture was stirred for 12 hrs. The reaction mixture was purified according to Example 21 to yield a solid (27.2 mg, 67.73%).

mp: 154~156° C.;

[α]$_D^{20}$: +8.59 (CHCl₃, c 0.27);

IR (KBr pellet): 3223, 2963, 1645, 1261, 1097 cm⁻¹; ¹H NMR (400 MHz, CDCl₃): δ 7.25 (s, 1H), 7.24 (d, 2H, J=17.6, 11.2 Hz), 7.06 (d, 2H, J=8.0 Hz), 6.86 (dd, 1H, J=10.4, 2.0 Hz), 5.84 (s, 1H), 5.71 (d, 1H, J=17.6 Hz), 5.42 (d, 1H, J=6.8 Hz), 5.39 (d, 1H, J=11.2 Hz), 4.96 (q, 1H, J=6.4 Hz), 3.00 (s, 3H), 2.87 (t, 2H, J=8.0 Hz), 2.43 (t, 2H, J=8.0 Hz), 1.30 (d, 3H, J=6.8 Hz), 1.23 (s, 9H).

Example 36

(R)-3-(4-tert-Butylphenyl)-N-[1-(3-fluoro-4-methanesulfonylamino-5-vinylphenyl)ethyl]acrylamide

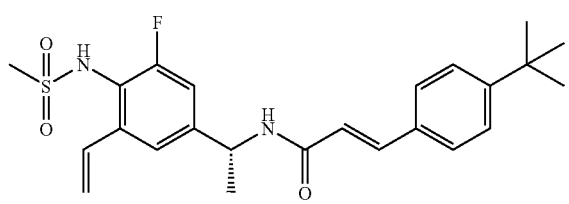

N-[4-(1-Aminoethyl)-2-fluoro-6-vinylphenyl]methanesulfonamide (0.7 mmol, 25.3 mg), 3-[4-tert-butyl-2-(3-methylbutylamino)phenyl]acrylic acid (0.7 mmol, 15.27 mg), DEPC (0.08 mmol, 12.75 µl), and TEA (0.14 mmol, 19.51 µl) were added in DMF. The reaction mixture was stirred for 12 hrs. The reaction mixture was purified according to similar procedure of Example 21 to yield title product (36.1 mg, 100.0%).

mp: 127~129° C.;

[α]$_D^{20}$: −20.33 (CH₃OH, c 1.26);

IR (KBr pellet): 3236, 3087, 2963, 1734, 1325, 1151 cm⁻¹;

¹H NMR (400 MHz, CDCl₃): δ 7.55 (d, 1H, J=15.6 Hz), 7.35 (d, 2H, J=8.4 Hz), 7.29 (d, 2H, J=8.4 Hz), 7.06 (dd, 1H, J=17.6, 10.8 Hz), 6.97 (dd, 1H, J=10.4, 1.6 Hz), 6.33 (d, 1H, J=17.6 Hz), 6.26 (s, 1H), 6.06 (d, 1H, J=7.6 Hz), 5.69 (d, 1H, J=17.6 Hz), 5.33 (d, 1H, J=11.2 Hz), 5.12 (q, 1H, J=7.2 Hz), 2.98 (s, 3H), 1.43 (d, 3H, J=7.2 Hz), 1.24 (s, 9H).

Example 37

3-(4-tert-Butylphenyl)-N-(3-fluoro-4-methanesulfonylamino-5-vinylbenzyl)-2-methylacrylamide

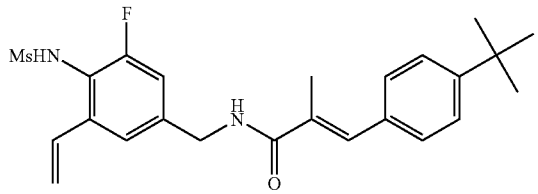

N-(4-Aminomethyl-2-fluoro-6-vinylphenyl)methanesulfonamide (0.15 mmol, 54.21 mg), 3-(4-tert-butyl-phenyl)-2-methylacrylic acid (0.14 mmol, 30 mg), DEPC (1.2 eq, 0.17 mmol, 25.49 μl), and TEA (2 eq, 0.28 mmol, 39.03 μl) were added in DMF. The reaction mixture was stirred for 12 hrs. The reaction mixture was purified according to similar procedure of Example 21 to yield title product (34.8 mg, 55.96%).

mp: 136~138° C.;

IR (KBr pellet, cm$^{-1}$): 3235, 2962, 1645, 1321, 1153;

$^1$H NMR (400 MHz, CDCl$_3$): δ 7.37 (d, 2H, J=8.4 Hz), 7.35 (s, 1H), 7.31 (s, 1H), 7.26 (d, 2H, J=8.4 Hz), 7.12 (dd, 1H, J=17.2, 10.8 Hz), 7.01 (dd, 1H, J=10.0, 1.6 Hz), 6.48 (s, 1H), 5.75 (d, 1H, J=17.2 Hz), 5.39 (d, 1H, J=10.8 Hz), 4.49 (d, 2H, J=6.4 Hz), 3.02 (s, 3H), 2.11 (s, 3H), 1.30 (s, 9H).

Example 38

3-(4-tert-Butylphenyl)-2-fluoro-N-(3-fluoro-4-methanesulfonylamino-5-vinylbenzyl)acrylamide

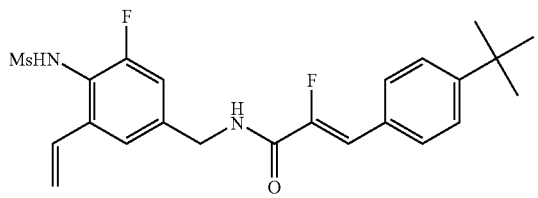

N-(4-Aminomethyl-2-fluoro-6-vinylphenyl)methanesulfonamide (1.1 eq, 0.15 mmol, 53.24 mg), 3-(4-tert-Butylphenyl)-2-fluoroacrylic acid (1 eq, 0.14 mmol, 30 mg), DEPC (1.2 eq, 0.17 mmol, 25.49 μl), and TEA (2 eq, 0.28 mmol, 39.09 μl) were added in DMF under argon atmosphere. The reaction mixture was stirred for 12 hrs. The reaction mixture was purified according to similar procedure of Example 21 to yield title product (30.0 mg, 48%).

mp: 165~167° C.;

IR (KBr pellet, cm$^{-1}$): 3246, 2920, 1644, 1323, 1155;

$^1$H NMR (400 MHz, CDCl$_3$): δ 7.54 (dd, 2H, J=8.8, 2.0 Hz), 7.40 (dd, 2H, J=8.0, 2.0 Hz), 7.35 (s, 1H), 7.24 (d, 1H, J=2.4 Hz), 7.14 (ddd, 1H, J=17.6, 10.8, 2.0 Hz), 7.06 (d, 1H, J=10.0 Hz), 6.95 (dd, 1H, J=39.6, 2.0 Hz), 6.73 (s, 1H), 6.06 (s, 1H), 5.79 (dd, 1H, J=17.2, 1.2 Hz), 5.44 (dd, 1H, J=10.8, 1.2 Hz), 4.56 (d, 2H, J=4.8 Hz), 3.05 (s, 3H), 1.31 (s, 9H)

Example 39

3-[4-tert-Butyl-2-(2-morpholine-4-yl-ethoxy)phenyl]-N-(3-fluoro-4-methanesulfonylamino-5-vinylbenzyl)acrylamide

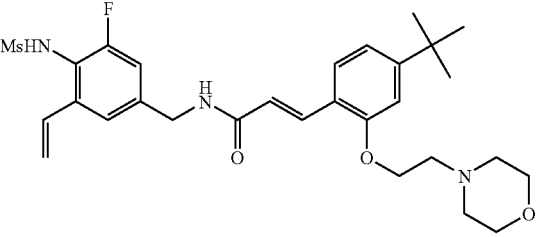

Step 1: 3-[4-tert-Butyl-2-(2-morpholin-4-yl-ethoxy)phenyl]acrylic acid methyl ester 3-(4-tert-Butyl-2-hydroxyphenyl)acrylic acid methyl ester (step 2 of Example 29, 101.5 mg, 0.866 mmole), 4-(2-chloroethyl)morpholine HCl (161.1 mg, 0.866 mmol, 2 eq), and sodium hydride (86.6 mg, 2.166 mmol, 5 eq) were added in DMF under argon atmosphere. The reaction mixture was stirred overnight. After confirming the completion of reaction, DMF was removed under reduced pressure. The residue was extracted with EtOAc. The combined organic layer was washed with H$_2$O and brine, dried over Na$_2$SO$_4$, concentrated in vacuo. The residue was purified with column chromatography (EtOAc) to yield a syrup (33.0 mg, 21.9%).

$^1$H NMR (400 MHz, CDCl$_3$): δ 7.86 (d, J=16.0 Hz, 1H), 7.35 (d, J=8.0 Hz, 1H), 6.93 (dd, J=8.0, 1.6 Hz, 1H), 6.86 (s, 1H), 6.51 (d, J=16.0 Hz, 1H), 4.13 (t, J=6.0 Hz, 1H), 3.72 (s, 3H), 3.68 (t, J=5.2 Hz, 4H), 2.81 (t, J=5.2 Hz, 2H), 2.55 (s, 4H), 1.25 (s, 9H)

Step 2: 3-[4-tert-Butyl-2-(2-morpholine-4-yl-ethoxy)phenyl]-N-(3-fluoro-4-methanesulfonylamino-5-vinylbenzyl)acrylamide 3-[4-tert-Butyl-2-(2-morpholin-4-yl-ethoxy)phenyl]propionic acid methyl ester (15.3 mg, 0.044 mmol, 1 eq) and sodium hydroxide (8.8 mg, 0.220 mmole, 5 eq) were added in methanol and water. The reaction mixture was stirred for 12 hrs. The reaction mixture was acidified with 5% HCl solution. The reaction mixture was concentrated in vacuo to yield solid (14.6 mg, 100%).

3-[4-tert-Butyl-2-(2-morpholine-4-yl-ethoxy)phenyl] acrylic acid (0.044 mmol, 1 eq.), diethylcyanophosphine (8.0 μl, 0.053 mmol, 1.2 eq), N-(4-aminomethyl-2-fluoro-6-vinylphenyl)methanesulfonamide (18.9 mg, 0.053 mmol, 1.2 eq.), and TEA (18.4 μl, 0.132 mmol, 3 eq) were added in DMF under argon atmosphere. The reaction mixture was stirred overnight at room temperature. DMF was removed in vacuo, The residue was extracted with EtOAc. A combined organic layer was washed with brine, dried over Na$_2$SO$_4$, and concentrated in vacuo. The residue was purified with column chromatography (n-Hexane:EtOAc=1:1) to yield a solid (13.1 mg, 53.2. %).

IR (KBr pellet, cm$^{-1}$): 3434, 3254, 2961, 1648, 1608, 1321, 1153, 974;

¹H NMR (400 MHz, CDCl₃): 7.82 (d, J=16.0 Hz, 1H), 7.35 (d, J=8.0 Hz, 1H), 7.29 (s, 1H), 7.08 (dd, J=17.6, 10.8 Hz, 1H), 7.01 (d, J=10.4 Hz, 1H), 6.92 (d, J=8.0 Hz, 1H), 6.85 (s, 1H), 6.50 (d, J=16.0 Hz, 1H), 6.25 (bs. 1H), 5.72 (d, J=18.0 Hz, 1H), 5.75 (d, J=11.2 Hz, 1H), 4.48 (d, J=5.6 Hz, 2H), 4.14 (t, J=5.6 Hz, 2H), 3.65 (t, J=4.4 Hz, 4H), 2.99 (s, 3H), 2.88-2.81 (m. 2H), 2.56 (s. 4H), 1.23 (s, 9H)

Example 40

3-[4-tert-Butyl-2-(tetrahydropyran-4-yloxy)phenyl]-N-(3-fluoro-4-methanesulfonylamino-5-vinylbenzyl)acrylamide

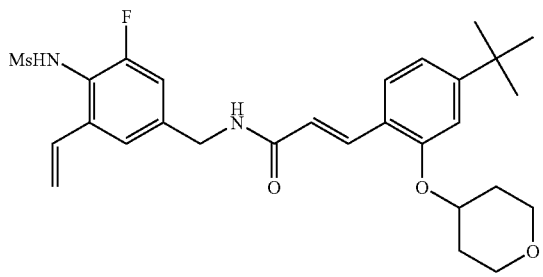

Step 1: 3-[4-tert-Butyl-2-(tetrahydropyran-4-yloxy)-phenyl]acrylic acid methyl ester 3-(4-tert-Butyl-2-hydroxyphenyl)acrylic acid methyl ester (75.9 mg, 0.324 mmole) and 4-methanesulfonic acid tetrahydropyran-4-yl ester (70.1 mg, 0.389 mmol, 1.2 eq), and potassium carbonate (134.3 mg, 0.972 mmol, 5 eq) were added in DMF under argon atmosphere. The reaction mixture was stirred overnight with heating. DMF was removed in vacuo. The residue was extracted with EtOAc. A combined organic layer was washed with H₂O and brine, dried over Na₂SO₄, and concentrated in vacuo. The residue was purified with column chromatography to yield a syrup (43.3 mg).

The syrup and acetic anhydride (174.5 μl, 1.850 mmole, 10 eq) were added in pyridine. The reaction mixture was stirred overnight. The reaction was quenched by adding H₂O. The reaction mixture was extracted with EtOAc. A combined organic layer was washed with sat. CuSO₄, H₂O and brine, dried over Na₂SO₄, and concentrated in vacuo. The residue was purified with column chromatography (n-Hexane: EtOAc=10:1) to yield a syrup (31.5 mg, 43.2%).

¹H NMR (400 MHz, CDCl₃): A −δ7.93 (d, J=16.4 Hz, 1H), 7.39 (d, J=8.0 Hz, 1H), 6.94 (d, J=8.0 Hz, 1H), 6.85 (s, 1H), 6.43 (d, J=16.0 Hz, 1H), 4.50 (step, J=3.6 Hz, 1H), 3.92 (m, 2H), 3.73 (s, 3H), 3.55 (m, 2H), 1.97 (m, 2H), 1.81 (m, 2H), 1.24 (s, 9H)

Step 2: 3-[4-tert-Butyl-2-(tetrahydropyran-4-yloxy)phenyl]-N-(3-fluoro-4-methanesulfonylamino-5-vinylbenzyl)acrylamide 3-[4-tert-Butyl-2-(tetrahydropyran-4-yloxy)phenyl]acrylic acid methyl ester (31.5 mg, 0.099 mmol, 1 eq) and sodium hydroxide (19.8 mg, 0.4955 mmole) were added in methanol and H₂O. The reaction mixture was stirred for 12 hrs. The reaction mixture was acidified with 5% HCl. The mixture was concentrated in vacuo to yield 3-[4-tert-Butyl-2-(tetrahydropyran-4-yloxy)-phenyl]acrylic acid (30.1 mg, 100%).

3-[4-tert-Butyl-2-(tetrahydropyran-4-yloxy)-phenyl]acrylic acid (0.099 mmol, 1 eq.), diethylcyanophosphine (18.1 μl, 0.1119 mmol, 1.2 eq), N-(4-aminomethyl-2-fluoro-6-vinylphenyl)methanesulfonamide (42.5 mg, 0.119 mmol, 1.2 eq.), and TEA (41.4 μl, 0.297 mmol, 3 eq) were added in DMF under argon atmosphere. The reaction mixture was stirred for overnight at room temperature. The reaction mixture was purified according to similar procedure of Example 20 to yield a solid (35.6 mg, 69.6%).

IR (KBr pellet, cm⁻¹): 3423, 3086, 2964, 1655, 1607, 1420, 1329, 1275, 1156;

¹H NMR (400 MHz, CDCl₃): 7.87 (d, J=16.0 Hz, 1H), 7.35 (d, J=8.0 Hz, 1H), 7.23 (s, 1H), 7.03 (dd, J=17.2, 10.8 Hz, 1H), 6.93 (d, J=9.6 Hz, 1H), 6.87 (d, J=8.0 Hz, 1H), 6.84 (s, 1H), 5.66 (d, J=17.6 Hz, 1H), 5.29 (d, J=10.8 Hz, 1H), 4.47-4.41 (m, 3H), 3.88 (t, J=5.6 Hz, 2H), 3.49 (t, J=8.0 Hz, 2H), 2.95 (s, 3H), 1.96-1.93 (m. 2H), 1.75-1.74 (m. 2H), 1.22 (s, 9H)

Example 41

3-[4-tert-Butyl-2-(tetrahydropyran-4-yloxy)phenyl]-N-(3-fluoro-4-methanesulfonylamino-5-vinylbenzyl)propionamide

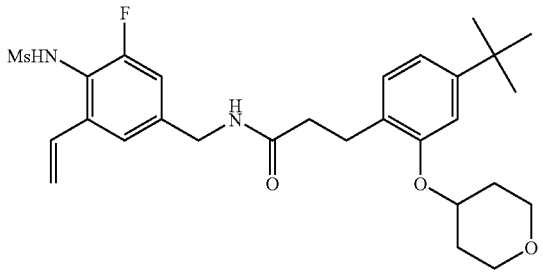

Step 1: 3-[4-tert-Butyl-2-(tetrahydropyran-4-yloxy)phenyl]propionic acid methyl ester 3-[4-tert-Butyl-2-(tetrahydropyran-4-yloxy)phenyl]acrylic acid methyl ester (14.4 mg, 0.045 mmole) and 10 wt. % palladium were added in MeOH. The reaction mixture was stirred overnight under hydrogen atmosphere. The reaction mixture was filtered with celite pad. The filterate was concentrated in vacuo and purified with column chromatography to yield a syrup (14.1 mg, 97.3%).

¹H NMR (400 MHz, CDCl₃): δ 7.01 (d, J=8.4 Hz, 1H), 6.83 (dd, J=8.0, 1.6 Hz, 1H), 6.78 (d, J=1.6 Hz, 1H), 4.48 (step, J=3.6 Hz, 1H), 3.90 (step, J=3.6 Hz, 2H), 3.60 (s, 3H), 3.56 (step, J=3.6 Hz, 2H), 2.85 (t, J=8.0 Hz, 2H), 2.56 (t, J=8.0 Hz, 2H), 2.00-1.93 (m, 2H), 1.79-1.71 (m, 2H), 1.23 (s, 9H)

Step 2: 3-[4-tert-Butyl-2-(tetrahydropyran-4-yloxy)phenyl]-N-(3-fluoro-4-methanesulfonylamino-5-vinylbenzyl)propionamide 3-[4-tert-Butyl-2-(tetrahydropyran-4-yloxy)phenyl]propionic acid methyl ester (14.1 mg, 0.044 mmol, 1 eq) and sodium hydroxide (8.8 mg, 0.220 mmole, 5 eq) were added in methanol and H₂O. The reaction mixture was stirred for 12 hrs. The reaction mixture was acidified with 5% HCl solution. The reaction mixture was concentrated in vacuo to yield 3-[4-tert-Butyl-2-(tetrahydropyran-4-yloxy)phenyl]propionic acid (13.5 mg, 100%).

3-[4-tert-Butyl-2-(tetrahydropyran-4-yloxy)phenyl]propionic acid (0.044 mmol, 1 eq.), diethylcyanophosphine 8.0 μl (0.053 mmol, 1.2 eq), N-(4-aminomethyl-2-fluoro-6-vinylphenyl)methanesulfonamide 19.0 mg (0.053 mmol, 1.2 eq.), and TEA (18.4%, 0.132 mmol, 3 eq) were added in DMF under argon atmosphere. The reaction mixture was stirred overnight at room temperature. DMF was removed in vacuo. The residue was extracted with EtOAc. The residue was washed with brine, dried over $Na_2SO_4$, and concentrated in vacuo. The residue was purified with column chromatography (Hexane:EtOAc=1:1) to yield a solid (23.4 mg, 99.8%).

IR (KBr pellet, cm$^{-1}$): 3423, 3086, 2964, 1655, 1607, 1420, 1329, 1275, 1156;

$^1$H NMR (400 MHz, CDCl$_3$): 7.21 (s, 1H), 7.16-7.01 (m, 2H), 6.91 (s, 1H), 6.85 (d, J=8.0 Hz, 1H), 6.32 (s, 1H), 5.97 (s, 1H), 5.69 (d, J=17.6 Hz, 1H), 5.36 (d, J=11.2 Hz, 1H), 4.44 (sept, J=3.6 Hz, 1H), 4.33 (d, J=6.0 Hz, 2H), 3.87 (sept, J=3.6 Hz, 1H), 3.51 (sept, J=3.6 Hz, 2H), 2.98 (s, 3H), 2.91-2.87 (m. 3H), 2.50 (t, J=7.2 Hz, 2H), 1.96-1.91 (m, 2H), 1.73-1.65 (m, 2H), 1.22 (s, 9H).

Example 42

(R)-3-(4-tert-Butylphenyl)-N-[1-(4-methanesulfonylamino-3-vinylphenyl)ethyl]-2-methylacrylamide

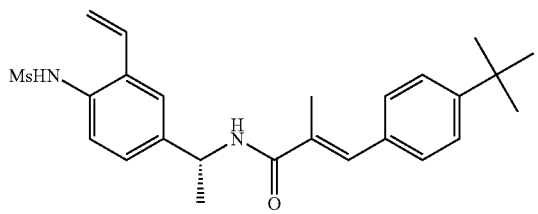

N-[4-(1-aminoethyl)-2-vinylphenyl]methanesulfonamide (0.26 mmol, 58.6 mg), 3-(4-tert-butylphenyl)-2-methylacrylic acid (0.28 mmol, 62.13 mg), DEPC (1.2 eq, 0.31 mmol, 47.34 μl), and TEA (2 eq, 0.52 mmol, 72.48 μl) were added in DMF under argon atmosphere. The reaction mixture was stirred for 12 hr. The reaction mixture was purified according to similar procedure of Example 22 to yield solid (60.8 mg, 54.87%).

$[α]_D^{20}$ −24.96 (CHCl$_3$, c 0.125); Mp: 97~99° C.;

IR (KBr pellet, cm$^{-1}$): 3272, 2964, 1646, 1322;

$^1$H NMR (400 MHz, CDCl$_3$): δ 7.45 (d, 1H, J=2.0 Hz), 7.39 (s, 1H), 7.36 (d, 2H, J=8.0 Hz), 7.30 (s, 1H), 7.25 (d, 2H, J=8.0 Hz), 6.91 (dd, 1H, J=17.2, 11.2 Hz), 6.72 (s, 1H), 6.14 (d, 1H, J=7.6 Hz), 5.69 (d, 1H, J=17.2 Hz), 5.42 (d, 1H, J=11.2 Hz), 5.18 (quin, 1H, J=6.8 Hz), 2.94 (s, 3H), 2.09 (s, 3H), 1.52 (d, 3H, J=6.8 Hz), 1.30 (s, 9H).

Example 43

3-(4-tert-Butylphenyl)-N-(3-fluoro-4-methanesulfonylamino-5-vinylbenzyl)-2-methylpropionamide

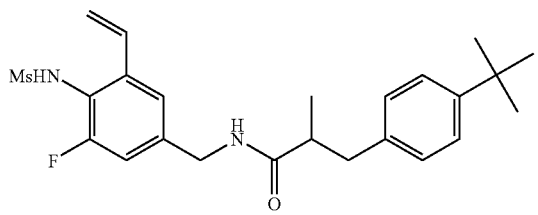

Step 1: 3-(4-tert-Butylphenyl)-2-methylpropionic acid 3-(4-tert-butylphenyl)-2-methylacrylic acid (40.9 mg, 0.19 mmol) and 10 wt. % palladium on activated carbon were added in methanol. The reaction mixture was stirred for 5 hrs under H$_2$ gas. The reaction mixture was filtered with Celite. The filerate was concentrated in vacuo to obtain title compound (39.1 mg, 93.47%).

$^1$H NMR (400 MHz, CD$_3$OD): δ 7.25 (d, 2H, J=8.4 Hz), 7.07 (d, 2H, J=8.4 Hz), 2.92 (q, 1H, J=6.4 Hz), 2.67~2.54 (m, 2H), 1.25 (s, 9H), 1.08 (d, 3H, J=6.8 Hz).

Step 2: 3-(4-tert-Butylphenyl)-N-(3-fluoro-4-methanesulfonylamino-5-vinylbenzyl)-2-methylpropionamide N-(4-aminomethyl-2-fluoro-6-vinylphenyl)methanesulfonamide (0.10 mmol, 35.0 mg), 3-(4-tert-butylphenyl)-2-methylpropionic acid (0.11 mmol, 23.65 mg), DEPC (0.12 mmol, 18.21 μl), and TEA (0.20 mmol, 27.88 μl) were added in DMF under argon atmosphere. The reaction mixture was stirred for 12 hrs. The reaction mixture was purified according to similar procedure of Example 21 to yield a solid (37.1 mg, 83.14%).

mp: 156~158° C.; IR (KBr pellet, cm$^{-1}$): 3288, 3229, 2964, 1647, 1321, 1155

$^1$H NMR (400 MHz, CDCl$_3$): δ 7.26 (d, 2H, J=8.4 Hz), 7.20 (s, 1H), 7.10 (dd, 1H, J=17.6, 11.2 Hz), 7.06 (d, 2H, J=8.4 Hz), 6.79 (dd, 1H, J=10.4, 1.6 Hz), 6.20 (s, 1H), 5.72 (d, 1H, J=17.2 Hz), 5.67 (t, 1H, J=6.0 Hz), 5.40 (d, 1H, J=11.2 Hz), 4.30 (d, 2H, J=6.0 Hz), 3.02 (s, 3H), 3.00~2.89 (m, 1H), 2.66~2.60 (m, 1H), 2.51~2.43 (m, 1H), 1.26 (s, 9H), 1.19 (d, 3H, J=6.8 Hz).

Example 44

N-{4-[3-(4-chlorobenzyl)ureidomethyl]-2-vinylphenyl}methane sulfonamide

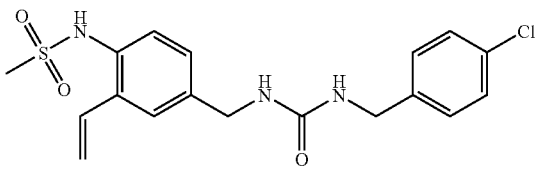

As described in scheme 12, (4-methanesulfonylamino-3-vinylbenzyl)carbamic acid t-butylester (50 mg, 0.153 mmol) and triethylamine (0.1 ml) and 4-chlorobenzylamine (26 mg) were stirred for one night in the presence of acetonitrile solvent. The solvent was removed from the reaction mixture and purified by column chromatography to yield the purposed compound (9 mg).

$^1$H NMR (300 MHz, CDCl$_3$): 7.45 (s, 1H), 7.41 (m, 2H), 7.29 (m, 4H), 6.90 (dd, 1H, J=17.7, 11.1 Hz), 6.44 (bs, 1H), 5.73 (d, 1H, J=17.4 Hz), 5.55 (s, 1H), 5.48 (d, 1H, J=11.1 Hz), 4.90 (bs, 1H), 4.34 (m, 4H), 2.99 (s, 3H)

Example 45

3-[4-(tert-butyl)phenyl]-N-[4-(methanesulfony-lamino)-3-vinylbenzyl]propionamide

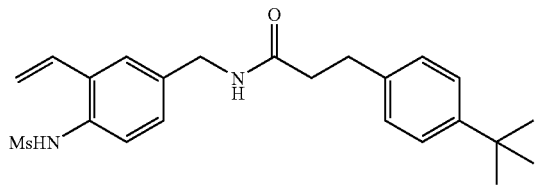

Step 1: tert-butyl N-[4-(methanesulfonylamino)-3-vinylbenzyl]carbamate tert-Butyl N-[4-(methanesulfonylamino)-3-iodobenzyl] carbamate (1.0 g, 2.3 mmol) was dissolved in toluene (20 mL). Tributyl vinyltin (0.8 mL, 2.8 mmol) and Pd(PPh3)$_4$ (140 mg, 0.12 mmol) were dropwisely added. The reaction mixture was stirred for 4 hrs in reflux. Toluene was removed in vacuo. The residue was extracted with EtOAc. A combined organic layer was washed with H$_2$O, brine, dried over MgSO$_4$, and concentrated in vacuo. The residue was purified with column chromatography (EtOAc: n-hexane=1:2) to yield title compound (740 mg, 97%).

$^1$H-NMR (300 MHz, CDCl$_3$): δ 1.44 (s, 9H), 2.96 (s, 3H), 4.29 d, 2H, J=5.9 Hz), 4.86 (bs, 1H), 5.46 (dd, 1H, J=11.0, 0.93 Hz), 5.71 (dd, 1H, J=17.0, 0.93 Hz), 6.32 (bs, 1H), 6.87 (dd, 1H, J=17.0, 11.0 Hz), 7.20 (dd, 1H, J=8.3, 1.8 Hz), 7.38 (d, 1H, J=2.0 Hz), 7.41 (d, 1H, J=8.2 Hz)

Step 2: N-[4-(aminomethyl)-2-vinylphenyl]methane-sulfonamide tert-butyl N-[4-(methanesulfonylamino)-3-vinylbenzyl] carbamate (100 mg, 0.23 mmol) and TFA (0.4 ml) were added in methylene chloride (2 mL). The reaction mixture was stirred overnight at room temperature. The reaction mixture was concentrated in vacuo to yield title compound (100%).

Step 3: 3-[4-(tert-butyl)phenyl]-N-[4-(methanesulfo-nylamino)-3-vinyl benzyl]propionamide N-[4-(aminomethyl)-2-vinylphenyl]methanesulfonamide (0.23 mol) and was suspended in methylene chloride and treated with triethylamine followed by 3-(4-tert-butyl-phenyl)-propionic acid and DMTMM (40 mg). The resulting mixture was stirred for 2 days at ambient temperature and concentrated under reduced pressure. The crude residue was column-chromatographed (hexane/ethylacetate=3/2) to yield a white solid (73%).

$^1$H-NMR (300 MHz, CDCl$_3$): δ 1.28 (s, 9H), 2.51 (t, 2H, J=7.6 Hz), 2.92-2.97 (m, 5H), 4.38 (d, 2H, J=5.9 Hz), 5.47 (d, 1H, J=11.0 Hz), 5.62 (bs, 1H), 5.69 (d, 1H, J=18.0 Hz), 6.23 (bs, 1H), 6.84 (dd, 1H, J=17.0, 11.0 Hz), 7.09-7.14 (m, 3H), 7.25-7.41 (m, 4H)

IR (neat) cm$^{-1}$ 1 3295, 2960, 1648, 1541, 1324, 1152
Mass (FAB): 415 [M+H]+

Example 46

3-[4-(tert-butyl)phenyl]-N-[3-fluoro-4-(methane-sulfonylamino)-5-vinylbenzyl]propionamide

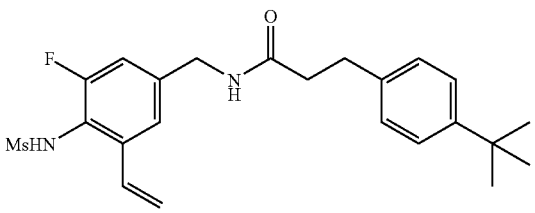

Title compound (63%) was synthesized according to procedure similar to the procedure employed for the synthesis of Example 45.

$^1$H-NMR (300 MHz, CDCl$_3$): δ 1.28 (s, 9H), 2.52 (t, 2H, J=7.6 Hz), 2.96 (t, 2H, J=7.7 Hz), 3.05 (s, 3H), 4.39 (d, 2H, J=6.0 Hz), 5.44 (d, 1H, J=11.0 Hz), 5.69 (bs, 1H), 5.76 (d, 1H, J=17.0 Hz), 5.92 (bs, 1H), 6.92 (d, 1H, J=10.0 Hz), 7.08-7.18 (m, 3H), 7.22-7.32 (m, 3H)

IR (neat) cm 1 3233, 2922, 1646, 1540, 1317, 1151
Mass (FAB) 433 [M+H]+

Example 47

3-(4-tert-butyl-phenyl)-N-(3-ethynyl-5-fluoro-4-methanesulfonylamino-benzyl)-propionamide

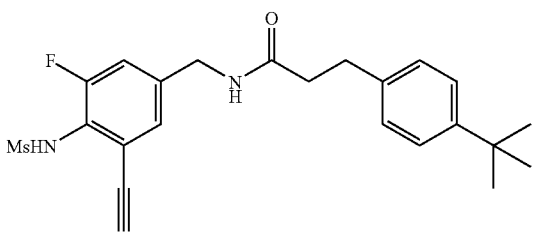

Title compound (90%) was synthesized according to procedure similar to the procedure employed for the synthesis of Example 45.

$^1$H-NMR (300 MHz, CDCl$_3$): δ 1.28 (s, 9H), 2.49-2.54 (t, 2H), 2.92-2.97 (t, 2H) 3.23 (s, 3H), 3.46 (s, 1H), 4.32 (d, 2H, J=6.1 Hz), 5.68 (bs, 1H), 6.39 (bs, 1H), 6.99-7.02 (d, 2H, J=10.6 Hz), 7.09-7.18 (m, 3H), 7.28-7.31 (m, 2H)

IR (neat) cm-1 3269, 2959, 1581, 1482, 1332, 1154
Mass (FAB+) 431 [M+H]+

Example 48

N-{4-[3-(4-tert-Butyl-benzyl)-ureidomethyl]-5-methoxy-2-vinyl-phenyl}-methanesulfonamide

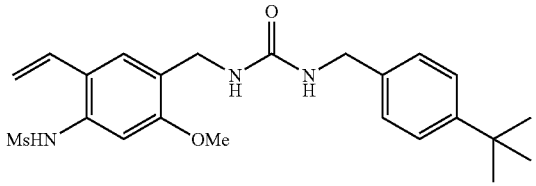

Step 1: (4-Amino-2-methoxy-benzyl)-carbamic acid tert-butyl ester

2-Methoxy-4-nitro-benzonitrile (1.78 g, 10 mmol) and Pd/C (4 small spatula) were suspended in MeOH containing c-HCl, and the mixture was hydrogenated under 40 psi hydrogen pressure for 4 hrs. The reaction mixture was filtered through celite, and the filtrate was concentrated under reduced pressure to yield a yellow solid (1.58 g, 70%). The solid was dissolved in THF, and the solution was cooled to 0° C. Triethylamine (1.43 g, 14 mmol) was added to the solution followed by Boc$_2$O, and the reaction mixture was stirred overnight at ambient temperature. The reaction was quenched by adding water and EtOAc, and the organic phase was separated. The aqueous phase was extracted three times with EtOAc, and the combined organic layer was washed with brine, dried over anhyd. MgSO$_4$, filtered, and concentrated under reduced pressure. The crude residue was column-chromatographed (hexane/ethylacetate=1/1 to 1/2) to yield a white solid (1.3 g, 73%).

$^1$HNMR (300 MHz, CDCl3): 7.03 (d, 1H, J=8.4 Hz), 6.23 (m, 2H), 4.91 (bs, 1H), 4.18 (d, 2H, J=5.7 Hz), 3.78 (s, 3H), 3.72 (bs, 2H), 1.44 (s, 9H).

Step 2: (4-Amino-5-iodo-2-methoxy-benzyl)-carbamic acid tert-butyl ester

To a suspension of iodine and AgNO$_2$ in methylene chloride was added a solution of (4-amino-2-methoxy-benzyl)-carbamic acid tert-butyl ester (1.3 g, 5.15 mmol) in methylene chloride at 0° C., and the mixture was stirred for 30 min at 0° C. and more stirred for 30 min at ambient temperature. The reaction was quenched with Na$_2$S$_2$O$_3$. The reaction solution was extracted with methylenechloride, washed with water and brine, dried over anhyd. MgSO$_4$, filtered and concentrated under reduced pressure. The obtained liquid was column-chromatographed (hexane/ethylacetate=2/1) to yield (4-amino-5-iodo-2-methoxy-benzyl)-carbamic acid tert-butyl ester (925 mg, 47%).

$^1$HNMR (300 MHz, CDCl3): 7.45 (s, 1H), 6.28 (s, 1H), 4.88 (bs, 1H), 4.14 (d, 2H, J=6.0 Hz), 4.08 (bs, 2H), 3.77 (s, 3H), 1.45 (s, 9H).

Step 3: (4-Amino-2-methoxy-5-vinyl-benzyl)-carbamic acid tert-butyl ester

To a solution of (4-amino-5-iodo-2-methoxy-benzyl)-carbamic acid tert-butyl ester (700 mg, 1.85 mmol) and tributylvinyltin (783 mg, 2.68 mmol) in toluene was added Pd(PPh3)4 (214 mg, 0.19 mmol) under argon. The resulting mixture was heated with reflux for 8 hrs, filtered through celite, and then concentrated under reduced pressure. The crude residue was column-chromatographed (hexane/ethylacetate=2/1 to 1/1) to yield (4-amino-2-methoxy-5-vinyl-benzyl)-carbamic acid tert-butyl ester (220 mg, 43%).

$^1$HNMR (300 MHz, CDCl3): 7.18 (s, 1H), 6.67 (dd, 1H, J=11 and 17 Hz), 6.19 (s, 1H), 5.53 (dd, 1H, J=0.9 and 17 Hz), 5.20 (dd, 1H, J=0.9 and 11 Hz), 4.91 (bs, 1H), 4.20 (d, 2H, J=6.0 Hz), 3.79 (s, 3H), 1.44 (s, 9H).

Step 4: (4-Methanesulfonylamino-2-methoxy-5-vinyl-benzyl)-carbamic acid tert-butyl ester To a ice-cooled solution of (4-amino-2-methoxy-5-vinyl-benzyl)-carbamic acid tert-butyl ester (220 mg, 0.79 mmol) in methylene chloride was added triethylamine (132 L) followed by methanesulfonyl chloride (72 L). The mixture was warmed up to room temperature and stirred for 4 hrs. The reaction was quenched with water, and the reaction solution was extracted with methylenechloride, washed with water and brine, dried over anhyd. MgSO$_4$, filtered and concentrated under reduced pressure. The resulting residue was treated with 1N NaOH/MeOH/THF (1/2/1) for 2 hrs, and then neutralized by adding 1N HCl. After evaporating methanol, water was added to the residue. The resulting mixture was extracted with EtOAc, and the combined organic layer was washed with brine, dried over anhyd. MgSO$_4$, filtered, and concentrated under reduced pressure. The crude residue was column-chromatographed (hexane/ethylacetate=1/1) to yield a white solid (260 mg, 92%).

$^1$HNMR (300 MHz, CDCl$_3$): 7.38 (s, 1H), 7.04 (s, 1H), 6.77 (dd, 1H, J=11 and 17 Hz), 6.52 (bs, 1H), 5.63 (d, 1H, J=17 Hz), 5.37 (d, 1H, J=11 Hz), 5.02 (bs, 1H), 4.28 (d, 2H, J=6.0 Hz), 3.79 (s, 3H), 2.96 (s, 3H), 1.45 (s, 9H).

Step 5: N-{4-[3-(4-tert-Butyl-benzyl)-ureidomethyl]-5-methoxy-2-vinyl-phenyl}-methanesulfonamide To a ice-cooled solution of (4-methanesulfonylamino-2-methoxy-5-vinyl-benzyl)-carbamic acid tert-butyl ester (220 mg, 0.73 mmol) in methylene chloride was treated with trifluoroacetic acid (100 mg, 0.88 mmol)) for 1 hr, and then concentrated under reduced pressure. The part of crude residue (100 mg, 0.27 mmol) was suspended in methylene chloride and treated with triethylamine followed by (4-tert-butyl-benzyl)-carbamic acid phenyl ester (92 mg, 0.32 mmol). The resulting mixture was heated with reflux for 3 days and concentrated under reduced pressure. The crude residue was column-chromatographed (hexane/ethylacetate=1/2) to yield a white solid (8.8 mg, 7.0%).

$^1$HNMR (300 MHz, CDCl$_3$): 7.39 (s, 1H), 7.34 (d, 2H, J=8.1 Hz), 7.24 (d, 2H, J=8.1 Hz), 7.00 (s, 1H), 6.77 (dd, 1H, J=11 and 17 Hz), 6.59 (bs, 1H), 5.63 (d, 1H, J=17 Hz), 5.37 (d, 1H, J=11 Hz), 4.93 (bs, 1H), 4.77 (bs, 1H), 4.32 (d, 4H, J=5.1 Hz), 3.76 (s, 3H), 2.93 (s, 3H), 1.30 (s, 9H).

Example 49

3-(4-tert-Butyl-phenyl)-N-(4-methanesulfonylamino-2-methoxy-5-vinyl-benzyl)-acrylamide

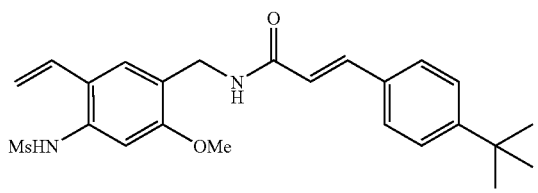

To a ice-cooled solution of 4-methanesulfonylamino-2-methoxy-5-vinyl-benzylamine and HCl salt (220 mg, 0.73 mmol) prepared in the synthesis of Example 48 in methylene chloride was treated with trifluoroacetic acid (100 mg, 0.88 mmol)) for 1 hr, and then concentrated under reduced pressure. The part of the crude residue (50 mg, 0.13 mmol) was suspended in methylene chloride and treated with triethylamine followed by 3-(4-tert-butyl-phenyl)-acrylic acid (30 mg) and DMTMM (40 mg). The resulting mixture was stirred for 2 days at ambient temperature and concentrated under reduced pressure. The crude residue was column-chromatographed (hexane/ethylacetate=3/2) to yield a white solid (11 mg, 19%).

$^1$HNMR (300 MHz, CDCl3): 7.63 (d, 2H, J=16 Hz), 7.45 (s, 1H), 7.43 (d, 2H, J=8.1 Hz), 7.38 (d, 2H, J=8.1 Hz), 7.09 (s, 1H), 6.74 (dd, 1H, J=11 and 17 Hz), 6.48 (s, 1H), 6.36 (d, 1H, J=16 Hz), 6.12 (t, 1H), 5.63 (d, 1H, J=17 Hz), 5.37 (d, 1H, J=11 Hz), 4.54 (d, 2H, J=6.0 Hz), 3.90 (s, 3H), 2.96 (s, 3H), 1.32 (s, 9H).

Example 50

1-(4-Amino-3-fluoro-5-vinyl-benzyl)-3-(4-tert-butyl-benzyl)-urea

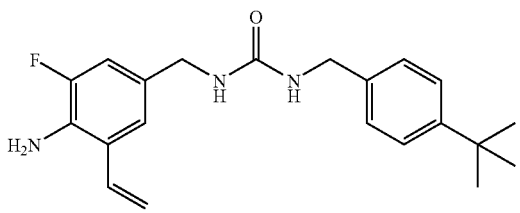

Step 1: 1-(4-amino-3-fluoro-benzyl)-3-(4-t-butyl-benzyl)-urea

To the 50 ml of round bottom flask were put 4-amino-3-fluorobenzylamine hydrochloride (0.46 g, 3.28 mmol) and 4-t-butylbenzylcarbamic acid phenyl ester (1.1 eq, 1.02 g). And to this mixture was poured 20 ml acetonitrile and added triethylamine (excess, 0.5 ml) and refluxed 12 hours. After confirming the completion of the reaction with TLC, the reaction mixture was extracted with ethylacetate, washed with 1N HCl solution. And the combined organic layer was dried over MgSO$_4$, filtered and concentrated under reduced pressure. The obtained liquid was column-chromatographed (n-hexane/ethyl acetate=1/1).

Yield: 0.5 g, 46.4%

Step 2: 1-(4-amino-3-fluoro-5-iodo-benzyl)-3-(4-t-butyl-benzyl)-urea

To the 50 ml of round bottom flask were put 1-(4-amino-3-fluoro-benzyl)-3-(4-t-butyl-benzyl)-urea (0.25 g, 0.76 mmol) and Ag$_2$SO$_4$ (1.1 eq, 0.26 g) and then cooled to 0° C. And to this mixture was poured 20 ml ethanol and added I$_2$ (1.0 eq, 0.193 g) portionwise and stirred for 3 hours at room temperature. After confirming the completion of the reaction with TLC, the reaction mixture was filtered through celite and concentrated under reduced pressure.

Step 3: 1-(4-amino-3-fluoro-5-vinyl-benzyl)-3-(4-t-butyl-benzyl)-urea

To the 50 ml round bottom flask were put 1-(4-amino-3-fluoro-5-iodo-benzyl)-3-(4-t-butyl-benzyl)-urea (0.17 g, 0.37 mmol) and Pd(PPh$_3$)$_4$ (0.05 eq, 21.3 mg). And to this reaction mixture was added 20 ml toluene and tributyl(vinyl) tin (1.1 eq, 0.13 g) by syringe and refluxed for 2 hours. After confirming the completion of the reaction with TLC, the reaction mixture was extracted with ethylacetate, washed with 1M KF solution. And the combined organic layer was dried over MgSO$_4$, filtered and concentrated under reduced pressure. The obtained liquid was column-chromatographed (n-hexane/ethyl acetate=2/1).

Yield: 88 mg, 66.9%

Example 51

3-(4-tert-Butyl-phenyl)-N-(4-methanesulfonylamino-3-vinyl-benzyl)-2-phenyl-acrylamide

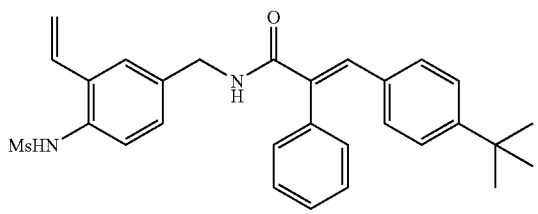

Step 1: 3-(4-tert-Butyl-phenyl)-2-phenyl-acrylic acid

Phenyl acetic acid (489 mg, 3.59 mmol) and 4-t-butylbenzaldehyde (573 mmg, 3.53 mmol), TEA (5 ml) and acetic anhydride (5 ml) were added in round flask. A reaction mixture was heated and stirred overnight. The reaction mixture was poured into 5% HCl aqueous solution (30 ml). A aqueous solution was extracted with MC (30 ml×3). A combined organic layer was dried over MgSO$_4$ and then concentrated in vacuo. The crude residue was column-chromatographed (hexane/ethylacetate=4/1) to yield a white solid (382 mg, 73%)

$^1$HNMR (300 MHz, CDCl$_3$): 7.88 (s, 1H), 7.37~7.35 (m, 4H), 7.23~7.21 (m, 2H), 7.14 (d, 2H, J=8.4 Hz), 7.96 (d, 2H, J=8.4 Hz) 1.20 (s, 9H)

Step 2: 3-(4-tert-butyl-phenyl)-N-(4-methanesulfonylamino-3-vinyl-benzyl)-2-phenyl-acrylamide 4-Methanesulfonylamino-3-vinyl-benzylamine and HCl salt (153 mg, 0.582 mmol) were reacted with 3-(4-tert-butyl-phenyl)-2-phenyl-acrylic acid (160.4 mg) to give 3-(4-tert-butyl-phenyl)-N-(4-methanesulfonylamino-3-vinyl-benzyl)-2-phenyl-acrylamide (130.8 mg, 46%).

$^1$HNMR (300 MHz, CDCl$_3$): 7.84 (s, 1H), 7.43~7.38 (m, 3H), 7.32 (d, 2H, J=8.1 Hz), 7.26~7.22 (m, 3H), 7.11 (m, 2H), 7.01 (m, 2H), 6.89 (m, 2H), 6.12 (br, 1H), 5.76 (t, 1H, J=5.4 Hz), 4.40 (d, 1H, J=6 Hz), 2.95 (s, 3H), 1.19 (s, 9H).

IR (cm$^{-1}$): 2962, 1654, 1606, 1513, 1365, 1154.

Example 52

N-(4-Methanesulfonylamino-3-vinyl-benzyl)-2,3-diphenyl-acrylamide

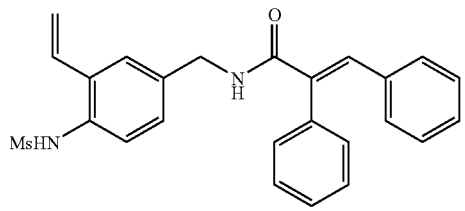

Step 1: 2,3-Diphenyl-acrylic acid

Phenyl acetic acid (1.94 g, 14.24 mmol) and benzaldehyde (1.491 g, 14.05 mmol), TEA (5 ml) and acetic anhydride (5 ml) were reacted to give 2,3-diphenyl-acrylic acid as similar procedure.

$^1$HNMR (300 MHz, CDCl$_3$): 8.06 (s, 1H), 7.49 (m, 3H), 7.37~7.19 (m, 5H), 7.16 (m, 2H).

Step 2: N-(4-Methanesulfonylamino-3-vinyl-benzyl)-2,3-diphenyl-acrylamide

4-Methanesulfonylamino-3-vinylbenzylamine and HCl salt (131 mg, 0.499 mmol) were reacted with 2,3-diphenyl-acrylic acid (115 mg, 0.512 mmol) prepared by the reported procedure to give N-(4-methanesulfonylamino-3-vinyl-benzyl)-2,3-diphenyl-propionamide (146 mg, 68%).

$^1$HNMR (300 MHz, CDCl$_3$): 7.85 (s, 1H), 7.37 (m, 3H), 7.29 (m, 3H), 7.07 (m, 4H), 6.94 (m, 3H), 6.84 (s, 1H), 5.87 (t, 1H, J=5.7 Hz), 5.63 (dd, 1H, J=17.4, 1.2 Hz), 3.38 (s, 1H, J=10.8, 0.9), 4.44 (d, 2H, J=6.3 Hz), 2.90 (s, 3H).

IR (cm$^{-1}$): 3176, 1652, 1595, 1515, 1311.

Example 53

(R)—N-(4-{1-[3-(4-tert-Butylphenyl)ureido]ethyl}-2-vinylphenyl)methanesulfonamide

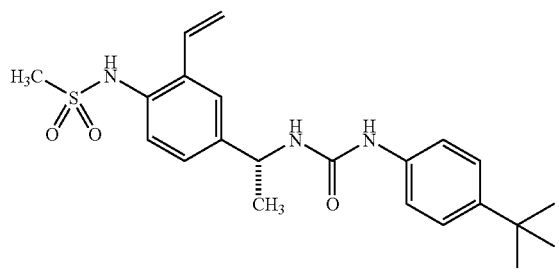

N-[4-(1-Aminoethyl)-2-vinylphenyl]methanesulfonamide (236.7 mg, 0.985 mmol, 1 eq.) and Triethylamine (274.6 μl, 1.970 mmol, 2 eq.) were added in methylene chloride. The reaction mixture was cooled down to 0° C. 4-tert-Butylphenyl isocyanate (192.5 μl, 1.083 mmol, 1.3 eq.) was added. The reaction mixture was stirred for 40 min. Methylene chloride was removed in vacuo. The residue was purified with column chromatography (n-Hx:EA=2:1) to yield title compound (155.4 mg, 38%) as white solid.

IR (KBr pellet, cm$^{-1}$): 3350, 3025, 2962, 2863, 1648;

$^1$H NMR (400 MHz, CDCl$_3$): 7.30 (d, 1H, J=1.6 Hz), 7.18 (d, 2H, J=8.4 Hz), 7.15 (d, 1H, J=8.4 Hz), 7.08 (d, 2H, J=8.4 Hz), 7.03 (dd, 1H, J=8.4, 1.6 Hz), 6.96 (s, 1H), 6.80 (dd, 1H, J=17.2, 11.2 Hz), 5.55 (d, 1H, J=17.2 Hz), 5.26 (d, 1H, J=11.2H), 4.81 (q, 1H, J=6.4 Hz), 2.83 (s, 3H), 1.25 (d, 3H, J=6.4 Hz), 1.18 (s, 9H)

Example 54

(R)—N-(4-{1-[3-(4-tert-Butylphenyl)ureido]ethyl}-2-trimethylsilanylethynylphenyl)methanesulfonamide

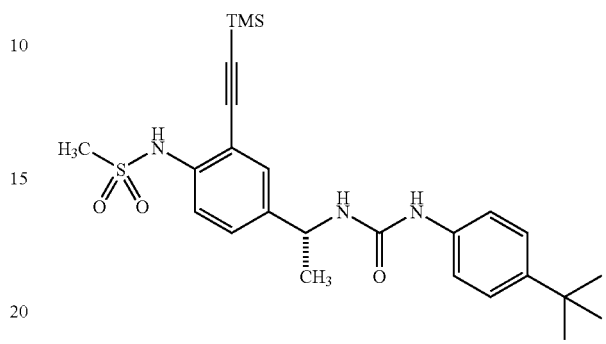

Step 1: (R)-[1-(4-Amino-3-trimethylsianylethynylphenyl)ethyl]carbamic acid tert-butyl ester

[1-(4-Amino-3-iodo-phenyl)-ethyl]-carbamic acid tert-butyl ester (100 mg, 0.276 mmol, 1 eq.), dichloro(bistriphenylphosphine)palladium (9.8 mg, 0.014 mmol, 0.05 eq.) and copper iodide (2.6 mg, 0.014 mmol, 0.05 eq.) were dissolved in THF. After stirring for 30 min, triethylamine (115.4 μl, 0.828 mmol, 3 eq.), and (trimethylsilyl)acetylene (49.6 μl, 0.359 mmol, 1.3 eq) were added into the reaction mixture. The reaction mixture was stirred overnight. The reaction mixture was evaporated in vacuo. The residue was purified with column chromatography (n-Hx:EA=5:1) to yield title compound (70.8 mg) as yellow liquid.

[α]$^{23}_D$: +40.80° (c 0.2, CHCl$_3$); IR (NaCl neat, cm$^{-1}$): 3374, 2974, 2928, 2141, 1694; $^1$H NMR (400 MHz, CDCl$_3$): 7.23 (d, 1H, J=1.6 Hz), 7.05 (dd, 1H, J=8.4, 1.6 Hz), 6.64 (d, 1H, J=8.4 Hz), 4.73-4.71 (m, 1H), 4.63 (bs, 1H), 4.09 (bs, 2H), 1.42 (s, 9H), 1.39 (d, 3H, J=6.8 Hz), 0.26 (s, 9H)

Step 2: (R)-[1-(4-Methanesulfonylamino-3-trimethylsilanylethynyl phenyl)ethyl]carbamic acid tert-butyl ester (R)-[1-(4-Amino-3-trimethylsilanylethynylphenyl)ethyl] carbamic acid tert-butyl ester (67.9 mg, 0.20 mmol, 1 eq.), methansulfonic anhydride (39.1 mg, 0.23 mmol, 1.1 eq.) and Pyridine (49.0 μl, 0.61 mmol, 3 eq) were added in methylene chloride. The mixture was stirred for 5 hrs at room temperature. The reaction mixture was quenched by adding sat. NaHCO$_3$ solution. The reaction mixture was extracted with methylene chloride. A combined organic layer was washed with 5% HCl, sat. NaHCO$_3$ solution, and H$_2$O, dried over Na$_2$SO$_4$, and concentrated in vacuo. The residue was purified with column chromatography to yield title product (50.4 mg, 79.6%) as a solid.

[α]$^{23}_D$: +42.88° (c 0.41, CHCl$_3$); IR (KBr pellet): 3410, 2972, 2929, 2152, 1678 cm$^{-1}$ $^1$H NMR (400 MHz, CDCl$_3$): δ 7.53 (d, 1H, J=8.4 Hz), 7.40 (d. 1H, J=2.0 Hz), 7.28 (dd, 1H, J=8.4, 2.0 Hz), 6.94 (bs, 1H), 4.83 (d, 2H, J=7.6 Hz), 4.72 (bs, 1H), 2.99 (s, 3H), 1.42-1.40 (m, 12H), 0.29 (s, 9H).

Step 3: (R)—N-(4-{1-[3-(4-tert-Butylphenyl)ureido]ethyl}-2-trimethylsilanylethynylphenyl)methanesulfonamide

[1-(4-Methanesulfonylamino-3-trimethylsilanylethynyl-phenyl)-ethyl]-carbamic acid tert-butyl ester (300 mg, 0.724 mmol, 1 eq) was added in methylene chloride. Trifluoroacetic acid (279 µl, 3.619 mmol, 3 eq.) was added into mixture. The reaction mixture was stirred for 24 hrs. The mixture was concentrated in vacuo to title compound (440.1 mg) as a liquid.

(R)—N-[4-(1-Amino-ethyl)-2-trimethylsilanylethynylphenyl]methanesulfonamide (75.0 mg, 0.242 mmol, 1 eq.) and Triethylamine (67.5 µl, 0.484 mmol, 2 eq.) were dissolved in methylene chloride. The mixture was cooled down to 0° C. 4-tert-Butylphenyl isocyanate (47.2 µl, 0.266 mmol, 1.1 eq.) was added into the reaction mixture. The reaction mixture was stirred for 40 min. A reaction solvent was removed in vacuo. The residue was purified with column chromatography (n-Hx:EA=2:1) to yield title compound (45.3 mg, 39%) as a solid.

mp: 118.5-119.5° C.; $[\alpha]^{23}_D$ −24.79° (c 0.63, CHCl$_3$), IR (KBr pellet, cm$^{-1}$): 3406, 2962, 2928, 2868, 2150, 1649; $^1$H NMR (400 MHz, CDCl$_3$): 7.43 (d, 1H, J=8.4 Hz), 7.35 (d, 1H, J=2.0 Hz), 7.24 (d, 2H, J=8.8 Hz), 7.21 (dd, 1H, J=8.4, 2.0 Hz), 7.09 (d, 2H, J=8.8 Hz), 6.86 (bs, 1H), 6.40 (bs, 1H), 4.86 (q, 1H, J=6.8 Hz), 2.91 (s, 9H), 1.34 (q, 1H, J=6.8 Hz), 1.22 (s, 9H), 0.21 (s, 9H)

Example 55

(R)—N-(4-{1-[3-(4-tert-Butylphenyl)ureido]ethyl}-2-ethynylphenyl)methanesulfonamide

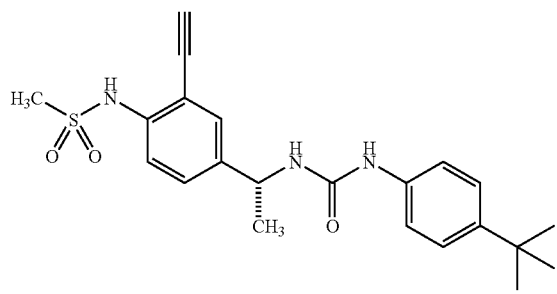

(R)—N-(4-{1-[3-(4-tert-Butyl-phenyl)ureido]ethyl}-2-trimethylsilanylethynyl-phenyl)methanesulfonamide (11 mg, 0.023 mmol) was dissolved in THF. The reaction mixture was cooled down to 0° C. 1.0 M solution of tetrabutylammoniumfluoride in THF (0.068 ml, 0.068 mmol, 3 eq.) was added into the reaction mixture. The reaction mixture was stirred for 1.5 hrs. The reaction mixture was concentrated in vacuo and purified with column chromatography (n-Hx:EA=1:1) to yield title compound (7.0 mg, 74%) as a solid.

mp: 88.4-89.4° C.; $[\alpha]^{23}_D$ −28.19° (c 0.31, CHCl$_3$);

IR (KBr pellet, cm$^{-1}$): 3410, 2961, 2926, 2855, 2104, 1645;

$^1$H NMR (400 MHz, CDCl$_3$): 7.49 (d, 1H, J=8.4 Hz), 7.39 (d, 1H, J=1.6 Hz), 7.26 (d, 3H, J=8.8 Hz), 7.10 (d, 2H, J=8.8 Hz), 6.89 (bs, 1H), 6.22 (bs, 1H), 4.96 (bs, 1H), 4.89 (q, 1H, J=6.8 Hz), 3.40 (s, 1H), 2.94 (s, 3H), 1.36 (d, 3H, J=6.8 Hz), 1.23 (s, 9H).

Example 56

N-(4-{1-[3-(4-tert-Butylphenyl)ureido]methyl}-2-vinylphenyl)methanesulfonamide

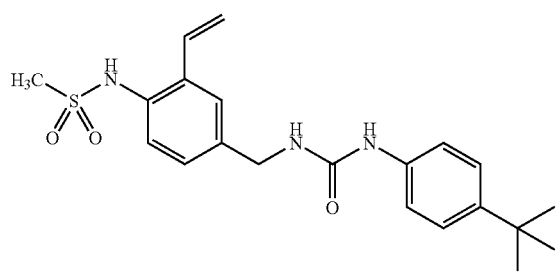

N-[4-(1-Amino-ethyl)-2-vinyl-phenyl]-methanesulfonamide (236.7 mg, 0.985 mmol) and triethylamine (274.6 µl, 1.970 mmol, 2 eq) were added in methylene chloride. The reaction mixture was cooled down to 0° C. 4-tert-Butylphenyl isocyanate (192.5 µl, 1.083 mmol, 1.3 eq.) was added into the mixture. The reaction mixture was stirred for 40 min. A reaction solvent was removed in vacuo. The residue was purified with column chromatography (n-Hx:EA=2:1) to yield title compound (155.4 mg, 47%) as a white solid.

$^1$H NMR (400 MHz, CDCl$_3$): 8.02 (d, 2H, J=8.8 Hz), 7.30 (d, 2H, J=8.8 Hz), 7.03 (d, 2H, J=8.4 Hz), 6.99 (d, 2H, J=8.4 Hz), 5.51 (bs, 1H), 4.90 (q, 1H, J=6.8 Hz), 2.44 (t, 2H, J=7.2 Hz), 1.50 (sextet, 2H, J=7.2 Hz), 1.26 (d, 3H, J=6.8 Hz), 0.84 (t, 3H, J=7.2 Hz)

Example 57

N-{4-[3-(4-tert-Butylphenyl)ureidomethyl]-2-fluoro-6-vinylphenyl}methanesulfonamide

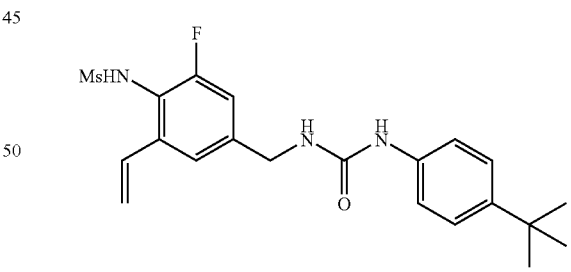

N-(4-Aminomethyl-2-fluoro-6-vinylphenyl)methanesulfonamide (37.8 mg, 0.11 mmol), 1-tert-butyl-4-isocyanatobenzene (1.2 eq, 0.13 mmol, 22.49 µl), and TEA (3 eq, 0.33 mmol, 45.99 µl) were added in methylene chloride. The reaction mixture was stirred for 12 hrs. The reaction mixture was extracted with methylene chloride. A combined organic layer was washed with H$_2$O and brine, dried over Na$_2$SO$_4$, and concentrated in vacuo. The residue was purified with column chromatography (n-Hx:EA=1:1) to yield title compound (26.1 mg, 55%) as a white solid.

Mp: 167~170° C.;

IR (KBr pellet, cm$^{-1}$): 3328, 3246, 3072, 2961, 1320, 1152;
$^1$H NMR (400 MHz, CD$_3$OD): δ 7.44 (s, 1H), 7.26 (d, 2H, J=8.0 Hz), 7.23 (d, 2H, J=8.0 Hz), 7.16 (dd, 1H, J=17.6, 11.2 Hz), 7.09 (dd, 1H, J=10.4, 1.6 Hz), 6.89 (s, 1H), 5.82 (d, 1H, J=17.6 Hz), 5.35 (d, 1H, J=11.2 Hz), 4.35 (s, 2H), 2.99 (s, 3H), 1.37 (s, 9H).

Example 58

Ethenesulfonic Acid (4-{1-[3-(4-tert-butylphenyl)ureido]ethyl}-2-vinylphenyl)amide

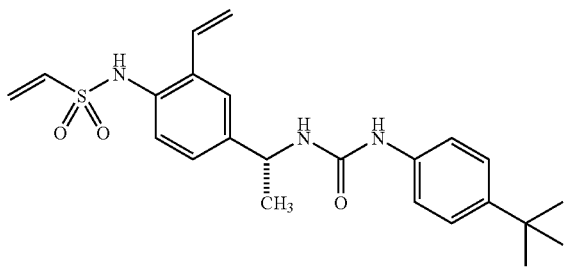

Step 1: Ethenesulfonic acid (4-{1-[1-(2,2-dimethylpropyl)vinylamino]ethyl}-2-iodophenyl)amide 4-{1-[1-(2,2-Dimethylpropyl)vinylamino]ethyl}-2-iodophenylamine (218.1 mg, 0.65 mmol) was dissolved in methylene chloride. The reaction mixture was cooled down to 0° C. 2-Chloroethane sulfonyl chloride (3 eq, 1.95 mmol, 203.64 μl) and Pyridine (3 eq, 1.95 mmol, 157.71 μl) were added into mixture. The reaction mixture was stirred for 48 hrs. After confirming the completion of the synthesis, a reaction solvent was removed in vacuo. A residue was extracted with methylene chloride. A combined organic layer was washed with H$_2$O and brine, dried over NaSO$_4$, and concentrated in vacuo. The residue was purified with column chromatography (n-Hx:EA=3:1) to yield title compound (104.9 mg, 78%) as a brownish solid.

mp: 112~114° C.;
$[α]_D^{20}$ +31.69 (CHCl$_3$, c 1.74);
IR (KBr pellet, cm$^{-1}$): 3323, 2976, 1693, 736; $^1$H NMR (400 MHz, CDCl$_3$): δ7.66 (s, 1H), 7.47 (dd, 1H, J=8.4, 8.0 Hz), 7.22 (d, 1H, J=8.4 Hz), 6.59 (s, 1H), 6.54 (qd, 1H, J=16.8, 10.0, 1.2 Hz), 6.20 (d, 1H, J=16.4 Hz), 5.91 (d, H, J=10.0 Hz), 4.77 (bs, 1H), 4.65 (bs, 1H), 1.36 (s, 12H)

Step 2: [1-(4-Ethenesulfonylamino-3-vinylphenyl)ethyl]carbamic acid tert-butyl ester

[1-(4-Ethenesulfonylamino-3-iodophenyl)ethyl]carbamic acid tert-butyl ester (58.4 mg, 0.13 mmol), Pd(PPh$_3$)$_4$ (0.06 eq, 0.0078 mmol, 9.10 mg), LiCl (2.8 eq, 0.19 mmol, 15.43 mg), and TEA (1.5 eq, 0.19 mmol, 56.99 μl) were added in DMF. The reaction mixture was stirred for 12 hrs at 90° C. DMF was removed in vacuo. The residue was extracted with ethyl acetate. A combined organic layer was washed with H$_2$O and brine, dried over Na$_2$SO$_4$, and concentrated in vacuo. The residue was purified with column chromatography (N-Hx:EA=3:1) to yield title compound (24.8 mg, 18%) as brown liquid.

mp: 80~82° C.;
$[α]_D^{20}$: +6.21 (CHCl$_3$, c 0.47);
IR (NaCl neat, cm$^{-1}$): 3347, 2958, 1686; $^1$H NMR (400 MHz, CDCl$_3$): 7.30 (t, 1H, J=1.2 Hz), 7.28 (s, 1H), 7.12 (dd, 1H, J=8.0, 1.2 Hz) 6.80 (q, 1H, J=6.4, 10.8 Hz), 6.50 (dq, 1H, J=10.8, 6.4, 0.8 Hz), 6.41 (s, 1H), 5.86 (d, 1H, J=10.0 Hz), 5.62 (d, 1H, J=17.6 Hz), 5.37 (d, 1H, J=11.2 Hz), 4.75 (s, 1H), 4.68 (s, 1H).

Step 3: Ethenesulfonic acid (4-{1-[3-(4-tert-butylphenyl)ureido]ethyl}-2-vinylphenyl)amide

[1-(4-Ethenesulfonylamino-3-vinyl-phenyl)-ethyl]-carbamic acid tert-butyl ester (20.0 mg, 0.04 mmol) and CF$_3$COOH (5 eq, 0.22 mmol, 17.04 μl) were dissolved in methylene chloride. The reaction mixture was stirred for 12 hrs. A reaction mixture was concentrate to yield [1-(4-Ethenesulfonylamino-3-vinyl-phenyl)-ethylamine (15.6 mg, 76%).

Ethenesulfonic acid [4-(1-amino-ethyl)-2-vinyl-phenyl]-amide (15.6 mg, 0.04 mmol), 4-tert-butyl phenylisocyanate (1.2 eq, 0.053 mmol, 9.45 μl), and TEA (1.2 eq, 0.12 mmol, 16.73 μl) were added in MC. The reaction mixture was stirred for 5 hrs. The reaction mixture was extracted with methylene chloride. A combined organic layer was washed with H$_2$O and brine, dried over Na$_2$SO$_4$, and concentrated in vacuo. The residue was purified with column chromatography (n-Hx:EA=3:1->2:1) to yield title compound (34.2 mg, 40%).

mp: 60~62° C.;
$[α]_D^{20}$ −17.57 (CHCl$_3$, c0.28);
IR (NaCl neat, cm$^{-1}$): 3346, 3189, 2962, 1649, 1318;
$^1$H NMR (400 MHz, CD$_3$OD): 7.59 (d, 1H, J=1.6 Hz), 7.27 (t, 1H, J=2.4 Hz), 7.26 (s, 1H), 7.25 (s, 2H), 7.23 (s, 2H), 7.10 (q, 1H, J=11.2, 6.4 Hz), 6.69 (q, 1H, J=6.8, 9.6 Hz), 6.02 (d, 1H, J=16.4 Hz), 5.90 (d, 1H, J=10.0 Hz), 5.77 (dd, 1H, J=1.2, 17.6 Hz), 5.33 (dd, 1H, J=1.2, 10.8 Hz), 1.45 (d, 3H, J=6.8 Hz), 1.27 (s, 9H).

Example 59

N-(4-{1-[3-(4-tert-Butylphenyl)ureido]ethyl}-2-phenylethynylphenyl)methanesulfonamide

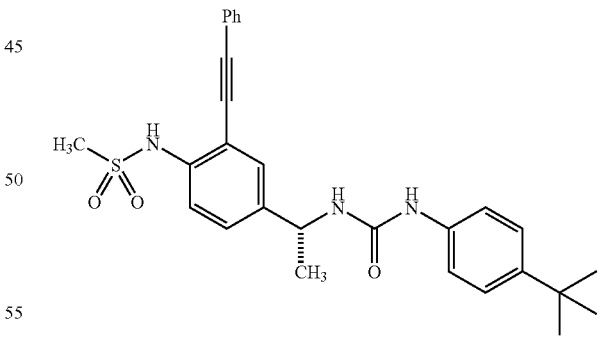

Step 1:
[1-(4-Amino-3-phenylethynylphenyl)ethyl]carbamic acid tert-butyl ester

[1-(4-Amino-3-iodophenyl)ethyl]carbamic acid tert-butyl ester (500 mg, 1.380 mmol, 1 eq.), dichloro(bistriphenylphosphine) palladium (48.4 mg, 0.069 mmol, 0.05 eq.) and copper iodide 13.1 mg (0.069 mmol, 0.05 eq.) were added in THF. After stirring for 30 min at room temperature, TEA (577.0 μl, 4.140 mmol, 3 eq) and phenylacetylene (197.0 μl, 1.794 mmol, 1.3 eq) were added into the reaction mixture. The reaction mixture was stirred overnight with reflux. A reaction solvent was removed in vacuo. The residue was purified with column chromatography (n-Hx:EA=5:1) to yield title compound (452.7 mg) as a yellow liquid.

$[\alpha]^{23}_D$ −4.80° (c 0.83, CHCl$_3$);

IR (NaCl neat, cm$^{-1}$): 3433, 2968, 2922, 2852, 2198, 1684;

$^1$H NMR (400 MHz, CDCl$_3$): 7.44-7.40 (m, 2H), 7.26 (−7.16 (m, 4H), 6.97 (dd, 1H, J=8.0, 1.2 Hz), 6.56 (d, 1H, J=8.0 Hz), 4.76 (d, 1H, J=7.6 Hz), 4.58 (bs, 1H), 1.33 (s, 9H), 1.31 (d, 3H, J=7.2 Hz).

Step 2: [1-(4-Methanesulfonylamino-3-phenylethynylphenyl)ethyl]carbamic acid tert-butyl ester

[1-(4-Amino-3-phenylethynylphenyl)ethyl]carbamic acid tert-butyl ester (487.1 mg, 1.448 mmol, 1 eq.) and methansulfonic anhydride (302.7 mg, 0.737 mmol, 1.2 eq.) were added in methylene chloride. The reaction mixture was cooled down to 0° C. Pyridine (348.1 μl, 4.344 mmol, 3 eq.) was added into the reaction mixture. The reaction mixture was stirred for 1 hr. The reaction was quenched by adding sat. NaHCO$_3$ solution. The reaction mixture was extracted with methylene chloride. A combined organic layer was washed with 5% HCl, sat. NaHCO$_3$ solution., H$_2$O, and then brine; dried over Na$_2$SO$_4$; then concentrated in vacuo. The residue was purified with column chromatography (n-Hx:EA=5:1) to yield title compound (300 mg, 83%).

mp: 157-158° C.;

$[\alpha]^{23}_D$ +45.52° (c 0.31, CHCl$_3$);

IR (KBr pellet, cm$^{-1}$): 3362, 3253, 3013, 2974, 2930, 1684; $^1$H NMR (400 MHz, CDCl$_3$) 7.51 (d, 1H, J=8.4 Hz), 7.48-7.45 (m, 2H), 7.42 (d. 1H, J=2.0 Hz), 7.35-7.31 (m, 3H), 7.24 (dd, 1H, J=8.4, 2.0 Hz), 6.91 (s, 1H), 4.72 (bs, 2H), 2.97 (s, 3H), 1.39-1.36 (m, 12H).

Step 3: N-(4-{1-[3-(4-tert-Butylphenyl)ureido]ethyl}-2-phenylethynylphenyl)methanesulfonamide

[1-(4-Methanesulfonylamino-3-phenylethynylphenyl)ethyl]carbamic acid tert-butyl ester (300 mg, 0.724 mmol) and trifluoroacetic acid (279 μl, 3.619 mmol, 3 eq) were added in methylene chloride. The reaction mixture was stirred for 24 hrs. A reaction solvent was removed in vacuo to yield 1-(4-methanesulfonylamino-3-phenylethynylphenyl)ethylamine (440.1 mg, 100%).

N-[4-(1-Aminoethyl)-2-phenylethynylphenyl]methanesulfonamide (440.1 mg, 1.40 mmol) and TEA (390.3 μl, 2.800 mmol, 2 eq) were added in methylene chloride. The reaction mixture was cooled down to 0° C. 4-tert-Butylphenyl isocyanate (248.8%, 1.540 mmol, 1.3 eq.) was added into the mixture. The reaction mixture was stirred for 1 hr. Methylene chloride was removed in vacuo. The residue was purified with column chromatography (n-Hx:EA=2:1) to yield title compound (241.4 mg, 35%) as a solid.

$^1$H NMR (400 MHz, CDCl$_3$): 8.02 (d, 2H, J=8.8 Hz), 7.30 (d, 2H, J=8.8 Hz), 7.03 (d, 2H, J=8.4 Hz), 6.99 (d, 2H, J=8.4 Hz), 5.51 (bs, 1H), 4.90 (q, 1H, J=6.8 Hz), 2.44 (t, 2H, J=7.2 Hz), 1.50 (sextet, 2H, J=7.2 Hz), 1.26 (d, 3H, J=6.8 Hz), 0.84 (t, 3H, J=7.2 Hz);

mp: 103-104° C.;

$[\alpha]^{23}_D$ −38.55° (c 0.33, CHCl$_3$);

IR (KBr pellet): 3375, 3056, 2962, 2903, 2260 cm$^{-1}$

Example 60

N-(4-{1-[3-(4-tert-Butylphenyl)ureido]ethyl}-2-styrylphenyl)methanesulfonamide

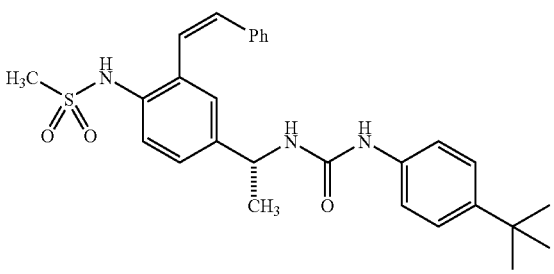

N-(4-{1-[3-(4-tert-Butyl-phenyl)-ureido]-ethyl}-2-phenylethynylphenyl)-methanesulfonamide (50 mg, 0.102 mmol, 1 eq.) and palladium on calcium carbonate, poisoned with lead (Lindlar catalyst) were added in methanol. The reaction mixture stirred 12 hrs under H$_2$ atmosphere. The reaction mixture was filtered with celite pad. The filterate was concentrated in vacuo. The residue was purified with column chromatography (n-Hx:EA=2:1) to yield title compound (16 mg, 32%).

$[\alpha]^{23}_D$ −8.80° (c 0.5, CHCl$_3$);

IR (KBr pellet, cm$^{-1}$): 3407, 3025, 2962, 2927, 1648, 1543;

$^1$H NMR (400 MHz, CDCl$_3$): 7.39 (d, 1H, J=8.4 Hz), 7.25-7.00 (m, 11H), 6.72 (d, 1H, J=12.4 Hz), 6.44 (d, 1H, J=12.4 Hz), 6.38 (bs, 1H), 4.83 (q, 1H, J=6.8 Hz), 2.60 (s, 3H), 1.29 (d, 3H, J=6.8 Hz), 1.22 (s, 9H).

Experimental Example

Biological Potency Test

1. $^{45}$Ca Influx Test

1) Separation of Spinal Dorsal Root Ganglia (DRG) in Newborn Rats and Primary Culture Thereof Neonatal (2-3 day old or younger than 2-3 day old) SD rats were put in ice for 5 minutes to anesthetize and disinfected with 70% ethanol. DRG of all part of spinal cord were dissected (Wood et al., 1988, J. Neurosci. 8, pp 3208-3220) and collected in DME/F12 medium to which 1.2 g/l sodium bicarbonate, 50 mg/l gentamycin were added. The DRG were incubated sequentially at 37° C. for 30 min in 200 U/ml collagenase and 2.5 mg/ml trypsin, separately. The ganglia were washed twice with DME/F12 medium supplemented with 10% horse serum, triturated through a fire-polished Pasteur pipette, filtered through Nitex 80 membrane to obtain single cell suspension and the suspension was washed once more. This was subjected to centrifugation, then resuspended in cell culture medium at certain level of cell density. As the cell culture medium, DME/F12 medium supplemented with 10% horse serum was diluted with identical medium conditioned by C6 glioma cells 2 days on a confluent monolayer (1:1), and NGF (Nerve Growth Factor) was added to adjust 200 ng/ml as final concentration. After the cells were grown 2 days in medium where cytosine arabinoside (Ara-C, 100 μM) was added to kill dividing nonneuronal cells, medium was changed to one without Ara-C. The resuspended cells were plated at a density of 1500-2000 neurons/well onto Terasaki plates previously coated with 10 µg/ml poly-D-ornithine.

2) $^{45}$Ca Influx Experiments

DRG nerve cells from the primary culture of 2 days were equilibrated by washing 4 times with HEPES (10 mM, pH 7.4)-buffered $Ca^{2+}$, $Mg^{2+}$-free HBSS (H—HBSS). The solution in each well was removed from the individual well. Medium containing the test compound plus capsaicin (final concentration 0.5 µM) and $^{45}$Ca (final concentration 10 µCi/ml) in H—HBSS was added to each well and incubated at room temperature for 10 mins. Terasaki plates were washed five times with H—HBSS and dried at room temperature. To each well, 0.3% SDS (10 µl) was added to elute $^{45}$Ca. After the addition of scintillation cocktail of into each well, the amount of $^{45}$Ca influx into neuron was measured by counting radioactivity. Antagonistic activities of test compounds against vanilloid receptor were calculated as percent of the inhibition of maximal response of capsaicin at a concentration of 0.5 µM. In summary, all examples of the present invention showed good to excellent IC50 values between 20 and 500 nM, with most of the compounds having a IC50 values below 200 nM.

TABLE 2

Results of Calcium Influx Test

| Examples | Antagonist Calcium Uptake Test (IC$_{50}$, µM) |
|---|---|
| 1 | 0.16 |
| 2 | 0.098 |
| 3 | 0.18 |
| 4 | 0.17 |
| 5 | 0.49 |
| 6 | 0.082 |
| 7 | 0.039 |
| 8 | 0.31 |
| 9 | 0.13 |
| 11 | 0.079 |
| 12 | 0.087 |
| 13 | 0.15 |
| 14 | 0.05 |
| 15 | 0.034 |
| 16 | 0.047 |
| 17 | 0.058 |
| 21 | 0.16 |
| 22 | 0.25 |
| 23 | 0.067 |
| 27 | 0.076 |
| 28 | 0.073 |
| 30 | 0.068 |
| 32 | 0.49 |
| 34 | 0.17 |
| 35 | 0.033 |
| 36 | 0.054 |
| 37 | 0.049 |
| 38 | 0.27 |
| 40 | 0.29 |
| 41 | 0.043 |
| 42 | 0.022 |
| 43 | 0.067 |
| 45 | 0.063 |
| 46 | 0.025 |
| 47 | 0.17 |
| 53 | 0.099 |
| 55 | 0.17 |
| 57 | 0.5 |
| 58 | 0.45 |

3. Analgesic Activity Test: Mouse Writhing Test by Inducing with phenyl-p-quinone Male ICR mice (mean body weight 25 g) were maintained in a controlled lighting environment (12 h on/12 h off) for experiment. Animals received an intraperitoneal injection of 0.3 ml of the chemical irritant phenyl-p-quinone (dissolved in saline containing 5% ethanol to be a dose of 4.5 mg/kg) and 6 mins later, the number of abdominal constrictions was counted in the subsequent 6 mins period. Animals (10 animals/group) received 0.2 ml of test compounds solution in vehicle of ethanol/Tween 80/saline (10/10/80) intraperitoneally 30 min before the injection of phenyl-p-quinone. A reduction in the number of writhes responding to the test drug compound relative to the number responding in saline control group was considered to be indicative of an analgesic effect. Analgesic effect was calculated by % inhibition equation (% inhibition=(C−T)/C×100), wherein C and T represent the number of writhes in control and compound-treated group, respectively (Table 3).

TABLE 3

Test result of analgesic activity for writhing by phenyl-p-quinone

| Example | Dose (mg/kg) | Analgesic effect (% Inhibition) |
|---|---|---|
| 2 | 0.3 | 57% |
| 6 | 1 | 56% |
| 14 | 1 | 58% |
| 15 | 1 | 60% |
| 16 | 1 | 68% |
| 17 | 1 | 63% |
| 25 | 1 | 64% |
| 41 | 1 | 44% |
| 45 | 1 | 82% |
| 46 | 1 | 43% |

INDUSTRIAL APPLICABILITY

As explained above, the compound according to the present invention is useful to preventing and treating of pain, migraine, arthralgia, neuralgia, neuropathies, nerve injury, skin disorder, urinary bladder hypersensitiveness, irritable bowel syndrome, fecal urgency, a respiratory disorder, irritation of skin, eye or mucous membrane, stomach-duodenal ulcer, inflammatory diseases, ear disease, and heart disease etc.

More specifically, the compound according to the present invention is useful to preventing and treating of acute pain, chronic pain, neuropathic pain, post-operative pain, rheumatic arthrodynia, osteoarthritis pain, postherpetic neuralgia, diabetic neuropathy, HIV-related neuropathy, neurodegeneration, stroke, neurotic/allergic/inflammatory skin disease, psoriasis, pruritus, prurigo, asthma, chronic obstructive pulmonary disease, urinary incontinence, inflammatory bowel disease, hyperacusis, tinnitus, vestibular hypersensitiveness, and inotropic ischemia.

The invention claimed is:

1. A compound of formula (I) or pharmaceutically acceptable salt thereof:

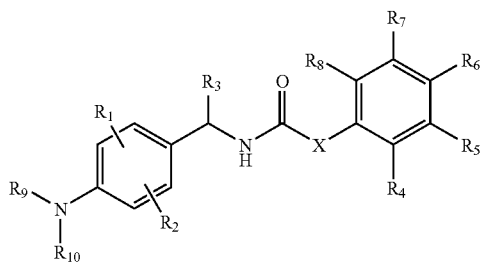

wherein,

X is NHCH$_2$, CR$_{11}$=CR$_{12}$, NH, CHR$_{11}$CHR$_{12}$, or C≡C, wherein R$_{11}$ and R$_{12}$ are independently hydrogen, halogen, C1-C5 alkyl, C1-C5 alkoxy, halo (C1-C5) alkyl, or phenyl;

R$_1$ is C2-C5 alkenyl or C2-C5 alkynyl;

R$_2$ is hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl;

R$_3$ is hydrogen, C1-C5 alkyl, C1-C5 alkoxy, or halo (C1-C5) alkyl;

R$_4$, R$_5$, R$_6$, R$_7$, and R$_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkylcarbonyl, C1-C5 alkoxycarbonyl, hydroxy, C2-C5 alkenyloxy, C1-C5 alkoxy (C1-C5) alkoxy, C1-C5 alkoxy (C1-C5) alkoxy (C1-C5) alkyl, C1-C3 alkylpiperazinyl, piperazinyl (C1-C5) alkoxy, piperidinyl (C1-C5) alkoxy, C1-C5 alkoxy (C1-C5) alkylamino, C1-C7 alkylamino, morpholinyl, morpholinyl (C1-C5) alkyloxy, tetrahydropyranyloxy, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, C1-C5 alkoxycarbonyl, or piperidinyloxy unsubstituted or substituted with C1-C5 alkoxycarbonyl; and R$_9$ and R$_{10}$ are independently hydrogen, —SO$_2$R$_{13}$, —SOR$_{13}$, C1-C5 alkyl, C1-C5 alkoxy, halo (C1-C5) alkyl, C2-C5 alkenyl, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl, and R$_{13}$ is hydrogen, amino, C1-C5 alkyl, C2-C5 alkenyl, C1-C5 alkoxy, halo (C1-C5) alkyl, trifluoromethyl, phenyl, or phenyl (C1-C3) alkyl.

2. A compound according to claim 1 or pharmaceutically acceptable salt thereof,
wherein, X is NHCH$_2$, CR$_{11}$=CR$_{12}$, or C≡C, wherein, R$_{11}$ and R$_{12}$ are independently hydrogen, halogen, C1-C5 alkyl, or phenyl;

R$_1$ is C2-C5 alkenyl or C2-C5 alkynyl;

R$_2$ is hydrogen, halogen, nitro, cyano, C1-C5 alkyl, C1-C5 alkoxy, halo (C1-C5) alkyl, C2-C5 alkenyl, C2-C5 alkynyl, carboxy, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl;

R$_3$ is hydrogen, C1-C5 alkyl, C1-C5 alkoxy, or halo (C1-C5) alkyl;

R$_4$, R$_5$, R$_6$, R$_7$, and R$_8$ are independently hydrogen, carboxy, C1-C5 alkyl, nitro, C2-C5 alkenyl, C1-C5 alkoxy, C2-C5 alkynyl, halo (C1-C5) alkyl, C1-C5 alkylthio, C1-C5 alkylsulfonyl, C1-C5 alkylcarbonyl, C1-C5 alkoxycarbonyl, phenyl, or halogen, wherein, phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl; and R$_9$ and R$_{10}$ are independently hydrogen, —SO$_2$R$_{13}$, —SOR$_{13}$, C1-C5 alkyl, C1-C5 alkoxy, halo (C1-C5) alkyl, C2-C5 alkenyl, C1-C5 alkoxycarbonyl, C1-C5 alkylthio, phenyl, or phenyl (C1-C3) alkyl, wherein, each phenyl may be unsubstituted or substituted with one or more substituent selected from carboxy, C1-C5 alkyl, halogen, nitro, C2-C5 alkenyl, C1-C5 alkoxy, halo (C1-C5) alkyl, C1-C5 alkylcarbonyl, C1-C5 alkylthio, C1-C5 alkylsulfonyl, and C1-C5 alkoxycarbonyl, and R$_{13}$ is hydrogen, amino, C1-C5 alkyl, C2-C5 alkenyl, C1-C5 alkoxy, halo (C1-C5) alkyl, trifluoromethyl, phenyl, or phenyl (C1-C3) alkyl.

3. A compound according to claim 1 or pharmaceutically acceptable salt thereof;
wherein, X is NHCH$_2$, CR$_{11}$=CR$_{12}$, or C≡C, wherein, R$_{11}$ and R$_{12}$ are independently hydrogen, halogen, C1-C5 alkyl, or phenyl;

R$_1$ is ethenyl, ethynyl, propenyl, or propynyl;

R$_2$ is hydrogen, fluoro, chloro, bromo, iodo, nitro, cyano, methyl, ethyl, propyl, isopropyl, butyl, isobutyl, methoxy, ethoxy, trifluoromethyl, carboxy, methoxycarbonyl, or phenyl;

R$_3$ is hydrogen, methyl, or ethyl;

R$_4$, R$_5$, R$_6$, R$_7$, and R$_8$ are independently hydrogen, carboxy, methyl, ethyl, propyl, isopropyl, t-butyl, nitro, ethenyl, ethynyl, methylthio, trifluoromethyl, methoxycarbonyl, or halogen; and R$_9$ and R$_{10}$ are independently hydrogen, —SO$_2$R$_{13}$, —SOR$_{13}$, C1-C5 alkyl, C1-C5 alkoxy, halo (C1-C5) alkyl, C2-C5 alkenyl, phenyl, phenyl (C1-C3) alkyl, or C1-C3 alkoxyphenyl, wherein, R$_{13}$ is hydrogen, amino, C1-C5 alkyl, C2-C5 alkenyl, trifluoromethyl, phenyl, or benzyl.

4. A compound according to claim 1 or pharmaceutically acceptable salt thereof, wherein, X is NHCH$_2$, CH$_2$=CH$_2$, or C≡C;

R$_1$ is ethenyl or ethynyl;

$R_2$ is hydrogen, fluoro, chloro, bromo, iodo, nitro, cyano, methyl, ethyl, propyl, isopropyl, butyl, isobutyl, methoxy, ethoxy, trifluoromethyl, carboxy, methoxycarbonyl, or phenyl;

$R_3$ is hydrogen, methyl, or ethyl;

$R_4$, $R_5$, $R_7$, $R_8$, and $R_{10}$ are hydrogen;

$R_6$ is isopropyl or t-butyl; and $R_9$ is methanesulfonyl, ethanesulfonyl, trifluoromethanesulfonyl, or ethenesulfonyl.

5. A compound according to claim 1 or pharmaceutically acceptable salt thereof, wherein the compound is a compound of formula (Ia),

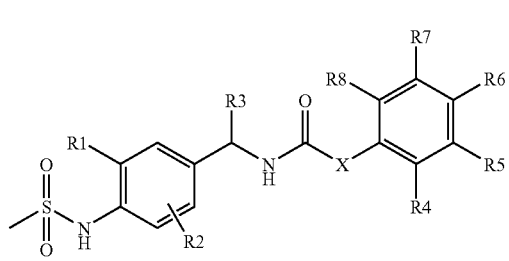

(Ia)

and wherein

X is $NHCH_2$ or $CH_2=CH_2$;

$R_1$ is ethenyl or ethynyl;

$R_2$ is hydrogen, fluoro, chloro, bromo, iodo, nitro, cyano, methyl, ethyl, propyl, isopropyl, butyl, isobutyl, methoxy, ethoxy, trifluoromethyl, carboxy, methoxycarbonyl, or phenyl;

$R_3$ is hydrogen, methyl, or ethyl;

$R_4$, $R_5$, $R_7$, and $R_8$ are hydrogen; and $R_6$ is isopropyl or t-butyl.

6. A compound according to claim 1 or pharmaceutically acceptable salt thereof wherein, X is $NHCH_2$, $CR_{11}=CR_{12}$, NH, $CHR_{11}CHR_{12}$ or $C\equiv C$, wherein, $R_{11}$ and $R_{12}$ are independently hydrogen, fluoro or methyl;

$R_1$ is ethenyl, ethynyl, propenyl, or propynyl;

$R_2$ is hydrogen, fluoro, chloro, bromo, iodo, nitro, cyano, methyl, ethyl, propyl, isopropyl, butyl, isobutyl, methoxy, ethoxy, ethynyl, ethenyl, carboxy, or methoxycarbonyl;

$R_3$ is hydrogen, methyl, or ethyl;

$R_4$, $R_5$, $R_7$, and $R_8$ are independently hydrogen, fluoro, carboxy, methyl, ethyl, propyl, isopropyl, t-butyl, nitro, ethenyl, ethynyl, trifluoromethyl, methoxycarbonyl, halogen, methoxymethoxy, methoxyethoxy, methoxyethoxymethyl, methylpiperazinyl, methoxyethylamino, hydroxy, methoxy, allyloxy, isohexylamino, isobutylammino, isopropylamino, morpholinyl, morpholinylethoxy, or tetrahydropyranyloxy;

$R_6$ is C3-C5 alkyl or halo (C1-C3) alkyl; and $R_9$ and $R_{10}$ are independently hydrogen or methanesulfonyl.

7. A compound according to claim 1 or pharmaceutically acceptable salt thereof wherein, X is $NHCH_2$, $CR_{11}=CR_{12}$, $CHR_{11}CHR_{12}$ or $C\equiv C$, wherein, $R_{11}$ is hydrogen or methyl and $R_{12}$ is hydrogen;

$R_1$ is ethenyl or ethynyl;

$R_2$ is hydrogen, fluoro, methyl, or chloro;

$R_3$ is hydrogen or methyl;

$R_4$, is hydrogen, fluoro, methoxymethoxy, methoxyethoxy, methoxypropoxy, methoxy, methoxyethylamino, allyloxy, or tetrahydropyranyloxy;

$R_5$, $R_7$ and $R_8$ are hydrogen or fluoro;

$R_6$ is isopropyl or t-butyl; and $R_9$ is hydrogen and $R_{10}$ represents methanesulfonyl.

8. A compound according to claim 1 or pharmaceutically acceptable salt thereof, wherein X is $CHR_{11}-CHR_{12}$.

9. A compound according to claim 8 or pharmaceutically acceptable salt thereof, wherein, X is $CHR_{11}-CHR_{12}$;

$R_{11}$ and $R_{12}$ are methyl or hydrogen;

$R_1$ is ethenyl or ethynyl;

$R_2$ is hydrogen, fluoro, chloro, bromo, iodo, nitro, cyano, methyl, ethyl, propyl, isopropyl, butyl, isobutyl, methoxy, ethoxy, trifluoromethyl, carboxy, or methoxycarbonyl;

$R_3$ is hydrogen, methyl, or ethyl;

$R_4$, $R_5$, $R_7$, and $R_8$ are independently hydrogen, fluoro, carboxy, methyl, ethyl, propyl, isopropyl, t-butyl, nitro, ethenyl, ethynyl, trifluoromethyl, methoxycarbonyl, halogen, methoxymethoxy, methoxyethoxy, methoxypropoxy, methoxyethoxymethyl, methylpiperazinyl, methoxyethylamino, hydroxy, methoxy, allyloxy, isohexylamino, isobutylammino, isopropylamino, morpholinyl, morpholinylethoxy, or tetrahydropyranyloxy; and $R_6$ is isopropyl, t-butyl, or halo (C1-C3)alkyl.

10. A compound according to claim 8 or pharmaceutically acceptable salt thereof, wherein $R_{11}$ is hydrogen or methyl, and $R_{12}$ is hydrogen;

$R_1$ is ethenyl or ethynyl;

$R_2$ is hydrogen, fluoro, chloro, or methyl;

$R_4$ is hydrogen, fluoro, methoxymethoxy, methoxyethoxy, methoxypropoxy, methoxy, methoxyethylamino, allyloxy, or tetrahydropyranyloxy;

$R_5$, $R_7$ and $R_8$ are hydrogen or fluoro;

$R_6$ is tert-butyl; $R_9$ is hydrogen; and $R_{10}$ represents methanesulfonyl.

11. A compound according to claim 1 or pharmaceutically acceptable salt thereof, wherein the compound is a compound of formula (Id),

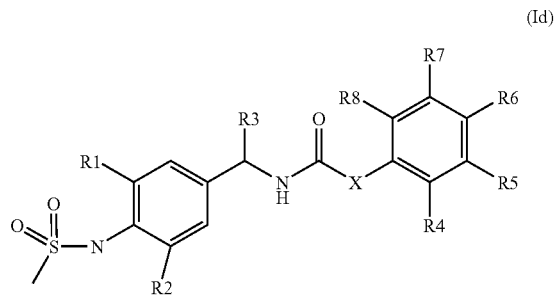

(Id)

wherein R1, R2, R3, R4, R5, R6, R7, R8 and X have the meaning as defined in claim 1.

12. A compound according to claim 1 or pharmaceutically acceptable salt thereof, wherein the compound is selected from the group consisting of:

N-{-4-[3-(4-t-butylbenzyl)ureidomethyl]-2-vinylphenyl}methanesulfonamide,

N-{-4-[3-(4-t-butylbenzyl)ureidomethyl]-2-fluoro-6-vinylphenyl}methanesulfonamide, N-{-4-[3-(4-t-butylbenzyl)ureidomethyl]-2-ethynyl-6-fluorophenyl}methanesulfonamide,
N-{-4-[3-(4-t-butylbenzyl)ureidomethyl]-5-chloro-2-vinylphenyl}methanesulfonamide,
N-{-4-[3-(4-t-butylbenzyl)ureidomethyl]-5-chloro-2-ethynylphenyl}methanesulfonamide,
N-(4-{1-(R)-[3-(4-t-butylbenzyl)ureido]ethyl}-2-vinylphenyl)methanesulfonamide,
(R)—N-(4-{1-[3-(4-t-butyl-benzyl)-ureido]-ethyl}-2-fluoro-6-vinyl-phenyl)methanesulfonamide,
N-{-4-[3-(4-t-butyl-benzyl)-ureidomethyl]-2-methyl-6-vinyl-phenyl}methanesulfonamide,
N-{-4-[3-(4-t-butyl-benzyl)-ureidomethyl]-2-chloro-6-vinyl-phenyl}methanesulfonamide,
3-(4-t-butylphenyl)propynoic acid 3-fluoro-4-methanesulfonylamino-5-vinylbenzylamide,
3-(4-t-butylphenyl)propynoic acid [1-(3-fluoro-4-methanesulfonylamino-5-vinylphenyl)ethyl]amide,
3-(4-t-butylphenyl)-N-[1-(R)-(4-methanesulfonylamino-3-vinylphenyl)ethyl]acrylamide,
3-(4-t-butylphenyl)-N-(3-fluoro-4-methanesulfonylamino-5-vinylbenzyl)acrylamide,
3-(4-t-butylphenyl)-N-(3-fluoro-5-ethynyl-4-methanesulfonyl amino-benzyl)acrylamide,
3-(4-t-butylphenyl)-N-(4-methanesulfonylamino-3-vinylbenzyl)acrylamide,
3-(4-trifluoromethylphenyl)-N-(4-methanesulfonylamino-3-vinylbenzyl)acrylamide,
3-(4-t-butylphenyl)-N-(3-chloro-4-methanesulfonylamino-5-vinylbenzyl)acrylamide,
3-(4-t-butyl-2-morpholin-4-yl-phenyl)-N-(3-fluoro-4-methanesulfonylamino-5-vinylbenzyl)acrylamide,
3-(4-t-butyl-2-methoyethoxy-phenyl)-N-(3-fluoro-4-methanesulfonylamino-5-vinylbenzyl)acrylamide,
3-[4-t-butyl-2-(2-methoxyethylamino)phenyl]-N-(3-fluoro-4-methanesulfonylamino-5-vinylbenzyl)acrylamide,
3-(4-t-butyl-2-methoxyphenyl)-N-(3-fluoro-4-methanesulfonylamino-5-vinyl-benzyl)acrylamide,
3-(2-allyloxy-4-t-butylphenyl)-N-(3-fluoro-4-methanesulfonylamino-5-vinylbenzyl)acrylamide,
3-[4-t-butyl-2-(3-methylbutylamino)phenyl]-N-(3-fluoro-4-methanesulfonylamino-5-vinylbenzyl)acrylamide,
3-(4-t-butyl-2-isopropylaminophenyl)-N-(3-fluoro-4-methanesulfonylamino-5-vinylbenzyl)acrylamide,
3-(4-t-butylphenyl)-N-[1-(3-fluoro-4-methanesulfonylamino-5-vinylphenyl)ethyl]propionamide,
3-(4-t-butylphenyl)-N-[1-(3-fluoro-4-methanesulfonylamino-5-vinylphenyl)ethyl]acrylamide,
3-(4-t-butylphenyl)-N-(3-fluoro-4-methanesulfonylamino-5-vinylbenzyl)-2-methylacrylamide,
3-(4-t-butylphenyl)-2-fluoro-N-(3-fluoro-4-methanesulfonylamino-5-vinylbenzyl)acrylamide,
3-[4-t-butyl-2-(tetrahydropyran-4-yloxy)phenyl]-N-(3-fluoro-4-methanesulfonylamino-5-vinylbenzyl)acrylamide,
3-[4-t-butyl-2-(tetrahydropyran-4-yloxy)phenyl]-N-(3-fluoro-4-methanesulfonylamino-5-vinylbenzyl)propionamide,
3-(4-t-butylphenyl)-N-[1-(4-methanesulfonylamino-3-vinylphenyl)ethyl]-2-methylacrylamide,
3-(4-t-butylphenyl)-N-(3-fluoro-4-methanesulfonylamino-5-vinylbenzyl)-2-methylpropionamide,
3-[4-(tert-butyl)phenyl]-N-[4-(methanesulfonylamino)-3-vinylbenzyl]propionamide,
3-[4-(tert-butyl)phenyl]-N-[3-fluoro-4-(methanesulfonylamino)-5-vinylbenzyl]propionamide,
3-(4-t-butyl-phenyl)-N-(3-ethynyl-5-fluoro-4-methanesulfonylamino-benzyl)-propionamide,
N-(4-{1-[3-(4-t-butylphenyl)ureido]ethyl}-2-vinylphenyl)methanesulfonamide,
N-(4-{1-[3-(4-t-butylphenyl)ureido]ethyl}-2-ethynylphenyl)methanesulfonamide,
N-{-4-[3-(4-t-butylphenyl)ureidomethyl]-2-fluoro-6-vinylphenyl}methanesulfonamide, and
Ethenesulfonic acid (4-{1-[3-(4-t-butylphenyl)ureido]ethyl}-2-vinylphenyl)amide.

13. A compound according to claim 12 or pharmaceutically acceptable salt thereof, wherein the compound is selected from the group consisting of
(R)—N-(4-{1-[3-(4-t-butyl-benzyl)-ureido]-ethyl}-2-fluoro-6-vinyl-phenyl)-methanesulfonamide,
3-(4-t-butylphenyl)-N-[1-(R)-(4-methanesulfonylamino-3-vinyl-phenyl)ethyl]acrylamide,
3-(4-t-butylphenyl)-N-(3-fluoro-4-methanesulfonylamino-5-vinyl-benzyl)acrylamide,
3-(4-t-butylphenyl)-N-(3-fluoro-5-ethynyl-4-methanesulfonyl amino-benzyl)acrylamide,
(R)-3-(4-t-butylphenyl)-N-[1-(3-fluoro-4-methanesulfonylamino-5-vinylphenyl)ethyl]propionamide,
3-(4-t-butylphenyl)-N-(3-fluoro-4-methanesulfonylamino-5-vinylbenzyl)-2-methylacrylamide,
3-[4-t-butyl-2-(tetrahydropyran-4-yloxy)phenyl]-N-(3-fluoro-4-methanesulfonylamino-5-vinylbenzyl)propionamide,
(R)-3-(4-t-butylphenyl)-N-[1-(4-methanesulfonylamino-3-vinylphenyl)ethyl]-2-methylacrylamide,
N-{4-[3-(4-t-butylbenzyl)ureidomethyl]-2-fluoro-6-vinylphenyl}methanesulfonamide,
N-{-4-[3-(4-t-butylbenzyl)ureidomethyl]-2-ethynyl-6-fluorophenyl}methanesulfonamide,
3-(4-tert-Butylphenyl)propynoic acid 3-fluoro-4-methanesulfonylamino-5-vinylbenzylamide,
3-(4-t-butylphenyl)-N-(4-methanesulfonylamino-3-vinylbenzyl)acrylamide,
3-[4-tert-Butyl-2-(2-methoxy-ethoxy)-phenyl]-N-(3-fluoro-4-methanesulfonylamino-5-vinyl-benzyl)-acrylamide,
3-[4-tert-Butyl-2-(2-methoxyethylamino)phenyl]-N-(3-fluoro-4-methanesulfonylamino-5-vinylbenzyl)acrylamide,
3-(4-tert-Butyl-2-methoxyphenyl)-N-(3-fluoro-4-methanesulfonylamino-5-vinyl-benzyl)acrylamide,
3-(2-Allyloxy-4-tert-butylphenyl)-N-(3-fluoro-4-methanesulfonylamino-5-vinylbenzyl)acrylamide,
(R)-3-(4-tert-Butylphenyl)-N-[1-(3-fluoro-4-methanesulfonylamino-5-vinylphenyl)ethyl]acrylamide,
3-(4-tert-Butylphenyl)-N-(3-fluoro-4-methanesulfonylamino-5-vinylbenzyl)-2-methylpropionamide,
3-[4-(tert-butyl)phenyl]-N-[4-(methanesulfonylamino)-3-vinylbenzyl]propionamide,
N-(4-{1-(R)-[3-(4-t-butylbenzyl)ureido]ethyl}-2-vinylphenyl)methanesulfonamide,
3-[4-(tert-butyl)phenyl]-N-[3-fluoro-4-(methanesulfonylamino)-5-vinylbenzyl]propionamide, and
(R)—N-(4-{1-[3-(4-tert-Butylphenyl)ureido]ethyl}-2-vinylphenyl)methanesulfonamide.

14. A pharmaceutical composition comprising a compound according to claim 1 or pharmaceutically acceptable salt thereof together with a pharmaceutically acceptable carrier.

15. The pharmaceutical composition of claim 14, wherein the composition is for oral administration.

16. A method for treating a subject suffering from a condition selected from pain, inflammatory disease of the joints, urinary bladder hypersensitivity including urinary incontinence, stomach duodenal ulcer, irritable bowel syndrome, inflammatory bowel disease, neurotic/allergic/inflammatory skin disease, psoriasis, asthma, chronic obstructive pulmonary disease, pruritus and prurigo, comprising administering to said subject an effective amount of the compound according to claim 1 or pharmaceutically acceptable salt thereof.

17. The method according to claim 16, wherein the pain is, or is associated with, a condition selected from the group consisting of osteoarthritis, rheumatoid arthritis, ankylosing spondylitis, diabetic neuropathic pain, post-operative pain, non-inflammatory musculoskeletal pain, fibromyalgia, myofascial pain syndrome, back pain, migraine and other types of headache.

18. A method for inhibiting vanilloid ligand from binding to vanilloid receptor in a patient, comprising contacting cells expressing vanilloid receptor in the patient with a compound according to claim 1 or pharmaceutically acceptable salt thereof.

* * * * *